United States Patent
Obenchain

(10) Patent No.: US 10,821,243 B2
(45) Date of Patent: *Nov. 3, 2020

(54) GAS SUPPLY WARNING AND COMMUNICATION SYSTEM

(71) Applicant: Advanced Interactive Response Systems LLC, Newaygo, MI (US)

(72) Inventor: Valerie A. Obenchain, Newaygo, MI (US)

(73) Assignee: Advanced Interactive Response Systems, LLC, Newaygo, MI (US)

(*) Notice: Subject to any disclaimer, the term of this patent is extended or adjusted under 35 U.S.C. 154(b) by 752 days.

This patent is subject to a terminal disclaimer.

(21) Appl. No.: 15/623,845

(22) Filed: Jun. 15, 2017

(65) Prior Publication Data

US 2018/0028769 A1 Feb. 1, 2018

Related U.S. Application Data

(63) Continuation-in-part of application No. 14/093,851, filed on Dec. 2, 2013, now Pat. No. 9,714,860, which (Continued)

(51) Int. Cl.
*A61M 16/00* (2006.01)
*A61M 16/20* (2006.01)
(Continued)

(52) U.S. Cl.
CPC .... *A61M 16/0051* (2013.01); *A61M 16/0672* (2014.02); *A61M 16/08* (2013.01);
(Continued)

(58) Field of Classification Search
CPC .............. A61M 5/142; A61M 5/16809; A61M 13/003; A61M 16/0051; A61M 16/0666;
(Continued)

(56) References Cited

U.S. PATENT DOCUMENTS 1,529,605 A 3/1925 Muncey
2,402,167 A 6/1946 Silver
(Continued)

FOREIGN PATENT DOCUMENTS

DE 10041848 3/2002

*Primary Examiner* — Stephen R Burgdorf
(74) *Attorney, Agent, or Firm* — Kohn & Associates, PLLC

(57) ABSTRACT

A fluid supply warning and communication system including fluid tight engagements being made with tubing having at least one connector end chosen from a universal connector, a twist-on nipple, and a v-shaped end. A gas supply warning and communication system including a first upstream gas path, a second upstream gas path, and a downstream gas path made with tubing having at least one connector end chosen from a universal connector, a twist-on nipple, and a v-shaped end. A method of increasing humidity in a downstream gas path in the gas supply warning and communication system by flowing gas through a downstream gas path tubing that increases humidity to an end use appliance.

29 Claims, 61 Drawing Sheets

Related U.S. Application Data is a continuation-in-part of application No. 13/085,877, filed on Apr. 13, 2011, now Pat. No. 8,653,979.

(60) Provisional application No. 61/323,845, filed on Apr. 13, 2010.

(51) Int. Cl.

| | | |
|---|---|---|
| *F17C 13/02* | (2006.01) | |
| *F17C 13/04* | (2006.01) | |
| *G08B 21/18* | (2006.01) | |
| *G08B 21/02* | (2006.01) | |
| *G08B 25/08* | (2006.01) | |
| *A62B 9/00* | (2006.01) | |
| *G01L 19/12* | (2006.01) | |
| *A61M 16/06* | (2006.01) | |
| *A61M 16/08* | (2006.01) | |
| *A61M 16/10* | (2006.01) | |
| *A61M 16/16* | (2006.01) | |

(52) U.S. Cl.
CPC ........ *A61M 16/1055* (2013.01); *A61M 16/16* (2013.01); *A61M 16/20* (2013.01); *A61M 16/202* (2014.02); *A62B 9/00* (2013.01); *A62B 9/006* (2013.01); *F17C 13/02* (2013.01); *F17C 13/04* (2013.01); *G01L 19/12* (2013.01); *G08B 21/02* (2013.01); *G08B 21/182* (2013.01); *G08B 25/08* (2013.01); *A61M 16/101* (2014.02); *A61M 2016/0027* (2013.01); *A61M 2016/0039* (2013.01); *A61M 2016/1025* (2013.01); *A61M 2205/0205* (2013.01); *A61M 2205/16* (2013.01); *A61M 2205/18* (2013.01); *A61M 2205/3331* (2013.01); *A61M 2205/3569* (2013.01); *A61M 2205/502* (2013.01); *A61M 2205/581* (2013.01); *A61M 2205/583* (2013.01); *A61M 2205/587* (2013.01); *A61M 2205/8206* (2013.01); *A61M 2205/8262* (2013.01); *A61M 2209/00* (2013.01); *A61M 2209/01* (2013.01); *A61M 2230/06* (2013.01); *A61M 2230/205* (2013.01); *A61M 2230/432* (2013.01); *F17C 2201/0109* (2013.01); *F17C 2201/056* (2013.01); *F17C 2221/011* (2013.01); *F17C 2223/0123* (2013.01); *F17C 2227/046* (2013.01); *F17C 2250/032* (2013.01); *F17C 2250/034* (2013.01); *F17C 2250/043* (2013.01); *F17C 2250/0443* (2013.01); *F17C 2250/077* (2013.01); *F17C 2270/025* (2013.01)

(58) Field of Classification Search
CPC .. A61M 16/0672; A61M 16/08; A61M 16/10; A61M 16/101; A61M 16/1055; A61M 16/12; A61M 16/16; A61M 16/20; A61M 16/202; A61M 16/24; A61M 16/6816; A61M 2016/0027; A61M 2016/0059; A61M 2016/1025; A61M 2205/0205; A61M 2205/16; A61M 2205/18; A61M 2205/3331; A61M 2205/3569; A61M 2205/502; A61M 2205/581; A61M 2205/583; A61M 2205/587; A61M 2205/8206; A61M 2205/8262; A61M 2209/00; A61M 2209/01; A61M 2230/06; A61M 2230/225; A61M 2230/432; A62B 9/006; F17C 13/02; F17C 13/04; F17C 2201/0109; F17C 2223/0123; F17C 2227/046; F17C 2250/032; F17C 2250/034; F17C 2250/043; F17C 2250/0443; F17C 2250/077; F17C 2270/025; G01F 23/18; G01L 19/12; G08B 21/02; G08B 21/182; G08B 25/08
USPC ........................................................ 340/870.9
See application file for complete search history.

(56) References Cited

U.S. PATENT DOCUMENTS

| | | |
|---|---|---|
| 3,277,977 A | 10/1966 | Silverman |
| 3,740,739 A | 6/1973 | Griffin, III et al. |
| 3,823,575 A | 7/1974 | Parel |
| 4,367,133 A | 1/1983 | Lauer |
| 4,648,888 A | 3/1987 | Rowland |
| 4,763,114 A | 8/1988 | Edismore |
| 5,062,443 A | 11/1991 | Maric |
| 5,554,976 A | 9/1996 | Miyauchi et al. |
| 5,788,688 A | 8/1998 | Bauer et al. |
| 5,906,672 A | 5/1999 | Michaels et al. |
| 6,077,331 A | 6/2000 | Phillips |
| 6,542,848 B1 | 4/2003 | Neeser |
| 6,560,960 B2 | 5/2003 | Nishimura et al. |
| 6,575,164 B1 | 6/2003 | Jaffe et al. |
| 6,581,593 B1 * | 6/2003 | Rubin ................. F16L 19/0206 128/202.27 |
| 6,683,535 B1 | 1/2004 | Utke |
| 6,722,399 B1 | 4/2004 | Cano |
| 6,763,843 B1 | 7/2004 | Dickerson, Jr. |
| 7,032,606 B1 | 4/2006 | Lucas, Jr. et al. |
| 8,810,394 B2 * | 8/2014 | Kalpin ............. A61M 5/14276 340/540 |
| 2002/0014240 A1 | 2/2002 | Truschel |
| 2002/0088464 A1 | 7/2002 | Truschel |
| 2002/0124845 A1 * | 9/2002 | Lauer .................... A61M 16/08 128/202.27 |
| 2002/0176323 A1 | 11/2002 | Magine et al. |
| 2002/0195105 A1 | 12/2002 | Blue et al. |
| 2003/0189492 A1 | 10/2003 | Harvie |
| 2004/0074540 A1 | 4/2004 | Pearson |
| 2004/0112435 A1 | 6/2004 | Olander |
| 2004/0139973 A1 * | 7/2004 | Wright .............. A61M 16/0672 128/207.18 |
| 2004/0159323 A1 | 8/2004 | Schmidt et al. |
| 2004/0204870 A1 | 10/2004 | Schimnowski et al. |
| 2004/0217871 A1 | 11/2004 | Shoub |
| 2005/0024216 A1 | 2/2005 | Crooks et al. |
| 2005/0083205 A1 | 4/2005 | Deacy |
| 2005/0087042 A1 | 4/2005 | Huang |
| 2006/0219245 A1 | 10/2006 | Holder |
| 2006/0290525 A1 | 12/2006 | Anderson et al. |
| 2007/0193340 A1 | 8/2007 | Yoshida |
| 2008/0027344 A1 | 1/2008 | Terry |
| 2008/0072904 A1 | 3/2008 | Becker et al. |
| 2008/0191466 A1 * | 8/2008 | Knipple ............ A61M 16/0816 285/31 |
| 2008/0251074 A1 | 10/2008 | Sand |
| 2009/0165671 A1 | 7/2009 | Struyk |
| 2010/0031960 A1 | 2/2010 | Knight et al. |
| 2010/0097232 A1 | 4/2010 | Lee et al. |
| 2010/0193045 A1 | 8/2010 | Xu |
| 2010/0306992 A1 | 12/2010 | Cooke |
| 2011/0213531 A1 | 9/2011 | Farley et al. |
| 2011/0248856 A1 | 10/2011 | Obenchain |
| 2012/0125333 A1 | 5/2012 | Bedford |
| 2013/0072862 A1 | 3/2013 | Blackhurst |
| 2014/0152468 A1 | 6/2014 | Obenchain |
| 2015/0320952 A1 | 11/2015 | Acker et al. |
| 2017/0156649 A1 | 6/2017 | Modi |

\* cited by examiner

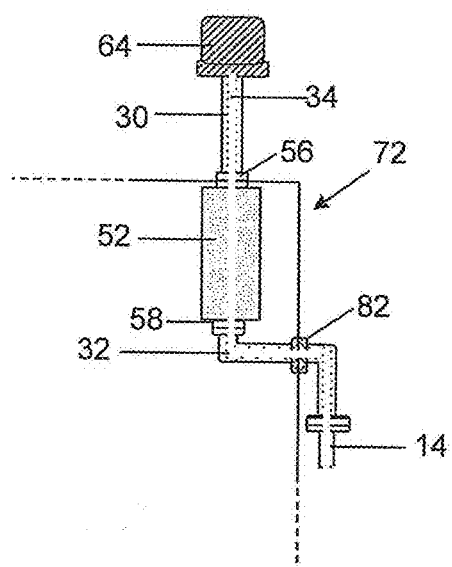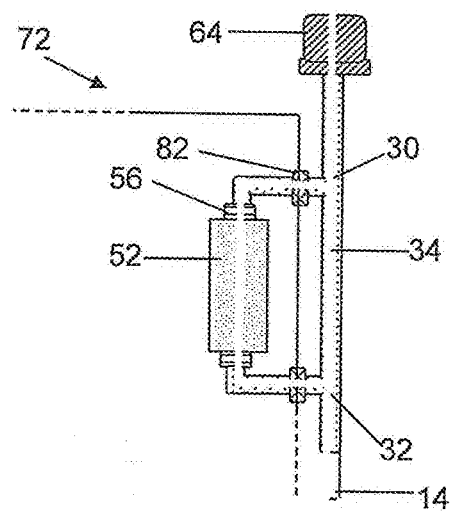
Fig. 3A
Fig. 3B

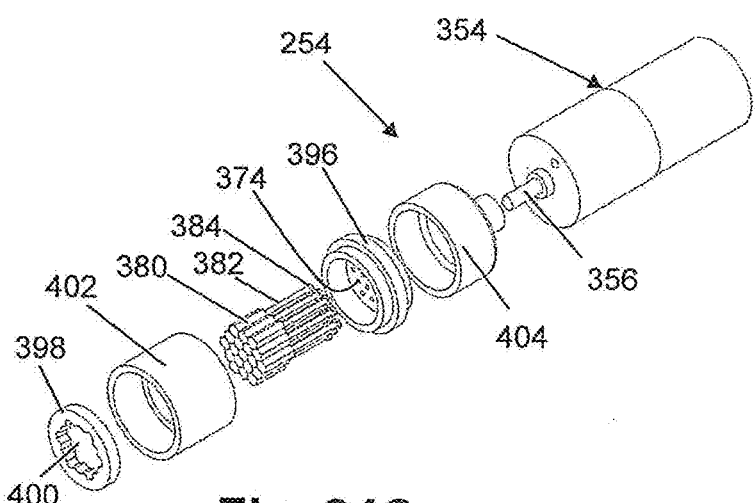
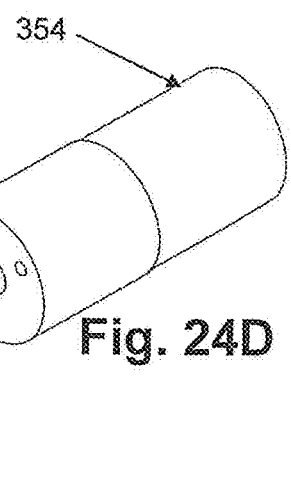
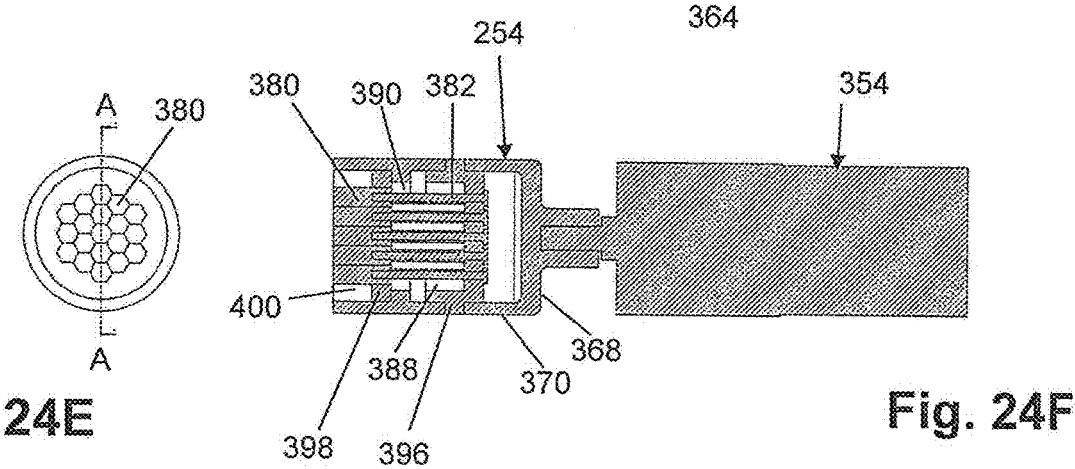
Fig. 24C
Fig. 24D
Fig. 24E
Fig. 24F

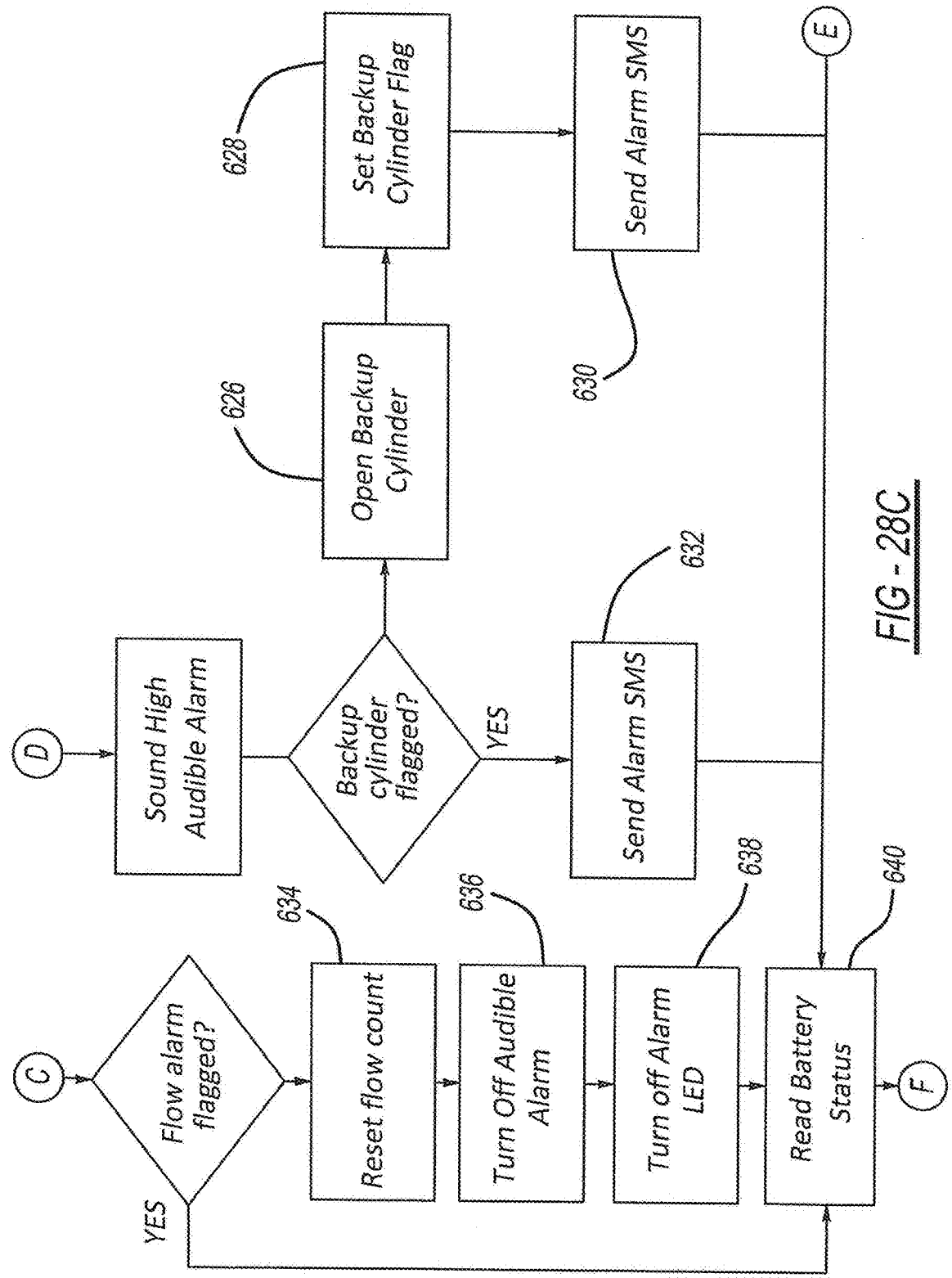

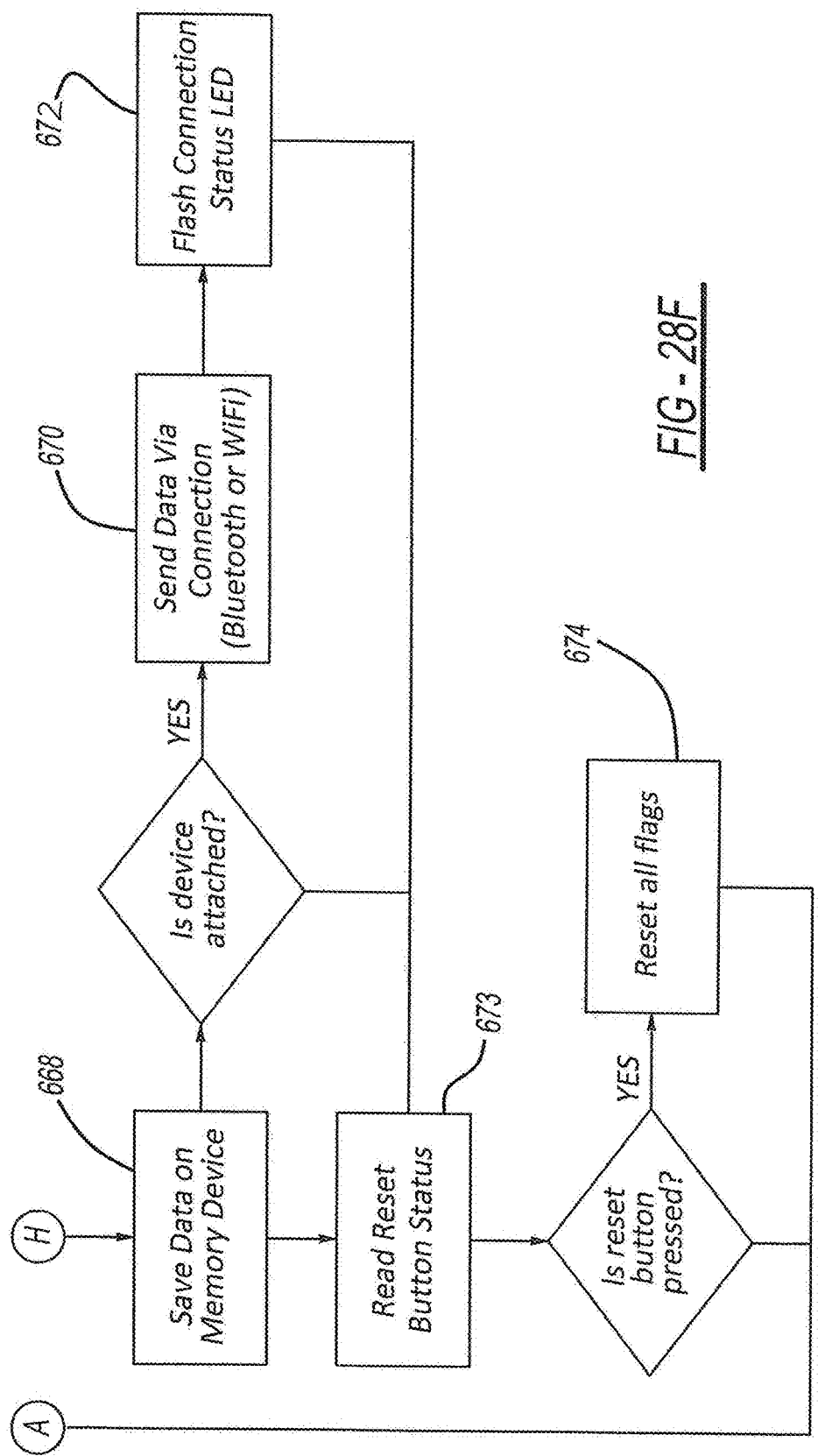

In-Home Patient

- Activate
- Register
- Manage Contacts- emergency contact, send/revoke invites, secondary contacts, caregivers, oxygen suppliers, alert settings
- My Account- email, address, phone number, billing info
- Help- tutorials, FAQ, videos, support, contact us
- Patient View
- Device Management- firmware update, link devices, set time zone, sleep mode
- Actors- administrators, nurse, doctor, patients, family members, oxygen suppliers

FIGURE 45A

Nursing Homes/Hospitals

- Device Management
- Patient search
- Patient- patient, families, assigned caregivers (patient specific alerts, graphs and history)
- Status Page/Alerts Page- landing page
- Management Console (Administrator)- settings, user management, alert settings, facility settings, adding/changing users, resetting passwords, deactivate users
- Device Updates- firmware updates, link devices, set time zone, sleep mode
- Actors- administrator, nurse, doctor, patient, family members, oxygen suppliers

FIGURE 45B

AIRS Team

- Customer Management- freeze account, payment, history, billing info
- Repurpose Device
- Device Management- firmware updates, link devices, set time zone, sleep mode
- Actors- AIRS' customer service rep, collections, tech support

FIGURE 45C

Data Collected

- Flow
- Pressure
- Tank Status
- Oxygen percentage
- ETCO2
- SPO2
- Patient's pulse
- Battery Status
- Device status
- Alerts

FIGURE 45D

GAS SUPPLY WARNING AND COMMUNICATION SYSTEM

BACKGROUND OF THE INVENTION

1. Technical Field

The present invention relates generally to an alarm device to warn of and remedy malfunctions in a pressurized gas system and more specifically to communicate malfunction warnings to remote users, and to allow remote users to control the alarm device.

2. Background Art

Pressurized gas systems are used in respiratory therapy, in medical procedures and testing, in the breathing apparatuses of divers and firefighters, and in such industrial fields as welding, heating, ventilation, and air conditioning (HVAC), and plumbing. It is important to provide users of these systems with an alarm to indicate that the supply of gas has been or is about to be exhausted, or that the flow of gas has been interrupted. Pressurized gas alarm systems indicate these conditions by means of audible alarms, alarm lights, and the like. Such alarms are especially critical in medical gas uses, where a patient's life may be threatened by the interruption of the flow of oxygen or other gas. In a medical setting, a warning alarm must be perceived not only by the end user of the gas, who may be an incapacitated patient, but also by caregivers, who may be at sites remote from the end user. It is therefore desirable to provide electrically powered alarms, whose warnings can be communicated over distances by wires or by wireless broadcast systems.

A typical pressurized gas system includes at least one gas reservoir, such as a cylinder, tank, or canister to store gas, usually at high pressure. The term "gas reservoir" also includes low pressure gas sources such as oxygen concentrators, and other gas sources which do not require regulators. A pressurized gas system also typically includes a regulator to allow the gas to flow into a gas line at a constant reduced pressure, and at an appropriate flow rate. The term "pressurized gas system" is defined to include a reservoir, such as a pressurized gas cylinder or an oxygen concentrator, a regulator, if present, and all lines which conduct the gas, and the end use appliance such as a mask, cannula, tent, incubator, or torch. The term "downstream" is defined as the direction of gas flow away from a cylinder or other reservoir.

Typically, a gas cylinder includes a main valve and cylinder connector to which a regulator is attached. When the cylinder valve is opened, pressurized gas is admitted into the regulator. Regulators typically include at least two valves. A pressure valve maintains a constant user selected pressure downstream of the cylinder. It maintains that pressure as tank pressure decreases and downstream demand changes, typically by means of a diaphragm-controlled valve. A flow valve, downstream of the pressure valve, regulates the flow rate of gas out of the regulator. It is the flow valve that directly determines the flow rate of gas into a downstream appliance.

There are two types of malfunctions that can cause a loss of gas flow at a downstream appliance. The first cause is the exhaustion of gas in the cylinder. Cylinder pressure alarm devices exist in the prior art to provide an alarm indication when a gas cylinder has been exhausted, or when gas pressure in the cylinder has fallen to a predetermined limit. These alarm devices generally include a cylinder pressure sensor that actuates an electronic or mechanical alarm when cylinder pressure reaches a minimum set point. These devices sense gas pressure at a point downstream of the cylinder valve and upstream of the pressure valve of the regulator. It is in this region that tank pressure can be reliably sensed when the cylinder valve is open. Such devices are disclosed in U.S. Pat. No. 6,209,579 to Bowden et al., U.S. Pat. No. 5,040,477 to Schiffmacher, U.S. Pat. No. 6,137,417 to McDermott, and US Patent Application Publication No. US2010/0097232 to Lee et al.

A cylinder pressure sensor, however, is ineffective at detecting the second type of gas flow malfunction: malfunctions that occur in the gas lines downstream of the flow valve of a flow regulator. These downstream malfunctions include the disconnection of a gas line from the flow valve; the disconnection of two joined gas lines; the disconnection of a gas line from an appliance; a leak in a gas line or appliance; and blockages, such as a clog or kink in a gas line.

Cylinder pressure alarms cannot react to these downstream malfunctions. Their pressure sensors are isolated from pressure and flow conditions in the downstream gas lines by at least the pressure valve and flow valve, and in some cases by additional intervening valves. Cylinder pressure alarms are also inapplicable to oxygen concentrators.

Alarm devices which monitor gas flow rate have the potential to detect malfunctions occurring downstream of a regulator, and also to detect depletion of a pressurized gas cylinder or other reservoir. They are also potentially applicable to oxygen concentrators and other devices that employ fans or compressors to generate a gas flow. Disconnections, leaks and blockages, are detectable by gas flow detectors as reductions in gas flow rate by a gas flow sensor located downstream of the malfunction. Disconnections and leaks can also be detected by gas flow sensors upstream of the malfunction, as increases in gas flow rate, which reflect the decreased gas flow resistance caused by a disconnection or leak. The depletion of a gas cylinder or other gas reservoir is also detectable by a gas flow detector situated downstream of a regulator. Even though a regulator buffers the downstream gas lines from changes in cylinder pressure, the near or complete exhaustion of the cylinder will of course produce detectable reduction in gas flow rate downstream. Alarm devices which monitor gas flow are also applicable to oxygen concentrators and other devices that produce gas flow by means of fans or compressors, rather than by means of a pressurized cylinder.

A gas flow alarm device exists in the prior art, but it cannot warn of all malfunctions occurring downstream of a regulator, or of the depletion of a pressurized gas cylinder or other reservoir. U.S. Pat. No. 6,386,196 to Culton discloses a gas flow alarm to detect the detachment of an oxygen line from an oxygen cannula, or between two segments of oxygen line. The alarm consists of a coupler with a proximal end accepting an upstream oxygen line and a distal end connecting to a downstream oxygen line or cannula. The coupler includes an audible alarm, in the form of a whistle at the proximal end. The whistle is normally occluded by the downstream line but is uncovered when the line is disconnected. Upon disconnection, the uncovered whistle, powered by the gas flow from upstream, emits an audible alarm tone. The coupler also includes a visual indication of flow, a small propeller, enclosed in the coupler, which rotates in the gas flow.

The alarm device disclosed by Culton can only sound an alarm in response to a disconnection downstream of the alarm device itself. It cannot sound an alarm if there is a disconnection, leak, or blockage upstream of the alarm device, or if the gas reservoir becomes exhausted. These malfunctions all cut off the gas flow which powers the whistle. The duration of the whistle alert is also limited by the amount of gas available to power the whistle. Furthermore, the whistle can only be perceived by those in the immediate vicinity of the alarm. Should a gas flow malfunction occur upstream of the alarm disclosed by Culton, the only warning is the cessation of rotation of the small enclosed propeller. This cessation is perceivable only by individuals who happen to be scrutinizing the propeller at the time of malfunction. This hardly qualifies as a warning.

There is a need for a gas flow warning alarm that can detect the gas flow malfunctions at any point downstream of a gas reservoir, detects cylinder exhaustion, and produces an alarm indication that is autonomous of gas pressure and perceivable at remote locations and without constant scrutiny of the alarm device. A warning alarm device that detects gas flow malfunctions downstream of a regulator flow valve has one shortcoming. It can provide little advance warning of exhaustion of a gas cylinder or other pressurized gas reservoir. Because a regulator maintains constant flow, exhaustion of the cylinder can be detected only at the point where cylinder pressure has fallen to the point where gas flow ceases. A device that senses cylinder pressure upstream of a regulator pressure valve can be set to provide an alarm at a predetermined pressure, which can be set high enough to provide advance warning of depletion.

When the pressure of a gas reservoir such as an oxygen cylinder does drop below a predetermined limit, there may be no one available to perceive an alarm indication or to exchange a depleted cylinder for a fresh cylinder. There is therefore a need for a device that automatically opens a reserve gas cylinder into a pressurized gas system in response to a pressure alarm indication.

In systems wherein an oxygen concentrator serves as the primary gas reservoir, malfunctions are best detected as a reduction in the concentration of oxygen in the output stream. This malfunction cannot be detected by a drop in pressure or gas flow, but rather by analysis of the output stream by an oxygen analyzer. There is a need for a device which detects a reduction in oxygen output by an oxygen concentrator and automatically opens a reserve oxygen cylinder to temporarily supplement or replace the output of the oxygen concentrator.

A pressurized gas system often requires monitoring by remote users, that is, parties not directly connected to the system or in its immediate vicinity. Remote users include caregivers of patients on oxygen systems and homeowners whose homes include utilities fueled by propane or another gas fuel. There is a need for a warning, communication, and control device that enables remote users to monitor and control a pressurized gas system.

A common cause of malfunction in a pressurized gas system is the dislodgment of flexible gas tubing from the outlets or connectors to which they are affixed. Disconnection is usually caused by inadvertent application or physical force or a transient overpressure at an end of the tubing. There is a need for a flexible tube end that grips an outlet or connector and resists dislodgment.

SUMMARY OF THE INVENTION

The present invention provides for a fluid supply warning and communication system including a primary reservoir pressure monitor module in fluid tight engagement with an outlet of a primary fluid reservoir, for sensing primary reservoir pressure in a pressurized fluid system, and generating a primary reservoir pressure error signal in response to sensing a reservoir pressure data violative of at least one predetermined pressure limit. The primary reservoir pressure monitor module is in fluid tight engagement with a first upstream path for directing fluid from the primary fluid reservoir, the primary reservoir pressure monitor module not in fluid or mechanical engagement with the changeover/reservoir pressure monitor, the primary reservoir pressure monitor module including: a primary reservoir pressure sensor for measuring the fluid pressure of the primary fluid reservoir, and generating the primary reservoir pressure data.

A reservoir pressure error signal generator is in operative connection with the primary reservoir pressure sensor, for generating the primary reservoir pressure error signal in response to the receipt of reservoir pressure data violative of at least one predetermined pressure limit. A pressure monitor microprocessor is in operative connection with the primary reservoir pressure sensor and the reservoir pressure error signal generator, the pressure monitor microprocessor receiving the primary reservoir pressure data from the primary reservoir pressure sensor, and the primary reservoir pressure error signals from the pressure error signal generator, a pressure monitor transceiver in operative connection with the pressure monitor microprocessor, for electronic communication with a compatible central transceiver situated at the communications/flow monitor module, the pressure monitor microprocessor routing the primary reservoir pressure data and the primary reservoir pressure error signals to the pressure monitor transceiver for transmission to the central receiver.

A communications/flow monitor module is in electronic communication with the primary reservoir pressure monitor module, for receiving the primary reservoir pressure error signal and in response transmitting a reservoir changeover signal to a changeover/reservoir pressure monitor module in fluid tight engagement with a reserve fluid reservoir in the pressurized fluid system. The changeover/reservoir pressure monitor module includes a reservoir changeover device in mechanical engagement with a main valve of the reserve fluid reservoir, the changeover/reservoir pressure monitor module actuating the reservoir changeover device to open the reserve fluid reservoir to the pressurized fluid system upon receipt of the changeover signal, the changeover/reservoir pressure monitor module in fluid tight engagement with a second upstream path for directing fluid from the reserve fluid reservoir, the first and second upstream paths both in direct fluid tight engagement with the communications/flow monitor module, the communications/flow monitor module including a central microprocessor in operative connection with said central transceiver, the central microprocessor receiving the primary reservoir pressure error signal from the central transceiver and in response generating a reservoir changeover signal, the reservoir changeover signal being routed to central transceiver for transmission to a changeover transceiver situated at the changeover/reservoir pressure monitor module.

A digital display displays at least one of pressure, fluid flow rates, and percentage fluid in the primary fluid reservoir and the reserve fluid reservoir, and a user interface includes input buttons for setting alarms, the central microprocessor additionally in operative connection with the digital display, the central microprocessor driving the digital display to show a reservoir pressure value transmitted from a source selected from the primary reservoir pressure monitor module and the changeover/reservoir pressure module. The fluid tight engagements are made with tubing having at least one connector end chosen from a universal connector, a twist-on nipple, and a v-shaped end.

The present invention also provides for a gas supply warning and communication system including: a communication/oxygen monitor module in direct gas tight engagement with a first upstream gas path from a primary gas reservoir, in direct gas tight engagement with a second upstream gas path from a reserve gas reservoir, and in gas tight engagement with a downstream gas path toward at least one end use appliance, a changeover/reservoir pressure monitor module including a reservoir changeover device in mechanical engagement with a main valve of the reserve gas reservoir, and in electronic communication with the communications/flow monitor module, wherein the communication/oxygen monitor module includes: an oxygen sensor in exposed to said upstream path for generating oxygen concentration data, a voltmeter in operative connection with the oxygen sensor for calculating and displaying an oxygen concentration value, and an oxygen concentration error signal generator in operative connection with the voltmeter for generating an oxygen concentration error signal in response to an oxygen concentration value violative of at least one predetermined limit.

A central microprocessor is in operative connection with a central transceiver, the central microprocessor also in operative connection with the oxygen sensor, the voltmeter, and the oxygen concentration error signal generator, the central microprocessor receiving the oxygen concentration error signal from the oxygen concentration error signal generator and in response generating a reservoir changeover signal, the central microprocessor routing the reservoir changeover signal to the central transceiver for transmission to a compatible changeover transceiver situated at the changeover/reservoir pressure monitor module. A digital display displays at least one of pressure, gas flow rates, and percentage gas in the primary gas reservoir and the reserve gas reservoir, and a user interface includes input buttons for setting alarms. The first upstream gas path, the second upstream gas path, and downstream gas path are made with tubing having at least one connector end chosen from a universal connector, a twist-on nipple, and a v-shaped end.

The present invention also provides for a method of increasing humidity in a downstream gas path in the gas supply warning and communication system by flowing gas through a downstream gas path tubing that increases humidity to an end use appliance.

BRIEF DESCRIPTION OF THE DRAWINGS

Other advantages of the present invention will be readily appreciated as the same becomes better understood by reference to the following detailed description when considered in connection with the accompanying drawings, which are not necessarily drawn to scale, wherein:

FIG. 3A shows a front elevation of a conduit configured to permit the inclusion of a straight gas flow switch into the present invention;

FIG. 3B shows a front elevation of a conduit configured to permit the inclusion of a bypass gas flow switch in the present invention;

FIG. 24C shows an exploded perspective view of a reservoir changeover device according to the present invention;

FIG. 24D shows a perspective view of the reservoir changeover device;

FIG. 24E shows a bottom elevation of the reservoir changeover device;

FIG. 24F shows a cross sectional view of the reservoir changeover device, taken through axis A-A in FIG. 2E;

FIG. 28A, FIG. 28B, FIG. 28C, FIG. 28D, FIG. 28E, and FIG. 28F show a flow chart of an exemplary flow monitor control routine according to the present invention;

FIG. 45A shows example menus within the application for an in-home patient, FIG. 45B shows example menus for nursing home/hospitals, FIG. 45C shows example menus for system owners, and FIG. 45D shows examples of data that can be collected.

DETAILED DESCRIPTION OF THE INVENTION

Figure 1:
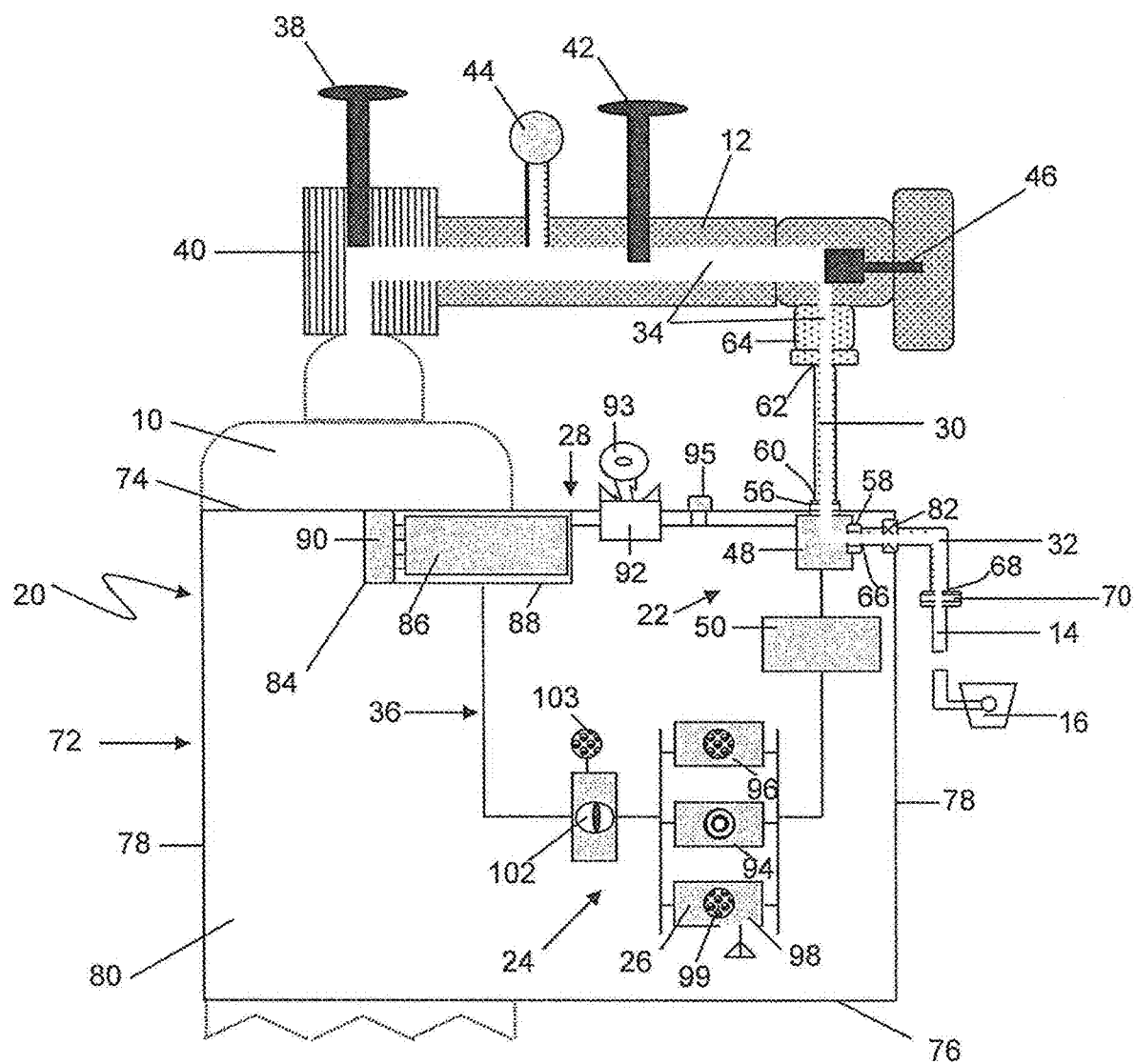
FIG. 1 shows a frontal semi-schematic view of the alarm device of the present invention, with front wall of housing removed.

The pressurized gas system of the present invention include digital displays and control to better and continually monitor the fluid delivered to a patient, as well as deliver alerts and provide automatic changeover to reserve fluid tanks when problems arise with a main tank unlike prior art systems. The pressurized gas system of the present invention can also use a variety of different tubing and connections for various purposes, as described below. A pressurized gas system is defined as a continuous series of vessels in gas-tight interrelationship for conducting gas from a region of high pressure to a region of low pressure. In the example illustrated in FIG. 1, the pressurized gas system is taken to include a gas cylinder 10 or other reservoir, a regulator 12, and all gas lines 14 and appliances 16 downstream of the regulator 12, exclusive of those incorporated into the present invention, which is generally shown at 20.

The alarm device 20 includes a flow sensing and error signaling subassembly 22 to sense a gas flow rate in the pressurized gas system and to generate an error signal when the gas flow rate violates at least one predetermined limit. Preferably the flow sensing and error signaling subassembly 22 is configured to generate an error signal when the gas flow rate violates either an upper or a lower limit. This permits detection of such malfunctions as obstructions or kinks in the pressurized gas system, or of depletion of the cylinder 10, both of which decrease gas flow rates downstream of the malfunction. The sensing of both upper and lower limit violations also permits the detection of leaks or disconnections in the pressurized gas system upstream of the leak or disconnection, because these malfunctions decrease resistance to gas flow, thereby increasing flow rate as detected upstream. Less preferably, the flow sensing and error signaling subassembly 22 can be configured to generate an error signal when the gas flow rate violates either a lower or an upper limit.

The alarm device 20 also includes an indicator subassembly 24, including at least one indicator mechanism 26 operatively connected to the flow sensing and error signaling subassembly 22 to produce a perceptible alarm indication in response to an error signal; a power subassembly 28 to provide and control electrical power to the flow sensing and error signaling subassembly 22 and indicator subassembly 24; and, optionally, tubular gas flow inlet and outlet conduits, 30 and 32 respectively, to direct a column of pressurized gas 34 into the flow sensing and error signaling subassembly 22. The alarm device also includes connection means 36 such as wiring, printed circuits, and the like, as required to operatively interconnect the components of the flow sensing and error signaling subassembly 22, indicator subassembly 24, and power subassembly 28.

Figure 2:
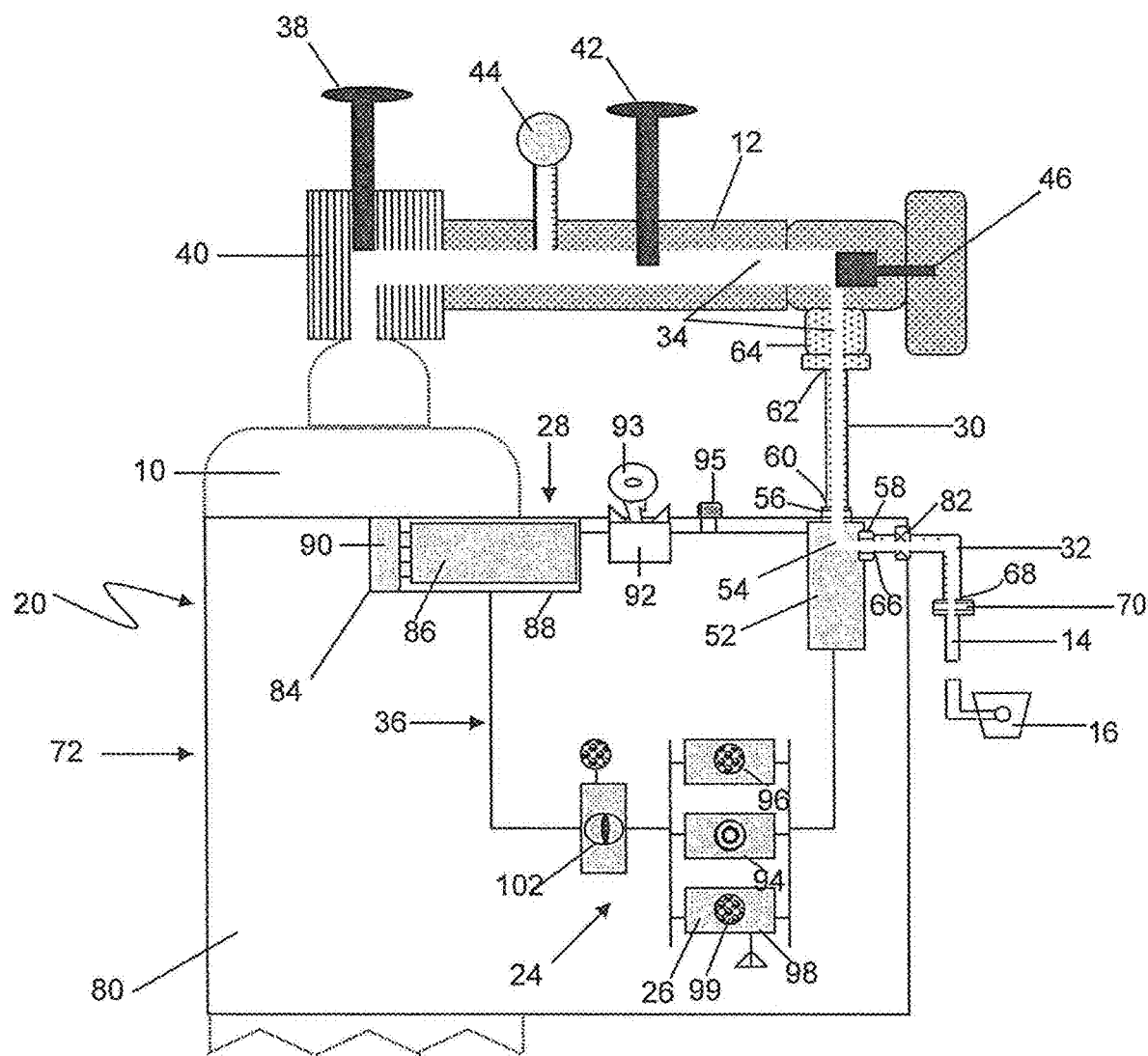
FIG. 2 shows a frontal semi-schematic view of the alarm device wherein the gas flow sensor and error signal generator are incorporated into a flow switch.

An example of the device of the present invention, adapted for use with a typical pressurized gas tank and regulator system for gases, is illustrated in FIG. 2. Oxygen is stored under pressure in the cylinder 10. The cylinder 10 includes a main valve 38 and a cylinder connector 40 to which the regulator 12 is attached in gas-tight engagement. The main valve 38 is opened to admit pressurized gas into the regulator 12. The regulator 12 includes a pressure valve 42 to regulate the pressure of gas exerted downstream of the cylinder 10. With the main valve 38 fully opened, cylinder pressure can be sensed reliably in the region downstream of the main valve 38 and upstream of the pressure valve 42. A cylinder pressure gauge 44 is often interposed into the pressurized gas stream 34 in this region. The regulator 12 also includes a flow valve 46, downstream of the pressure valve 42, to regulate the flow rate of gas downstream of the regulator 12. It is the flow valve 46 that determines the flow rate of gas into a downstream appliance 16, such as an oxygen mask or oxygen cannula. Gas flow rate can be sensed in the region downstream of the flow valve 46 and upstream of the appliance 16. It is the gas flow in this region that is sensed by the alarm device of the present invention.

The gas flow sensing and error signaling subassembly 22 includes a gas flow sensor 48 and an error signal generator 50. The gas flow sensor 48, upon detecting a gas flow rate violating a predetermined limit, is configured to induce the error signal generator to generate an error signal, preferably in the form of an electrical current.

Preferably gas flow sensor 48 and the error signal generator 50 are incorporated into a single unit, a gas flow switch 52, as illustrated in FIG. 2. The gas flow switch 52 includes an internal cavity 54 containing a sensor mechanism (not shown) and communicating with the pressurized gas system through a gas flow inlet 56 and a gas flow outlet 58. The gas flow inlet 56 receives the pressurized gas column 34, or a portion of thereof, via the gas flow inlet conduit 30. The gas flow inlet conduit 30 includes a downstream orifice 60 in gas-tight engagement with the gas flow inlet 56 of the gas flow switch 52, and an upstream orifice 62 in gas-tight engagement with the pressurized gas system at any point downstream of the flow valve 46 and upstream of the end use appliance 16. In the example illustrated in FIG. 2, the upstream orifice 62 of the gas flow inlet conduit 30 is mounted in gas-tight engagement with a regulator outlet 64 attached to the flow valve 46 of the regulator 12. Alternatively, the upstream orifice 62 can be engaged with the gas line 14 or appliance 16 at any point downstream of the regulator. If no flow valve 46 is present, then the upstream orifice 62 of the gas flow inlet conduit 30 can be in gas-tight engagement with the pressurized gas system at any point downstream of the pressure valve 42. If no regulator 12 is present, as is the case with an oxygen concentrator, a humidifier, or the outlet of an institutional gas system, then the upstream orifice 62 of the gas flow inlet conduit 30 can be in gas-tight engagement with the pressurized gas system at any point upstream of an end use appliance 16.

The gas flow outlet 58 of the gas flow sensor 48 or gas flow switch 52 is in gas-tight engagement with the upstream orifice 66 of the gas flow outlet conduit 32, which conducts the pressurized gas column 34 away from the internal cavity 54 of the flow switch 52. The gas flow outlet conduit 32 also includes a downstream orifice 68 in gas-tight engagement with the pressurized gas system at any point downstream of the gas flow switch 52. In the example illustrated if FIG. 2, the downstream orifice 68 of the gas flow outlet conduit 32 is mounted via a gas tight connector 70 to a gas line 14 leading to an appliance 16.

In operation, the column of pressurized gas 34 enters the internal cavity 54 of the gas flow switch 52 via the gas flow inlet conduit 30, actuates the gas flow sensor (not shown), and exits the internal cavity 54 via the gas flow outlet conduit 32.

The gas flow inlet conduit 30 and the gas flow outlet conduit 32 can be composed of metallic or rigid plastic tubing or of flexible plastic tubing. Metallic or rigid plastic tubing is preferable where the alarm device 20 is stably or permanently attached to a regulator or other gas outlet, or where durability and longevity of the attachment is desired. Suitable materials include but are not limited to brass, aluminum, steel or steel alloy, or nylon, Flexible plastic tubing is preferable where flexibility of attachment is more important than stability, or where durability and longevity are of lesser importance. Flexible plastic tubing compositions can include for example polypropylene, silicone, and polyethylene. It will be understood that the choice of tubing composition will depend in part on compatibility with the gas being conveyed.

For metallic or rigid plastic tubing, the gas-tight connection between the gas flow inlet conduit 30 and the gas flow inlet 56 of the gas flow sensor 48 or gas flow switch 52 is preferably made by a complementary screw threaded connection. A similar connection is preferably employed in the gas tight connection between the gas flow outlet 58 and the gas flow outlet 32. A similar connection is preferably employed in the gas-tight connection between the gas flow outlet 58 and the gas flow outlet conduit 32. The gas-tight connections of the orifices 62 and 68 of conduits 30 and 32 to the pressurized gas system up and downstream from the gas flow switch 52 can by made by any gas-tight sealing mechanism known in the art, such as a locking ring and silicone or rubber seal (not shown). For flexible plastic tubing, all connections between the gas flow inlet conduit 30, the gas flow inlet 56, the gas flow outlet conduit 32, the gas flow outlet 58, and the pressurized gas system, are preferably made by means of suitable plastic or metallic barbed fittings, push-to-connect fittings, compression fittings, or cam and groove couplings well known in the art. It will be understood that in embodiments of the invention intended for use with oxygen, all components coming into contact with oxygen will be oxygen-clean. In general, all components coming into contact with any gas or other fluid in the pressurized system will be constructed of materials compatible with that gas or fluid, with respect to flammability, chemical reactivity, and toxicity.

The gas flow switch 52 or other gas flow sensor 58 can alternatively connect directly to the regulator 12, and to downstream points of the pressurized gas system, without the intervention of conduits (not shown).

Preferably the gas flow switch 52 is a direct flow sensing switch wherein a sensor element is situated directly in the column of pressurized gas 34 moving through the pressurized gas system. One type of sensor is the piston type, whose displacement by gas flow completes an electrical circuit to generate an error signal when the gas flow rate is above or below a predetermined flow rate. Preferably the gas flow switch 52 is an FS-926 Piston Type Flow Switch (Gems Sensors, Plainville Conn.). Suitable alternatives include but are not limited to the Ameritrol IX Series Inline Flow Switch, a calorimetric type, which measures the cooling effect of a gas as it passes over a sensor (Ameritrol, Vista, Calif.). Appropriate flow rates are determined by the user according to the type and purpose of the pressurized gas system. For a medical oxygen cannula, a flow rate of 0.25 to 15 liters per minute (0.0088 to 0.5296 standard cubic feet per minute) may be appropriate. Alternatively, the gas flow switch 52 can include, but is not limited to, a mass flow sensor and a reed switch sensor.

The FS-926 gas flow switch is an angled body switch, that is, the column of pressurized gas 34 makes a right angle turn as it passes through the switch. The device of the present invention can also accommodate straight flow switches, wherein the column of pressurized gas 34 passes through the switch in a straight line (FIG. 3A), and also bypass switches, wherein only a portion of the column 34 is diverted through the switch (FIG. 3B). These accommodations can be made with minor adjustments of the geometry of the gas flow inlet conduit 30 and gas flow outlet conduit 32, as illustrated in FIGS. 1 and 3.

Flow sensors employing other types of sensing mechanisms can alternatively be employed, such as paddle, propeller, vane, and shuttle type sensors, a mass flow type sensor, a reed switch sensor, a calorimetric sensor and sensors that detect flow indirectly according to upstream and downstream pressure differences, such as a Bernouli sensor (not shown). A gas flow sensor 48 separate from the error signal generator 50 (FIG. 1) can be included to provide greater versatility than the gas flow switch 52. For example, the device can include a gas flow sensor 48 producing different signals in response to abnormally low gas flow and abnormally high gas flow. Such a sensor can provide distinctive alarm indications for a loss of gas flow, as would be expected downstream from a gas line blockage, disconnection, or cylinder depletion, and for high gas flow, as would be expected upstream of the disconnection of a end use appliance 16, depending upon where the gas flow sensor 48 is located. A gas flow sensor 48 which quantitates levels of gas flow, rather than simply detecting violations of flow limits, can alternatively be included, to provide continuous data on flow rate, in addition to an alarm indication. One example is the FS1015 Series mass flow sensor (Siargo Ltd., Santa Clara, Calif.). Another is the Honeywell Zephyr™ Digital Airflow Sensor, HAF Series (Honeywell Sensing and Control, Golden Valley, Minn.). Such sensors have the greatest utility when included in embodiments of the present invention that also include a microcontroller, to be described below.

The present invention includes at least one housing 72 having a top wall 74, a bottom wall 76, two opposite side walls 78, and opposite front and rear walls (not shown), and defining an interior space 80. The housing contains the flow sensing and error signaling subassembly 22 or at least the gas flow sensor 48 thereof, and the power subassembly 28. Apertures equipped with bushings 82 or other securing mechanism known can be in the art can be defined in any wall of the housing 72 to allow portions of the gas flow sensing and error signaling subassembly 22 to protrude from the interior space 80 into the exterior of the housing. Potentially protrusive portions include the gas flow inlet 56, the gas flow outlet 58, the gas flow inlet conduit 30, and the gas flow outlet conduit 32, as illustrated in FIG. 3.

The housing 72 also contains the power subassembly 28 and the indicator subassembly 24. The power subassembly 28 includes a power source 84, preferably including at least one battery 86 enclosed in a battery compartment 88 and mounted in battery clip 90, the battery compartment being attached to any convenient wall of the housing 72. The voltage and capacity of the battery will depend on the number and type of included indicator mechanisms 26 and microcontrollers 104, to be described below. A single nine-volt alkaline battery is suitable many embodiments. Alternative power sources include, but are not limited to, built-in rechargeable NiCD or NiMH batteries, DC current, AC house current delivered via a DC step down transformer (not shown) and a solar cell (not shown). The power subassembly 28 also includes a master power switch 92 to activate and completely inactivate the alarm device 20. The master power switch can include any lever, toggle, or button type known in the art, to completely activate or deactivate the device. The master power switch 92 can be secured by a lock and operated by a lock and key 93, to prevent deactivation of the alarm device 20 by unauthorized personnel. A power light 95, activatable by the master power switch 92, can be included to inform users of the power status of the device 20.

The indicator subassembly 24 includes at least one indicator mechanism 26 operatively connected to the flow sensor and error generator subassembly 22, the indicator mechanism 26 being activatable by an error signal to produce at least one alarm indication perceptible to a user or a device.

Indicator mechanisms 26 can include but are not limited to an audio alarm tone producer 94 such as a bell, a mechanical buzzer, and electronic tone synthesizer. Indicator mechanisms 26 can include a visual display 96 such as an incandescent lamp, a fluorescent tube, a light emitting diode or a liquid crystal display. Indicator mechanisms 26 can include a broadcast signal transmitter 98, defined as a transmitter to communicate an alarm signal to at least one remote receiver 100 to elicit a final alarm indication in the remote receiver. Broadcast signal transmitters 98 can include but are not limited to an radio transmitter broadcasting on AM, FM, or other broadcast radio frequency, to communicate with a radio receiver; a telephone transmitter, to communicate with a telephone receiver via a telephone line or to a cellular phone or pager through a cellular phone network; a wireless local area network (LAN) router to communicate with a computer or other device equipped with a wireless receiver; an Ethernet® router, to communicate with devices on the same wired LAN; a transmitter employing the Bluetooth® protocol to communicate with a cellular phone, printer, or other Bluetooth® equipped device; a closed circuit intercom base station to communicate by wire with an intercom substation; and a signal generator to transmit a signal perceivable by a remote-controlled reservoir-changing device regulator, the signal triggering the reservoir changing device to open a fresh cylinder 10 or other reservoir to the pressurized gas system. The remote control reservoir changing device can be a device provided by the present invention, as will be discussed, or any other suitable device known in the art. The broadcast signal transmitter 98 can include a pilot light 99 to indicate that the transmitter 98 has been activated.

In operation, when the gas flow switch 52 senses a gas flow rate violating a predetermined limit, it closes a circuit to direct current toward at least one of the indicator mechanisms 26, thereby actuating the indicator mechanism 26 to produce an alarm indication. The electrical connections between the power subassembly 28, the flow switch 52, the indicator mechanisms 26, and all additional components described below, are generally defined as connection means 40 in the Figures. It will be understood that particular configurations of connection means such as wiring or printed circuitry will be determined by well known principles of circuit design according to the type of gas flow sensor 48, error signal generator 50, indicator mechanisms 26, and power source 84 selected by a user.

The indicator subassembly 24 can also include a silencing switch 102 whose actuation deactivates at least one activated indicator mechanism 26. The silencing switch 102 permits a user to turn off an alarm indication without having to deactivate the master power of the alarm device 20. The silencing switch 102 can be interposed between an indicator mechanism 26 and the power source, as illustrated in FIG. 1, or it can be situated in any relation to an indicator mechanism 26 that permits deactivation of that indicator mechanism 26. The silencing switch 102 is preferably a key-controlled switch to prevent unauthorized personnel from silencing the indicator mechanism 26. The key control is preferably of the mechanical lock and key type (not shown) but it can alternatively include a more complex system such as a magnetic card and swiper combination. Preferably there is operatively connected to the silencing switch a silencing switch indicator 103, such as a lamp, which is activatable by the activation of the silencing switch 102. The silencing switch indicator 103 reminds a user that an indicator mechanism 26 has been shut off.

The indicators mechanisms 26 and silencing switch 102 can be disposed in any convenient position in the housing 72. Preferably they are visible to a user through suitable apertures or windows in the front wall (not shown) of the housing 72.

Figure 4:
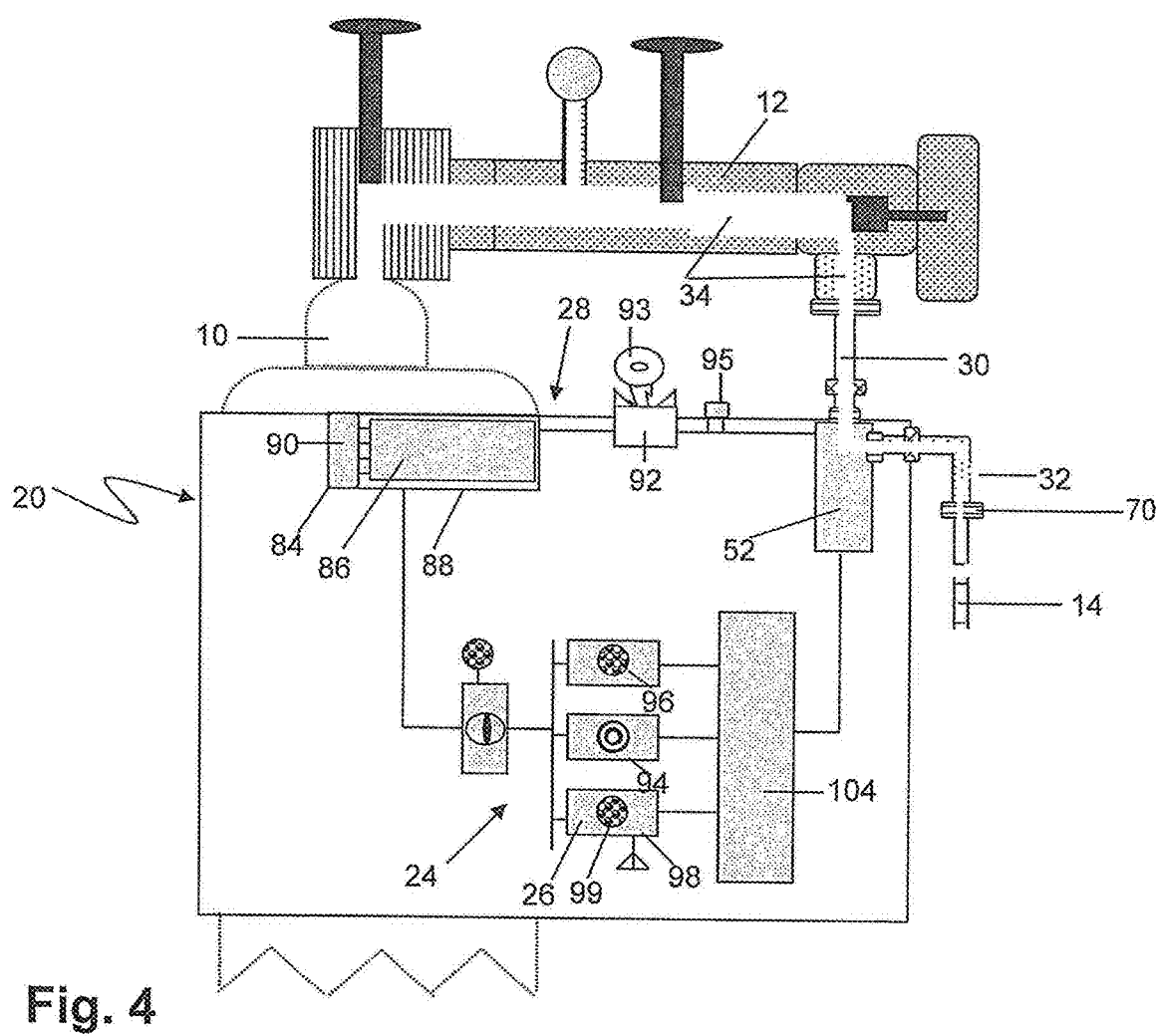
FIG. 4 shows a frontal semi-schematic view of the alarm device including a microcontroller.

The indicator subassembly 24 can also include at least one microcontroller 104 operatively connected to the gas flow switch 52, or other error signal generator 50, and to at least one indicator mechanism 26, as illustrated in FIG. 4. The microcontroller 104 is programmed with at least one routine activatable on receipt of an error signal from the flow switch 52. On activation, the routine commands at least one indicator mechanism 26 to produce an alarm indication. The addition of a microcontroller 104 to the alarm device 20 can add great variety to the alarm indications. The microcontroller 104 can be programmed with routines to vary the sound, frequency pattern, and intermittence of an audio alarm tone producer 94, thereby generating beeps, warbles, synthesized words, and the like. Routines can include commands to a visual display 96 to produce displays such as flashing lights, an ordered display of multiple LED's, or a text message via liquid crystal display. Routines can include commands to a broadcast signal transmitter 98 to transmit to a remote receiver 100 a text or voice message regarding, for example, the location of the pressurized gas system experiencing a gas flow malfunction. In embodiments of the warning device including a gas flow sensor 48 that provides quantitative gas flow data, the microprocessor 104 can include routines that command the digital display of gas flow values. Microcontrollers 104 can be purchased preprogrammed with suitable routines, or can be programmed by the fabricator of the warning device or by the end user. Suitable microcontrollers are available from Maxim Integrated Products, Sunnyvale, Calif.

Figure 5:
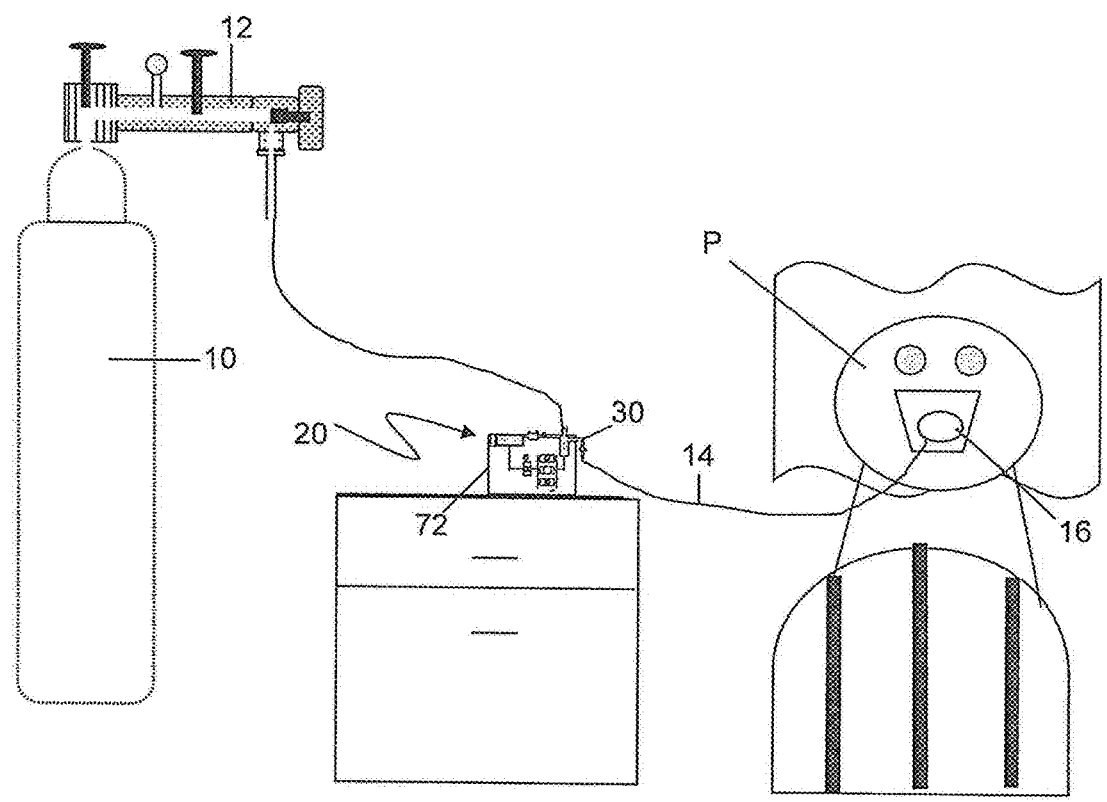
FIG. 5 shows a frontal semi-schematic view of the alarm device situated on a tabletop.

The housing 72 containing the alarm device 20 can be located in any convenient spatial situation relative to the gas cylinder 10 and the end use appliance 16. The housing 72 can for example rest on a table top, situated near the end user, such as an oxygen therapy patient (P), as illustrated in FIG. 5. Alternatively, the housing 72 can be mounted upon a regulator 12 by means of a shelf, a railing, brackets, or chains (not shown). It can be mounted upon an oxygen cylinder, upon the cart of a portable oxygen cylinder, upon a flow meter, or upon a humidifier (not shown). If the warning device 20 is of sufficiently lightweight construction, then the housing 72 can depend from the regulator outlet 64, with its weight supported by the gas flow inlet conduit 30 (not shown). The housing 72 can be incorporated into a gas regulator 12 during fabrication of the regulator (not shown). Hardware and design appropriate for these situations are well known.

Figure 6:
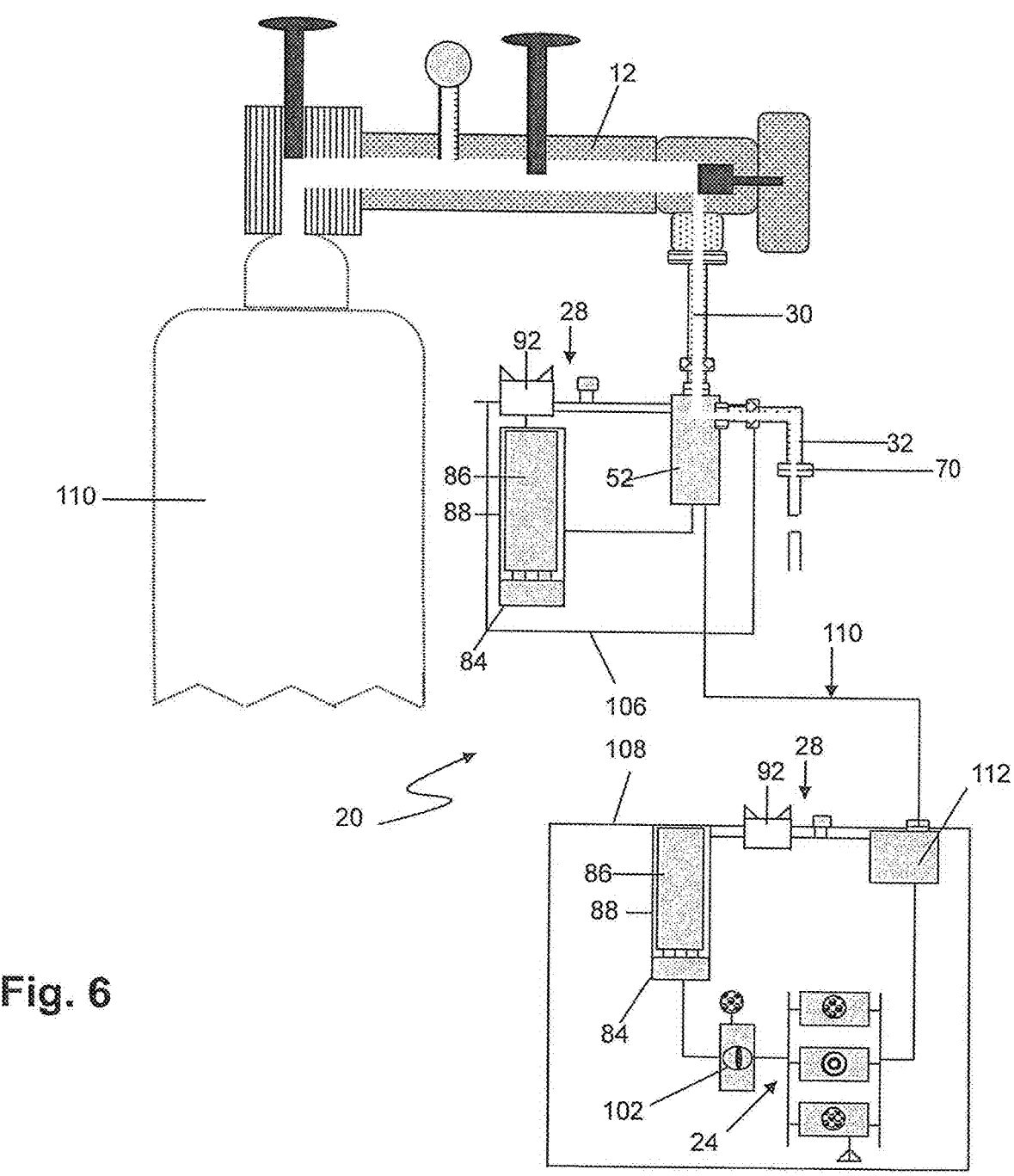
FIG. 6 shows a frontal semi-schematic view of an embodiment of the alarm device housed in a primary and a remote housing, with communication between housings mediated by a wired connection.
Figure 7:
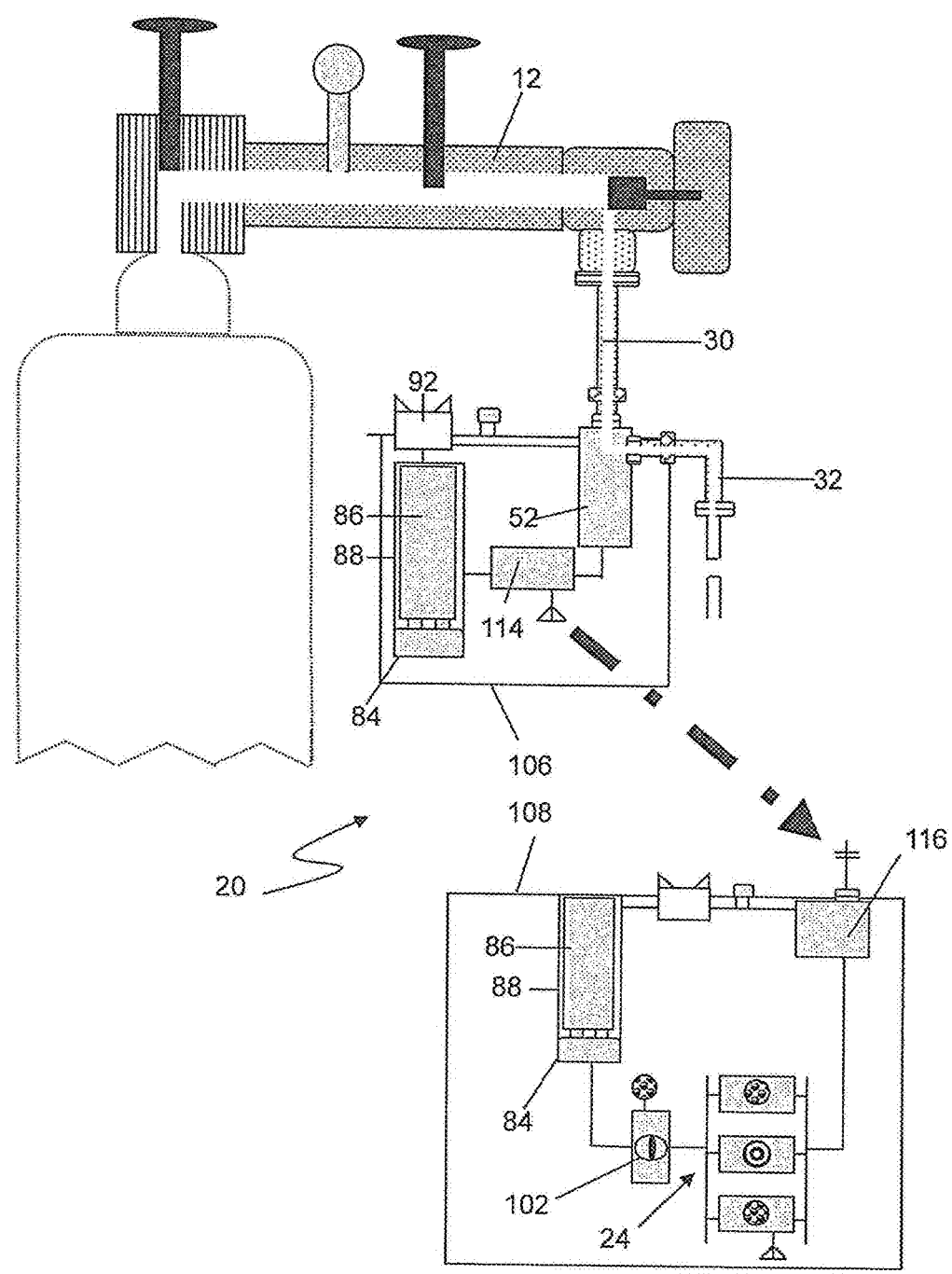
FIG. 7 shows a frontal semi-schematic view of an embodiment of the alarm device contained in a primary and a remote housing, with communication between housings mediated by wireless communication, with the dashed arrow indicating a route of wireless communication.

The present invention can be contained in multiple housings, including a primary housing 106 to contain at least a gas flow sensor 48 and a power subassembly 28, and at least one remote housing 108 to contain at least an indicator subassembly 24. An advantage of a multiple housing configuration is the capability of situating the flow sensing and error signaling subassembly 22, or components thereof, in a primary housing 106 situated in proximity to a gas regulator 12; and situating the indicator subassembly 24 at a site more convenient for monitoring the pressurized gas system. The remote housing 108 can include a separate power system 28 to provide power to the indicator subassembly 24. An example of multiple housing embodiment of the alarm device 20, configured for a medical gas system, is illustrated in FIGS. 6 and 7. The signal from the gas flow switch 52 or other error signal generator (not shown), contained in the primary housing 106, can be conveyed to the indicator subassembly 24, contained in the remote housing 108, by means of a wired connection 110 to the indicator subassembly 24 or to an intermediate receiver 112 in operative connection to the indicator subassembly 24, in the manner of a wired closed circuit intercom or telephone (FIG. 6). Alternatively, the gas flow switch 52 can be operatively connected to a wireless transmitter 114 in the primary housing 106, which conveys a signal via a wireless connection (dashed arrow) to a wireless receiver 116, contained in the remote housing 108, and in operative connection to the indicator subassembly 24 (FIG. 7). Any known transmitting and receiving technology such as AM radio transmission can be utilized to convey the signal.

To provide advance warning of the depletion of a gas in a cylinder 10 or other pressurized reservoir, the warning device 20 can also include a reservoir pressure sensing and pressure error signal generating subassembly to produce an alarm indication when the gas pressure in pressurized reservoir falls below a predetermined limit. The reservoir pressure sensing and pressure error signal generating subassembly is preferably incorporated into a gas pressure switch 124, preferably located upstream of the pressure valve 42 of a regulator 12, where reservoir pressure is most reliably determined. Alternatively, a separate gas reservoir pressure sensor and pressure error signal generator (not shown) in lieu of the gas pressure switch 124.

Figure 8:
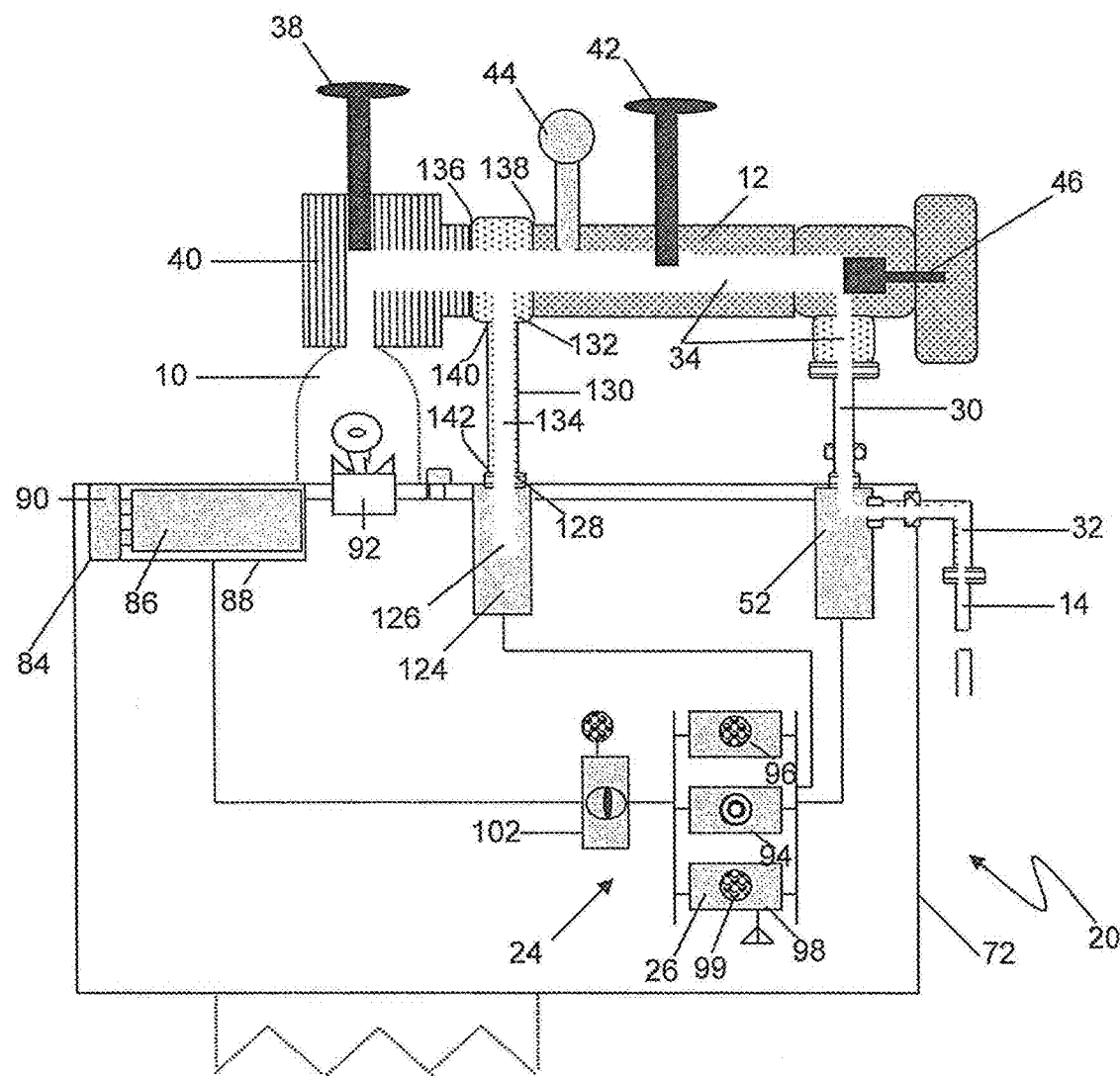
FIG. 8 shows a frontal semi-schematic view of an embodiment of the alarm device additionally including a gas pressure switch.

The addition of reservoir pressure sensing capability can provide earlier warning of the depletion of, for example, a medical oxygen cylinder. An alarm device that senses gas flow malfunctions downstream of the flow valve 46 of a regulator 12 does provide an alarm indication in response to cylinder depletion, but only when depletion has become severe enough to affect gas flow. A gas pressure switch 124 that senses reservoir pressure can be set to generate an error signal before depletion reaches that level of severity. Such a gas pressure switch 124, however, must be situated upstream of the pressure valve 42, where pressure is most reliably sensed, so it is insensitive to malfunctions in the gas line downstream of the flow valve. 46. The combination of a gas pressure switch 124, and a gas flow switch 52, situated as in FIG. 8, provides warning capabilities that cover all possible malfunctions that can afflict a pressurized gas system.

Preferably, the gas pressure switch 124 is a commercial gas pressure switch, most preferably the J205G/J205LG overpressure switch (Whitman Controls Corp, Bristol Conn.), which is of the electronic pressure plate type, and GEMS 3100 pressure series switches (Gems Sensors, Plainville Conn.), which are solid state pressure switches that sense pressure by means of a strain gauge diaphragm. Other types of gas pressure switch can alternatively be included, such as a spring loaded piston switch.

The gas pressure switch 124 includes an internal cavity 126 containing the pressure plate or other sensor mechanism (not shown) and communicating with the pressurized gas system via a gas pressure inlet 128. The gas pressure inlet 128 can be connected to the pressurized gas system by any means of gas-tight engagement known in the art. Preferably the gas pressure switch 124 or other pressure sensor is connected to the pressurized gas system via a gas pressure conduit 130 to expose the gas pressure switch 124 to the internal pressure of the cylinder 10. The gas pressure conduit 130 can be of any form which connects the gas pressure switch 124 in gas-tight engagement with the cylinder 10. In the example illustrated in FIG. 8, the gas pressure conduit 130 includes a tubular adaptor member 132 situated perpendicular to a tubular conduit member 134. The adaptor member 132 intervenes between the cylinder connector 40 and the regulator 12, and includes an upstream orifice 136 in gas-tight engagement with the cylinder connector 40, a downstream orifice 138 parallel to the upstream orifice 136, in gas tight engagement with a regulator 12, and a conduit orifice 140 perpendicular to the upstream and downstream orifices, 136 and 138. The conduit orifice 140 is in gas-tight engagement with the proximal end of the conduit member 134. The distal end of the conduit member 134 includes a sensor orifice 142 in gas tight engagement with the gas pressure inlet 128 of the gas pressure switch 124 or other gas pressure sensor. The gas-tight connections between the gas pressure inlet 128 and the gas pressure conduit 130, and between the gas pressure conduit 130, cylinder connector 40, and regulator 12, are preferably made by complementary screw threaded connections.

Alternatively, the gas pressure switch 125 can be engaged to the pressurized gas system at any point at which cylinder pressure can be accurately sensed. The gas pressure switch can, for example, be incorporated into the cylinder pressure gauge 44.

Figure 9:
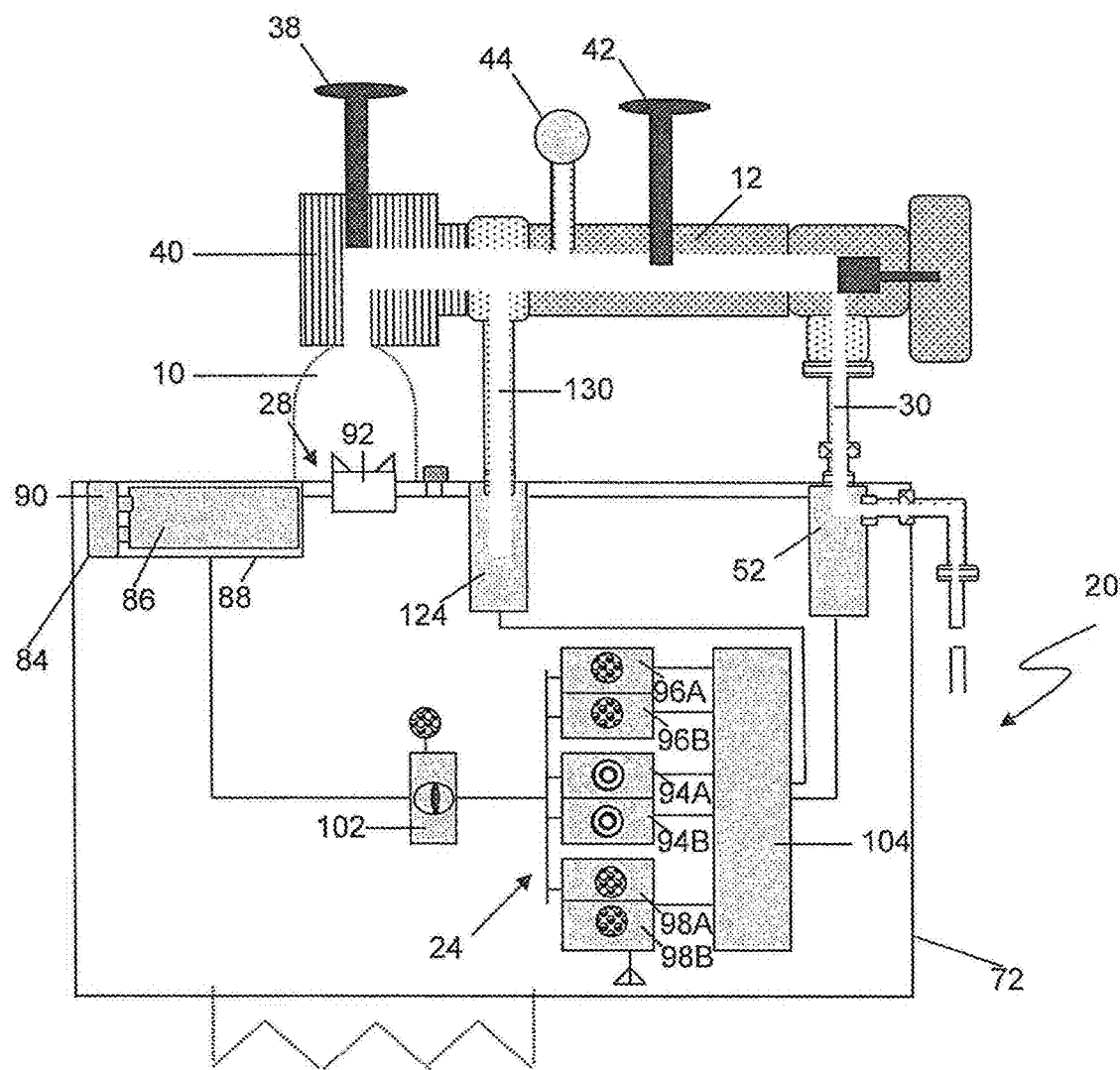
FIG. 9 shows a frontal semi-schematic view of an embodiment of the alarm device including gas pressure switch, and additionally including a microcontroller.

Preferably, the gas pressure switch 124 and gas flow switch 52 are in operative engagement with a common indicator subassembly 24 and a common silencing switch 102, as illustrated in FIGS. 8 and 9. Alternatively, the gas pressure switch 124 is in operative engagement with a separate gas pressure indicator subassembly (not shown). The gas pressure switch 124 can be powered by the same power subassembly 28 as the gas flow switch 52, as illustrated in FIGS. 8 and 9, or it can be powered by a separate power subassembly (not shown). In operation, the gas pressure switch 124, exposed to the gas pressure of the cylinder 10 senses a gas pressure below a predetermined limit and closes a circuit to direct an error signal to at least one of the indicator mechanisms 26 of the indicator subassembly 24, thereby actuating the indicator mechanism 26 to produce an alarm indication. The indicator subassembly 24 can be configured to direct a gas pressure error signal and a gas flow error signal to different indicator mechanisms 26. In this configuration, the alarm device 20 can inform a user whether an alarm indication was triggered by abnormal reservoir pressure or by a gas flow malfunction downstream of the regulator 12. This differential indication is most readily accomplished if a microcontroller 104 is included to issue different gas flow and pressure flow error commands to the indicator subassembly 24, or to route commands to different indicator mechanisms 26, or both. FIG. 9 illustrates an alarm device 20 capable of producing distinctive gas flow pressure alarm indications via gas flow specific indicating devices (94A, audio, 96A, visual, 98A, broadcast), and gas pressure indicating devices alarm indications (devices (94B, audio, 96B, visual, 98B, broadcast).

Figure 10:
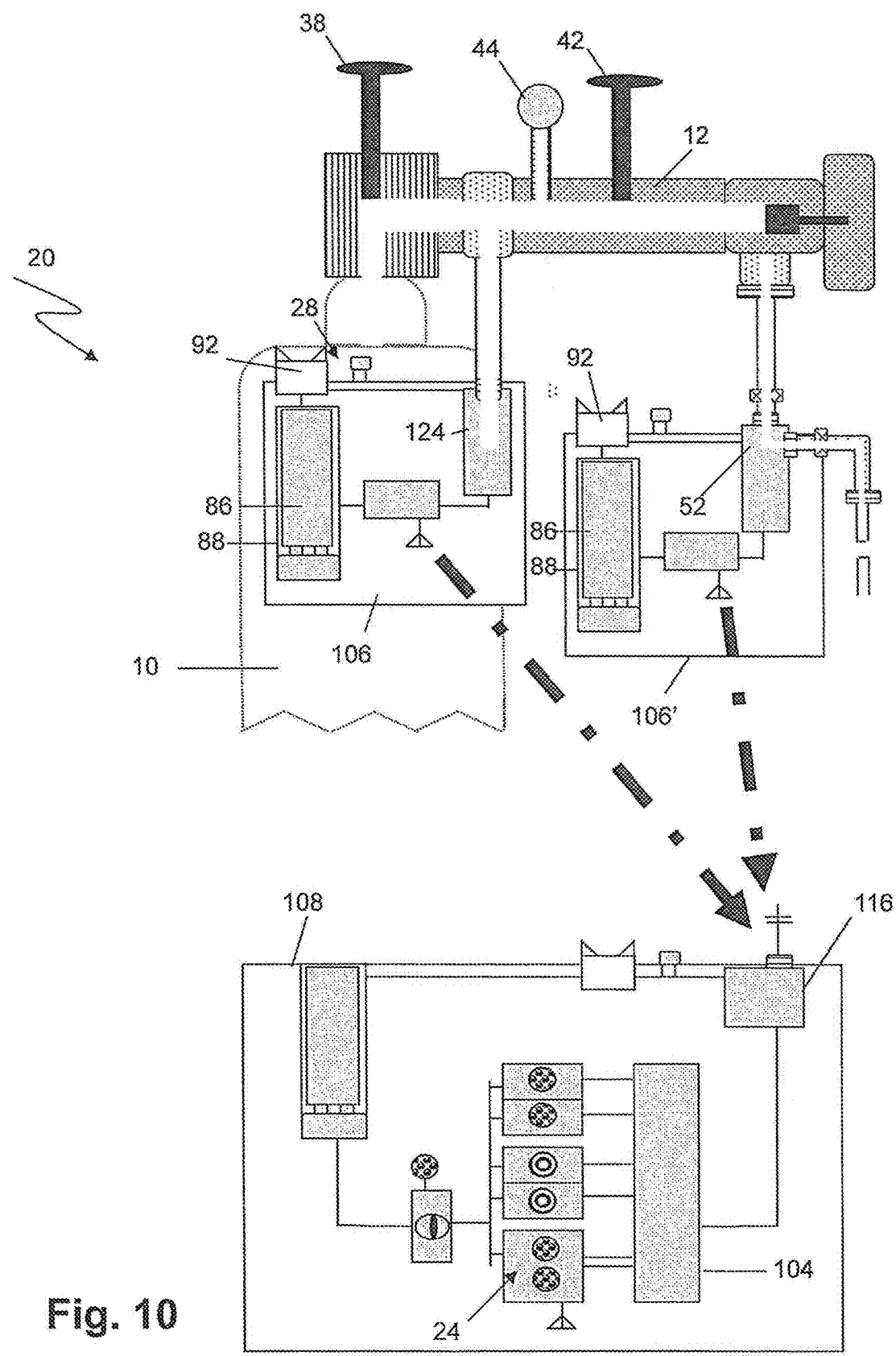
FIG. 10 shows a frontal semi-schematic view of an embodiment of the warning alarm device contained in two primary housings and one remote housing, with communication between primary housings and remote housing mediated by wireless communication, with the dashed arrows indicating a route of wireless communication.

The gas pressure switch 124, or other reservoir pressure sensing and error signal generating subassembly, can be contained in the same housing 72 as the gas flow switch 52, as illustrated in FIGS. 8 and 9. Alternatively, they can be contained in multiple housings. In the example illustrated in FIG. 10, a primary housing 106 contains at least a flow switch 124 and a power subassembly 28. A remote housing 108 contains at least an indicator subassembly 24. Communication between the gas pressure switch 124 and the indicator subassembly 24 can be by wireless broadcast, as illustrated for example in FIG. 10, by wire, or by any suitable form of remote communication, as previously described. Any conceivable combination of primary and remote housings 106, 108 is encompassed by the present invention. In the example illustrated in FIG. 10, a gas pressure switch 124 is included in a first primary housing 106, and a gas flow switch is included in a second primary housing 106', with both switches communicating with a common indicator subassembly 24 in a remote housing 108.

The present invention also includes embodiments including a gas pressure switch 124, or other reservoir pressure sensing and error signal generating subassembly, and not including a gas flow switch 52 or other gas flow sensing and error signal generating subassembly.

Figure 11:
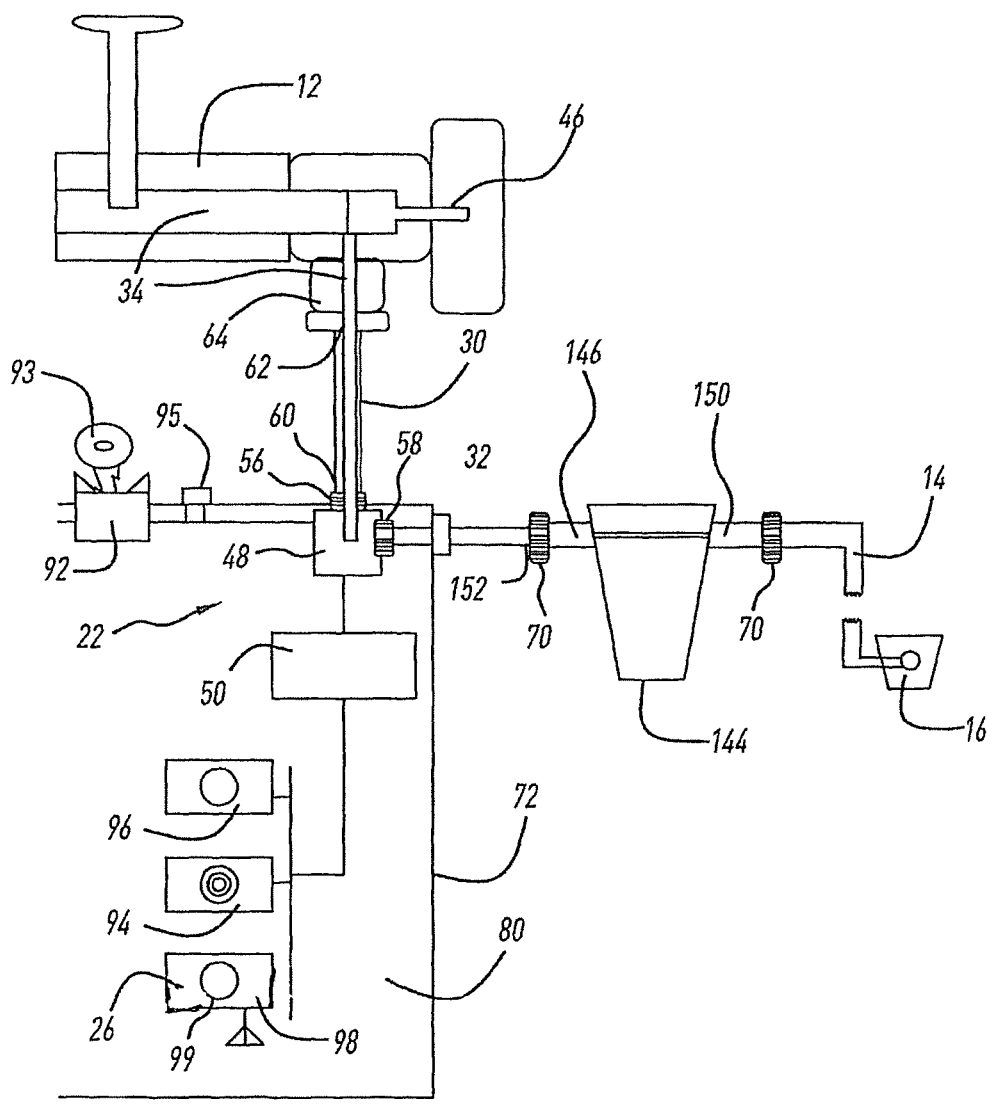
FIG. 11 shows a frontal semi-schematic detail view of an embodiment of the warning alarm device including a downstream accessory device situated externally to the housing of the device.
Figure 12:
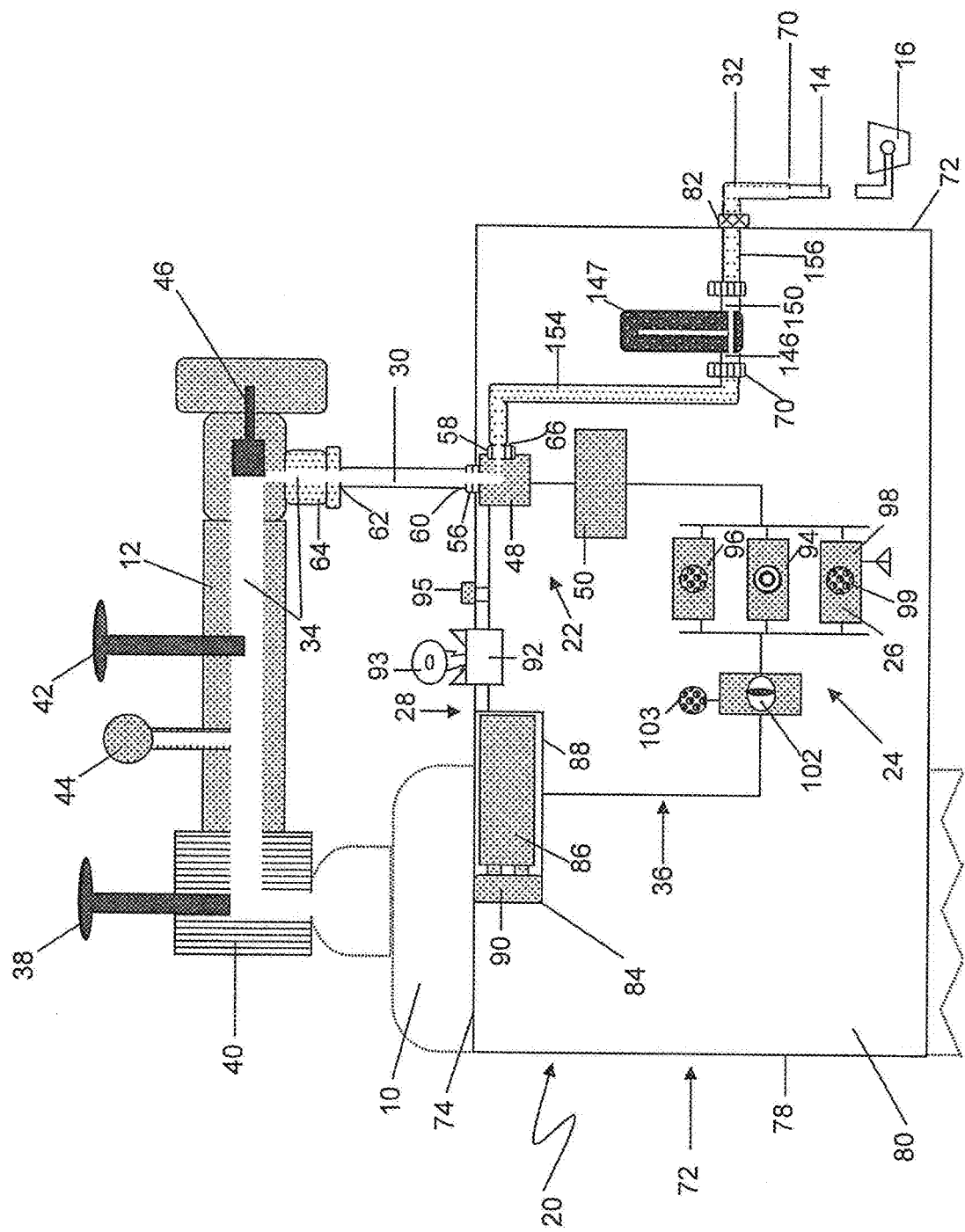
FIG. 12 shows a frontal semi-schematic detail view of the warning alarm device including a downstream accessory device within the housing of the device.

The present invention can additionally include at least one downstream accessory device 144, as illustrated in FIGS. 11 to 14, the downstream accessory device 144 having at least an upstream port 146 in gas-tight engagement with the gas flow outlet conduit 32. For a medical oxygen system, the downstream accessory device 144 can include a filter (not shown), a humidifier (not shown), a flow meter 147, or an oxygen analyzer 148. A downstream accessory device 144 including a filter, humidifier, or flow meter 147 is preferably engaged with the gas flow outlet conduit 32 in a linear relationship, that is, with the entire pressurized gas column 34 passing into the upstream port 146 and out of the downstream port 150 of the downstream accessory device 144, as illustrated in FIG. 11. The upstream port of a downstream accessory device 144 including a filter, humidifier, or flow meter is preferably engaged to a portion of the gas flow outlet conduit 32 external to the housing 72, so that the filter material or humidifier fluid can easily be accessed for replenishment, and the display of the flow meter 147 can easily be observed. For example, a filter or humidifier can be in gas-tight engagement with the distal end 152 of the gas flow outlet conduit 32 by means of any gas-tight connector 70 known in the art, and the downstream port 150 can be in gas-tight engagement with a gas line 14. A downstream accessory device 144 including a flow meter 147 can also be situated external to the housing 72, so that its flow rate display is readily visible to a user. A flow meter 147 can alternatively be situated within the interior space 80 of the housing 72, as illustrated in FIG. 12. In this situation, the gas flow outlet conduit 32 includes a proximal member 154 and a distal member 156. The upstream port 146 of the downstream accessory device 144 is in gas-tight engagement with the proximal member 154 of the gas flow outlet conduit 32, and the downstream port 150 of the downstream accessory device 144 is in gas-tight engagement with the distal member 156 of the gas flow outlet conduit 32. In this situation, the flow rate display of the flow meter 147 can be read by a user through a flow meter window (not shown) defined in any wall of the housing 72.

Figure 13:
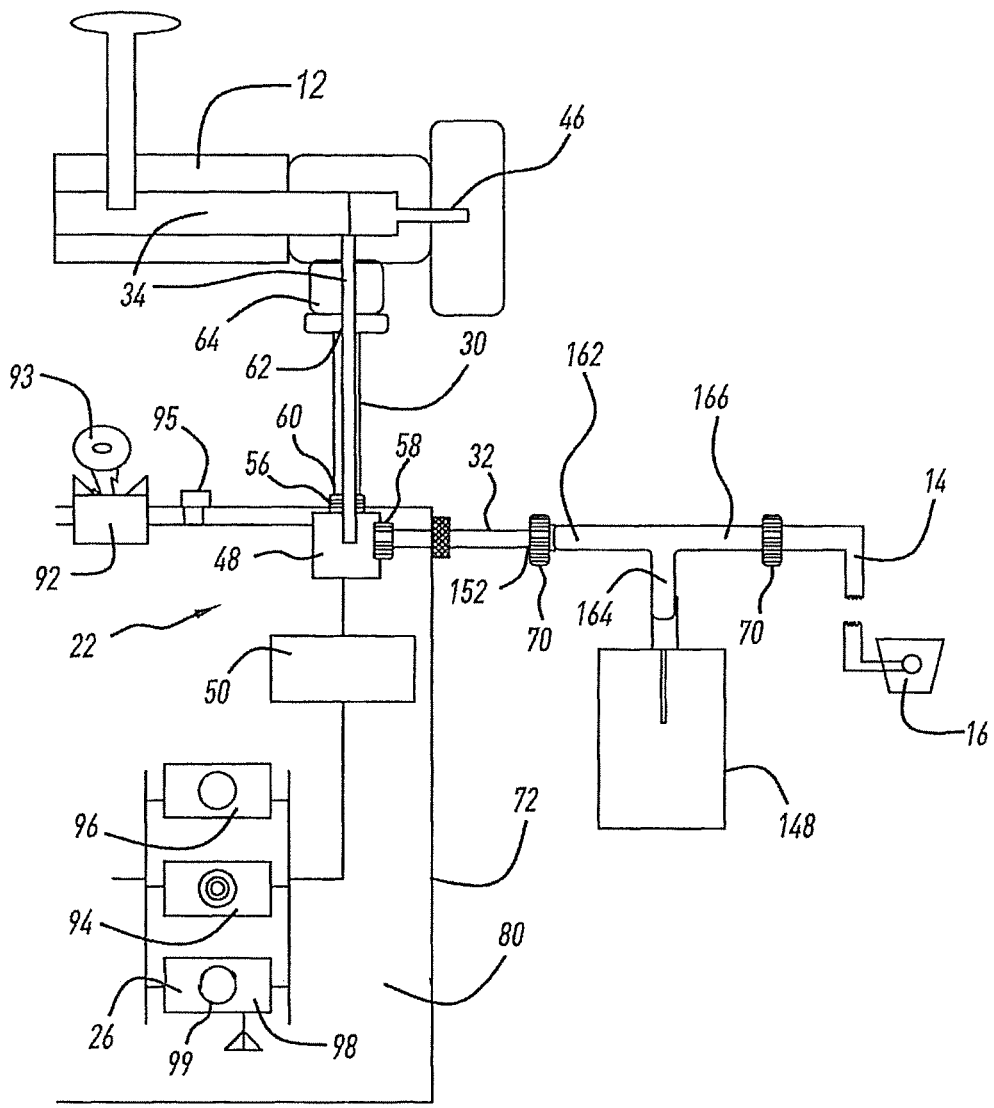
FIG. 13 shows a frontal semi-schematic detail view of the warning alarm device including a downstream oxygen analyzer situated externally to the housing of the device.

A downstream accessory device including an oxygen analyzer 148 having a port 158, the oxygen analyzer 148 is preferably engaged with the gas flow outlet conduit 32 in a bypass relationship, that is, with only a portion of the pressurized gas column 34 passing into the port 158 of the oxygen analyzer 148. As illustrated in FIG. 13, this situation can be achieved by means of a T-shaped connector 160 having an upstream port 162 in gas-tight engagement with the distal end 152 of the gas flow outlet conduit 32, a bypass port 164 in gas-tight engagement with the port 158 of the oxygen analyzer 148 and a downstream port 166 in gas-tight engagement with a gas line 14 or a downstream appliance 16. A valve (not shown) can be included in the bypass port 164 to admit the pressurized gas column 34 into the oxygen analyzer 148 only when desired by a user. The oxygen analyzer 148 and its T-shaped connector 160 can also be contained within the interior space 80 of the housing 72, in a situation similar to that illustrated for the flow meter 147 in FIG. 12.

Figure 14:
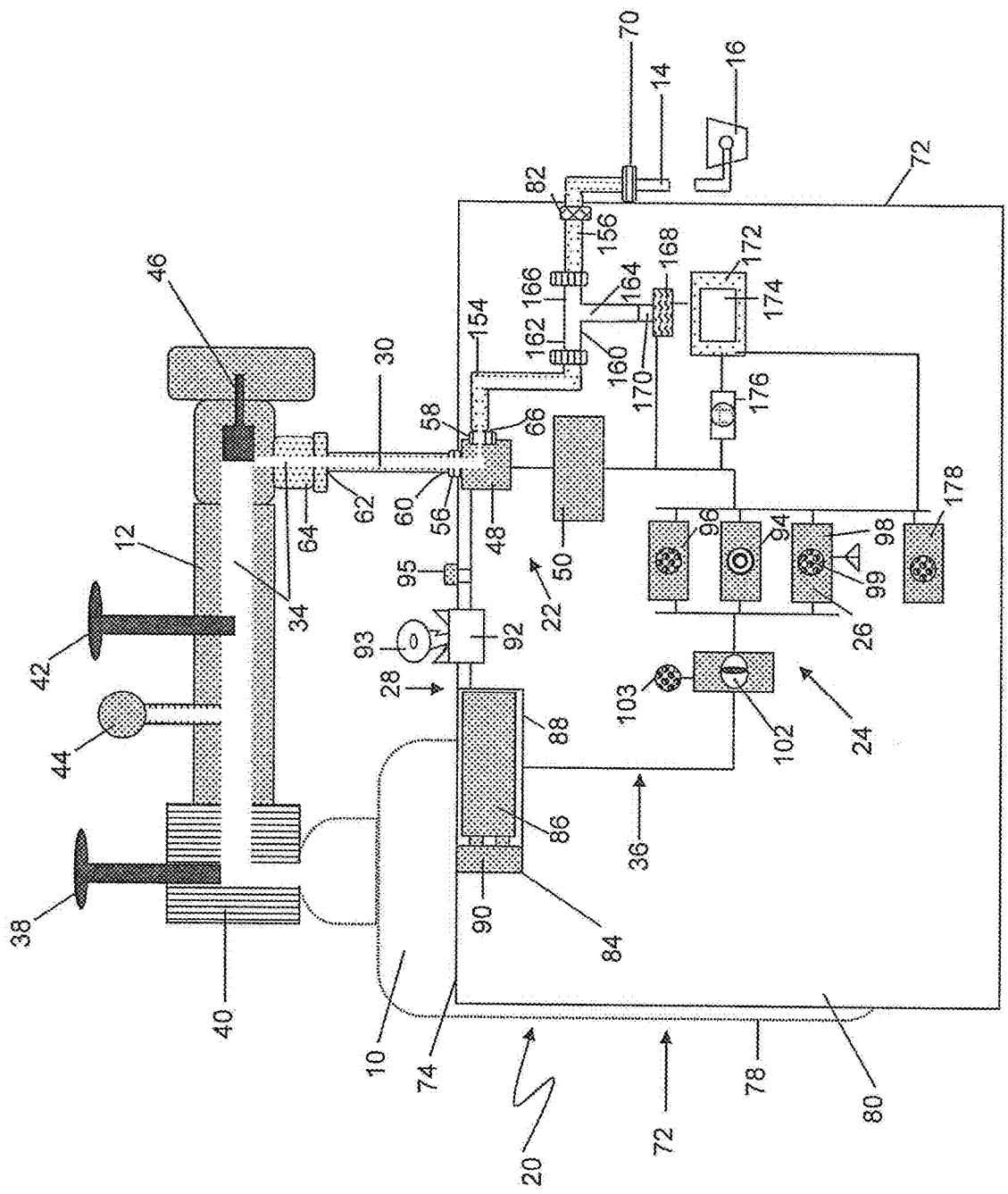
FIG. 14 shows a frontal semi-schematic detail view of the warning alarm device including an oxygen sensor.

Alternatively, the components of an oxygen analyzer can be incorporated directly into the alarm device 20. For example, as illustrated in FIG. 14, an oxygen sensor 168, to sense oxygen content in the pressurized gas stream 34, includes an inlet port 170 in gas-tight engagement with the bypass port 164 of the T shaped connector 160, whose upstream port 162 is in gas-tight engagement with the proximal member 154 of the gas flow outlet conduit 32 and whose downstream port 166 is in gas-tight engagement with the distal member 156 of the gas flow outlet conduit 32. Preferably the oxygen sensor 168 is of the electrogalvanic fuel cell type commonly employed in commercial oxygen analyzers. More preferably the oxygen sensor is a Teledyne R17MED (Teledyne, City of Industry, CA) electrogalvanic fuel cell, although any suitable type or model of oxygen sensor can be incorporated. The oxygen sensor 168, which produces a voltage proportional to the oxygen content of the pressurized gas column 34, is operatively engaged via connection means 36 to a voltmeter 172. The volt meter 172 is configured to measure the voltage produced by the oxygen sensor 168, calculate from that voltage a corresponding value of the percentage of oxygen in the pressurized gas column 34, and display that value on a digital display 174. The volt meter 172 can be calibrated by exposing the oxygen sensor 168 to air and to pure oxygen, in a procedure well known in the art. Air and pure oxygen can be introduced through the upstream orifice 62 of the gas flow inlet conduit 30. The oxygen sensor 168 additionally includes an oxygen sensor on-off button 176 to allow a user to activate the oxygen sensor 168 when a reading is desired. An on-off button aperture (not shown) is defined at any location in the housing 72 adjacent to the oxygen sensor on-off button 176. The oxygen sensor 168 can be anchored to any convenient wall of the housing 72 by suitable brackets or other anchoring means known in the art. As oxygen sensors of the electrogalvanic type become exhausted after many months of use, an oxygen sensor access hatch (not shown) can be included to allow a user to replace the oxygen sensor 168. The oxygen sensor hatch can be defined at any location on the housing 72 adjacent to the oxygen sensor 168.

The voltmeter 172 can additionally be configured to send an error signal to an 02% alarm indicator 178 upon displaying a percent oxygen value below a predetermined limit. The 02% alarm indicator 178 can include an alarm indicator of the audible, visual, or broadcast alarm type.

The present invention can additionally include at least one upstream accessory device (not shown), the upstream accessory device including a flow meter 147 or a humidifier (not shown). The upstream accessory device includes an upstream port (not shown) in gas tight engagement with a source of pressurized gas, and a downstream port (not shown) in gas-tight engagement with the gas flow inlet conduit 30 or with the gas flow inlet 56 of either the gas flow sensor 48 or the gas flow switch 52, the gas tight engagements being made by means of any gas-tight connector known in the art. The source of pressurized gas can include a regulator 12, an oxygen concentrator (not shown), or the outlet of an institutional gas supply (not shown). The downstream accessory device (not shown) can be situated either external or internal to the housing 72.

The present invention also provides a reservoir changing device, generally shown at 180 in FIGS. 15 to 19. The purpose of the reservoir changing device is to open a reserve cylinder 10", or other reserve reservoir of gas to a pressurized gas system upon receiving an alarm indication that pressure in a primary gas cylinder 10', or other primary reservoir, has fallen below a predetermined limit. The alarm indication can include any of the broadcast alarm indications generated by the alarm device 20 of the present invention, including embodiments either including or lacking a gas flow sensor 48 or gas flow switch 52. Alternatively, the alarm indication can be provided by additional or alternative indicator mechanisms (not shown). The reservoir changing device 180 is also useful in pressurized fluid systems other than gas systems.

The reservoir changing device 180 includes an adaptor 182 to connect the device 180 to a gas regulator 12 or other fluid distribution means, at least a first valve member 184 and a second valve member 186, each valve member being in gas-tight engagement with the adaptor 182, and also engageable with a cylinder 10',10" or other gas reservoir. The first and second valve members 184, 186 each include an access valve 190 to control the flow of gas from a cylinder 10',10" into the adaptor 182. In the examples illustrated in FIGS. 15-19, the first valve member 184 is engageable to the primary cylinder 10' and the second valve member 186 is engageable to the reserve cylinder 10". The reservoir changing device 180 additionally includes a motor and transmission subassembly 192 to operate the access valves 190, a power supply 194 to provide power to the motor and transmission subassembly 192; and a control subassembly 196. The control subassembly 196 includes a receiver (not shown) and a motor switch mechanism (not shown), the receiver being capable of receiving an alarm indication and actuating the motor switch mechanism to activate the motor and transmission subassembly 192. The reservoir changing device 180 optionally includes a first adaptor arm 198 and a second adaptor arm 200 to increase the distance between the adaptor 182 and the cylinders 10',10". The first adaptor arm 198 is in gas-tight engagement with both the adaptor 182 and the first valve member 184, and the second adaptor arm 200 is in gas-tight engagement with the adaptor 182 and the second valve member 186.

Figure 15A:
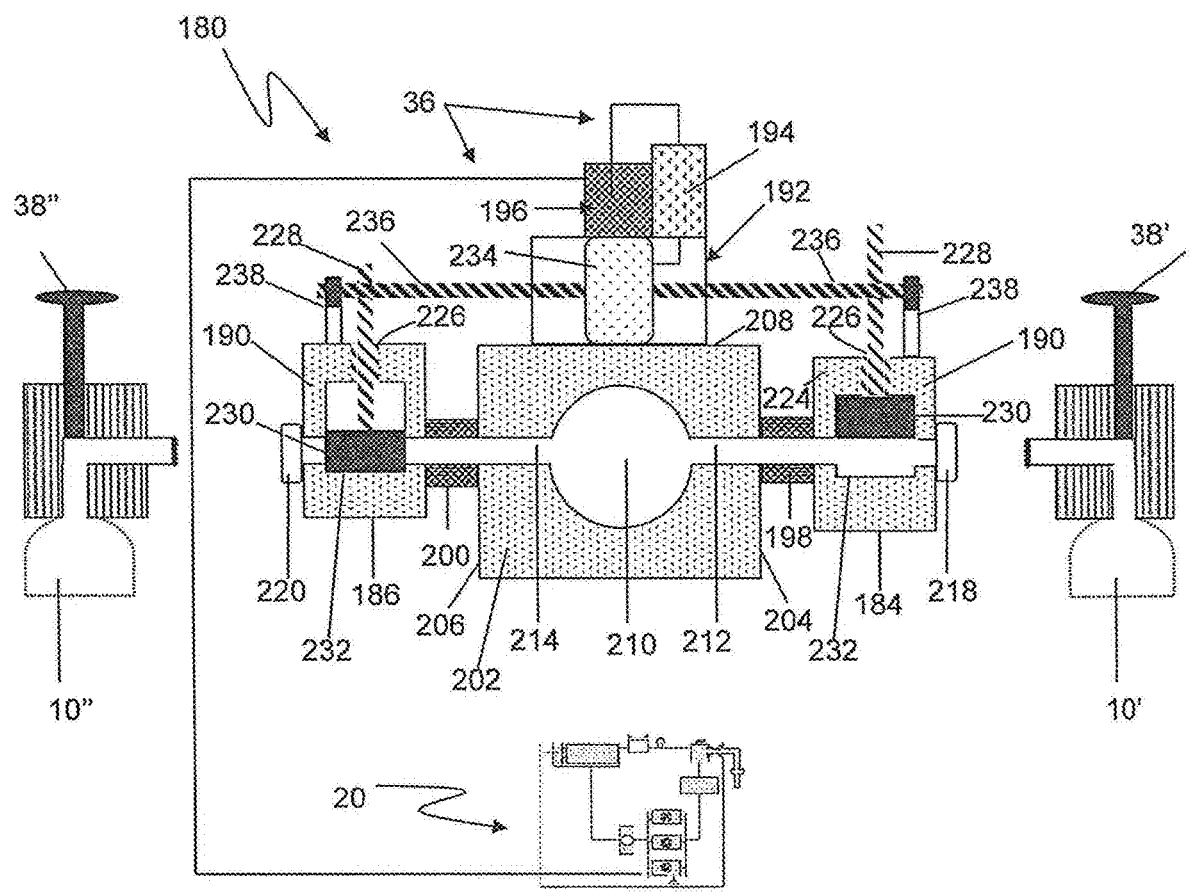
FIG. 15A shows a frontal semi schematic cross section, taken through the center of the adaptor, of an embodiment of the reservoir changing device of the present invention.
Figure 15B:
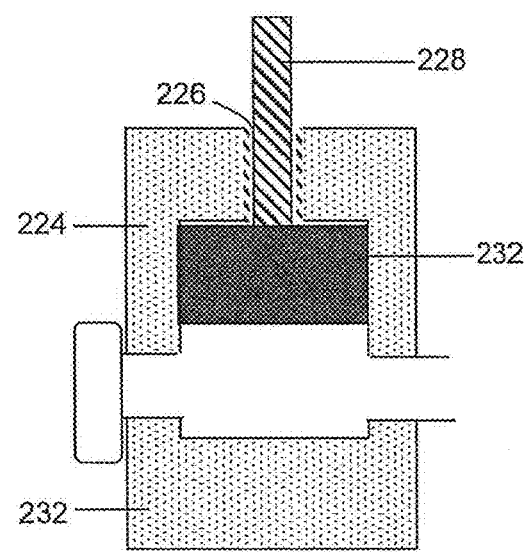
FIG. 15B shows a frontal semi-schematic cross section of a valve member.
Figure 16:
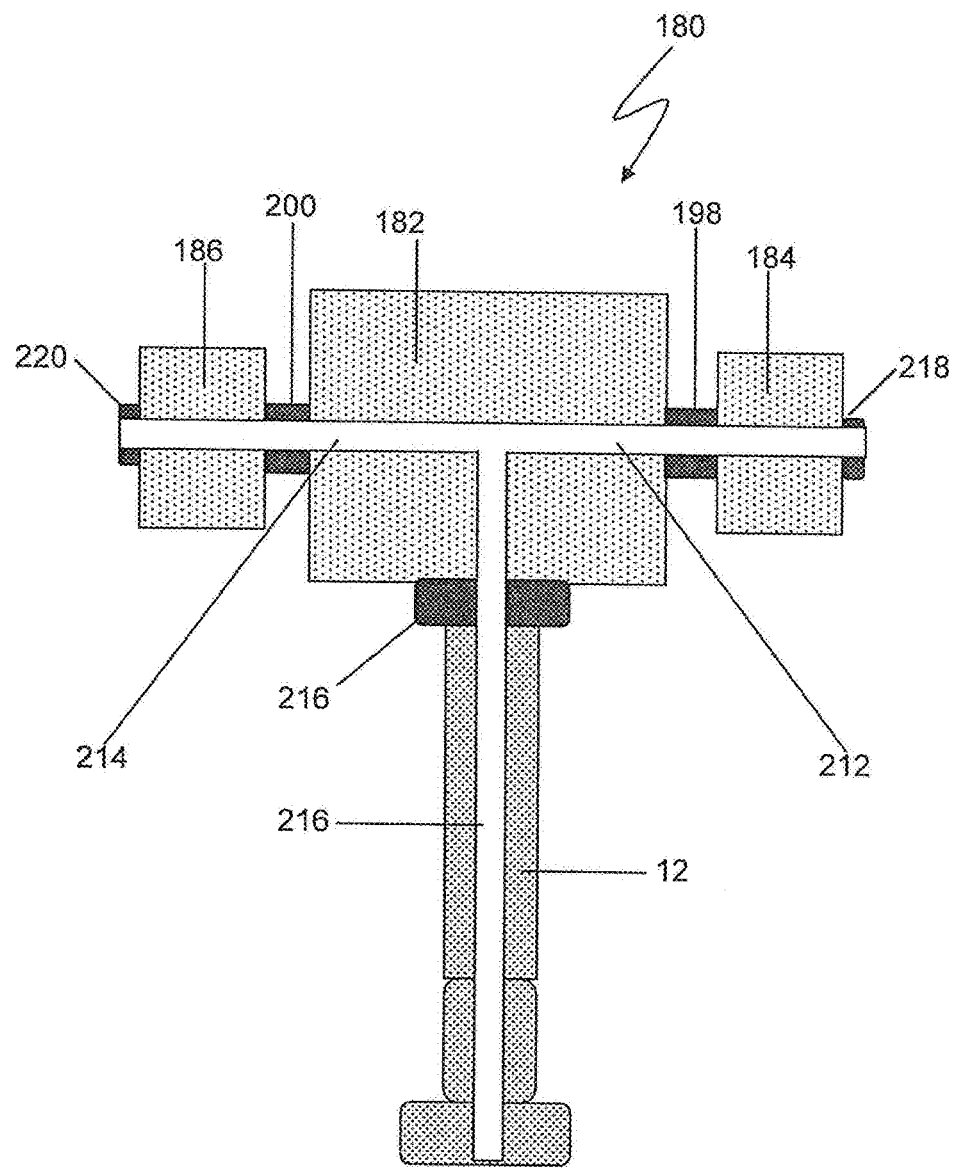
FIG. 16 shows a longitudinal section of the reservoir changing device and an attached regulator.
Figure 17:
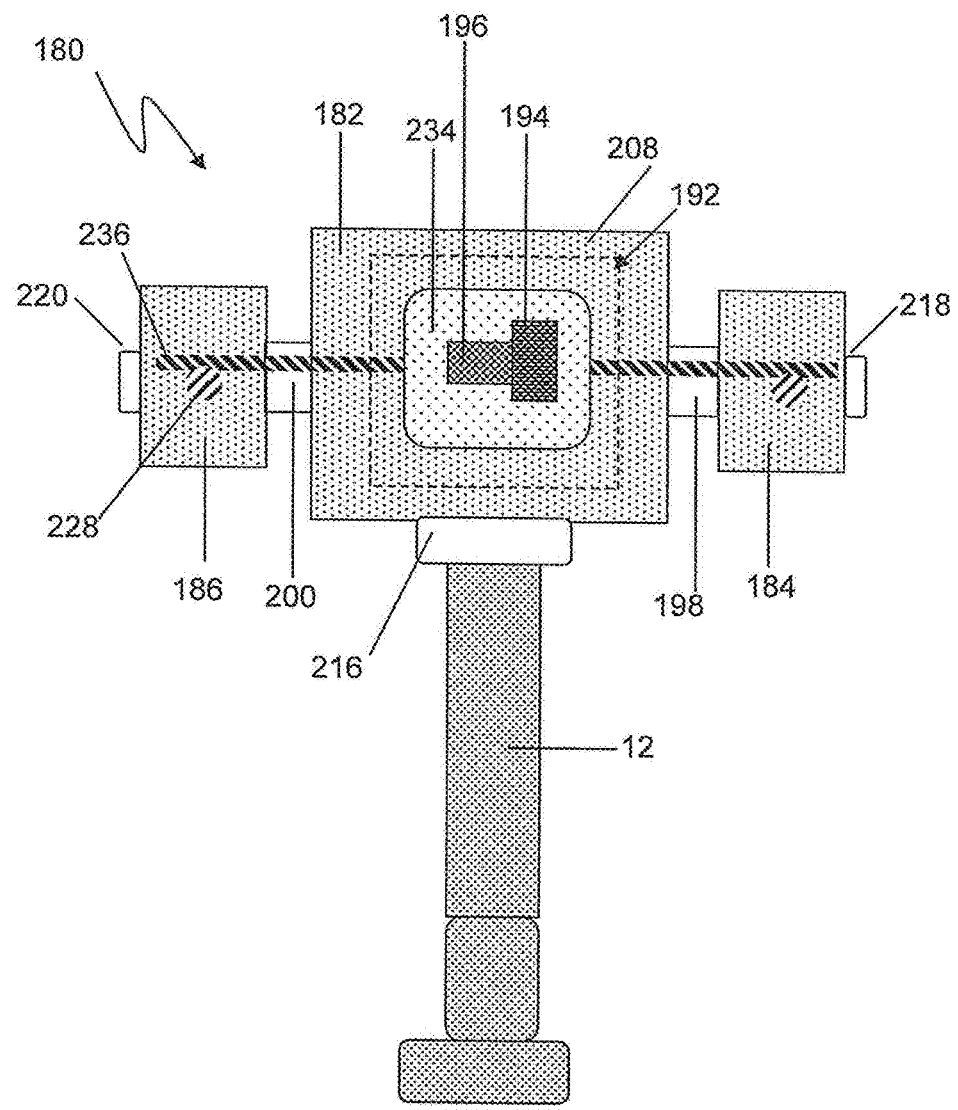
FIG. 17 shows a top elevation of the reservoir changing device and an attached regulator.
Figure 18:
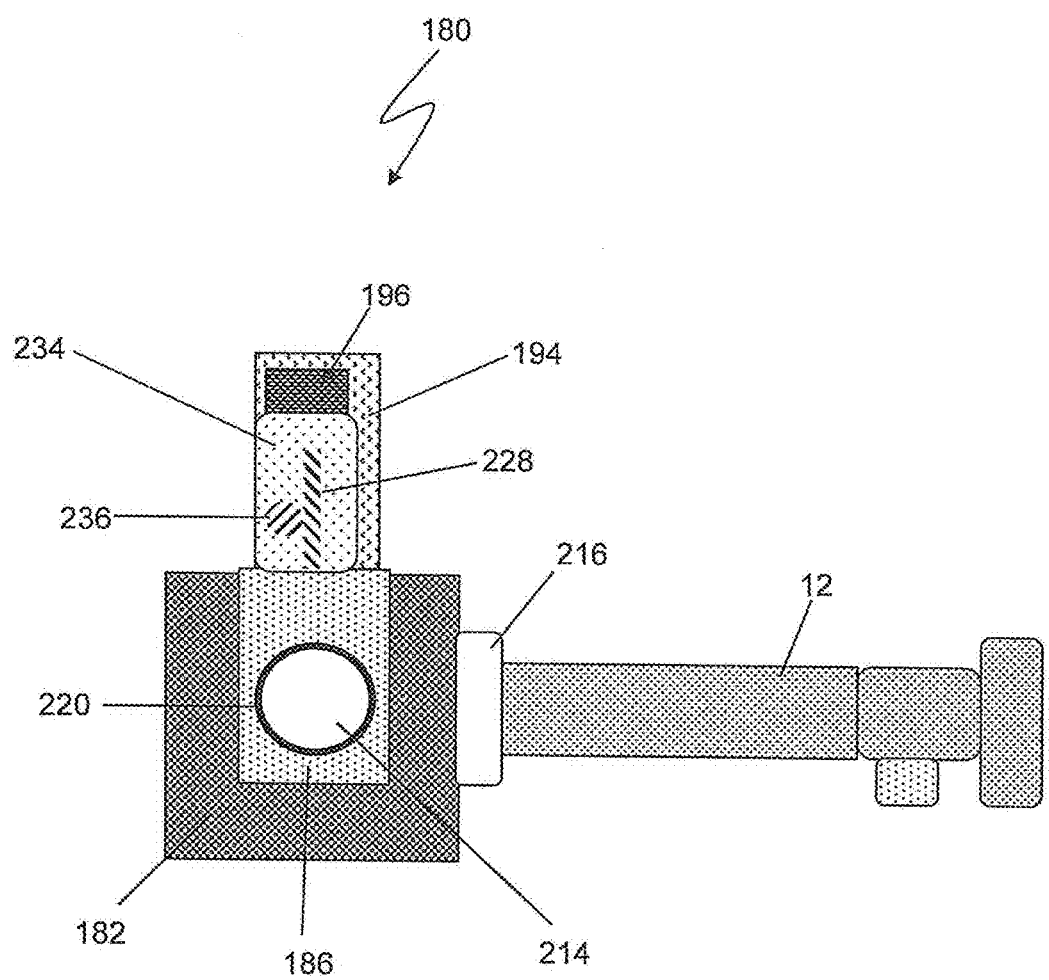
FIG. 18 shows a side elevation of the reservoir changing device and an attached regulator, as viewed from a reserve gas cylinder.
Figure 19:
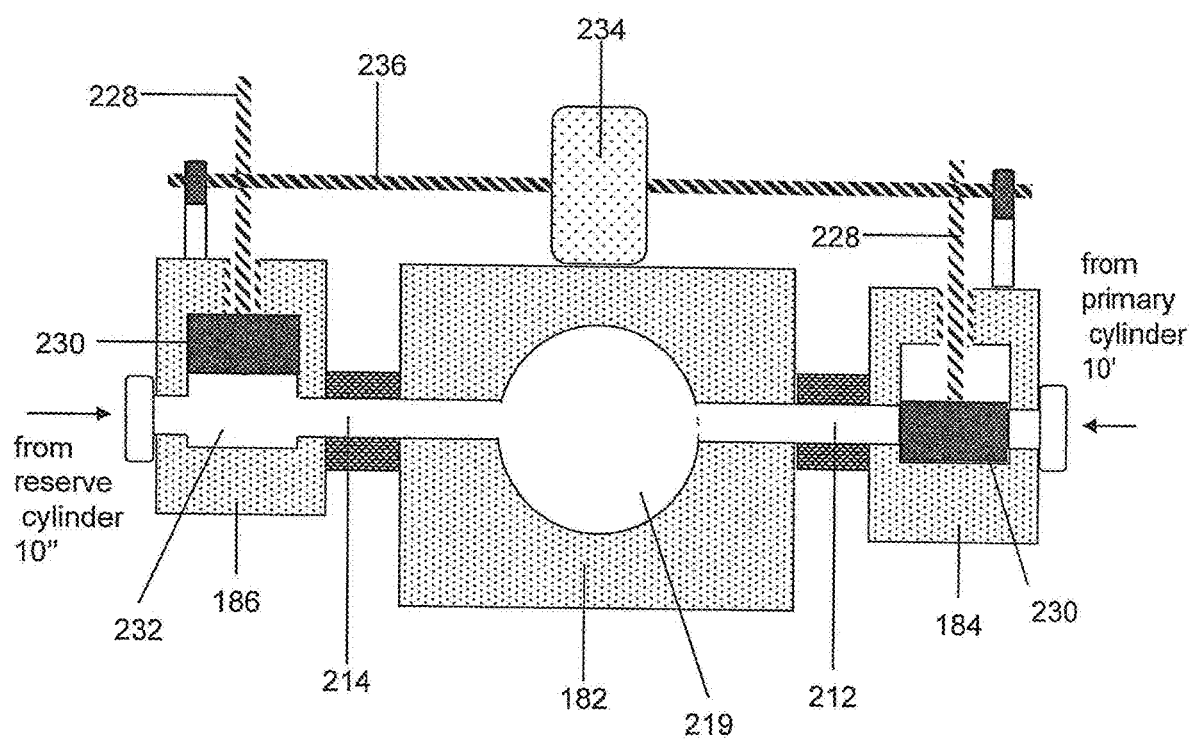
FIG. 19 shows a frontal semi schematic cross section of the access valves of the reservoir changing device, positioned to close a primary gas cylinder and open a reserve gas cylinder to a pressurized gas system.

The adaptor 182 is preferably a rectangular solid having at least a front surface 202, a first side surface 204 opposite a second side surface 206 and a top surface 208. The adaptor 182 defines three intersecting channels extending therethrough, the channels preferably intersecting at a T shaped junction, as best shown in FIG. 16, although Y-shaped junctions and other junction forms can also be included. The channels include a regulator channel 210, a first valve channel 212, and a second valve channel 214. The regulator channel 210 can originate from any point within the adaptor 182, preferably from the center of the adaptor 182, and extends through the front surface 202 to terminate in a regulator port 216, the regulator port 216 being engageable to a gas regulator 12. The first valve channel 212 originates at the regulator channel 210, extends through the first side surface 204 of the adapter 182, and through the first valve member 184, to terminate in a primary reservoir port 218 adapted to engage a primary cylinder 10', or other primary reservoir, in gas-tight engagement. If a first adaptor arm 198 is included, then the first valve channel 212 additionally extends through the first adaptor arm 198. The second valve channel 214 originates at the regulator channel 210 and extends in a direction opposite that of the first valve channel 212, through the second side surface 206 of the adaptor 182, through the second valve member 186, to terminate in a reserve reservoir port 220 adapted to engage a reserve cylinder 10" in gas-tight engagement. The second adaptor arm 200 can also be included in this path, as illustrated in FIGS. 15 and 17. The first and second adaptor arms 198, 200 permit a cylinder 10',10" or other reservoirs to be situated a distance away from the reservoir changing device 180 and regulator 12, the distance being determined by the length of the adaptor arms 198, 200. The primary and reserve reservoir ports 218, 220 can include any adapters known in the art to achieve gas-tight engagement to a particular type of reservoir.

The first and second valve members 184, 186 each include an access valve 190 including a bonnet 224 defining a threaded central bore 226 therethrough, a correspondingly threaded valve stem 228 extending through the central bore 226 and threadingly engaged therewith. The valve stem 228 has an upper end extending through the bonnet 224 and a lower end including a valve body 230. The access valve 190 also includes a valve seat 232, which is continuous with one of the valve channels 212 or 214, and which is complementary in shape to the valve body 230, to sealingly engage the valve body 230 thereby occluding the valve channel 212 or 214 to block the flow of gas from the primary or reserve cylinder 10',10".

The motor and transmission subassembly 192 is preferably situated on the top surface 208 of the adaptor 182. The motor and transmission subassembly 192 includes at least one rotary motor 234, preferably electrically powered, the motor having a motor shaft (not shown) operatively connected to at least one worm gear 236. If the reservoir changing device 180 is intended only to open a reserve cylinder 10" or other reserve reservoir, then only a single worm gear 236 is included, the worm gear 236 extending laterally along the top surface of the adaptor 182, in a direction paralleling the second valve channel 214 to operatively engage the threads of the valve stem 228 of the second valve member 186. Activation of the motor 234 causes the worm gear 236 to rotate to confer counterclockwise motion to the valve stem 228. This causes the valve stem 228 to rise through the central bore 226 of the bonnet 224, lifting the valve body 230 from the valve seat 232, and thereby allowing gas from the reserve cylinder 10" to flow through the second valve channel 214, into the adaptor 182, and hence into the gas regulator 12.

If the reservoir changing device 180 is intended both to open a reserve cylinder 10" and to close a depleted primary cylinder 10', then the device 180 includes two worm gears 236, with a first worm gear 236 engaging the valve stem 228 of the first valve member 184 and a second worm gear 236 engaging the valve stem 228 of the second valve member 186. Preferably both worm gears 236 are operatively connected to a single motor 234, the worm gears 236 being threaded in complementary directions, with a first worm gear 236 lifting the valve stem 228 of the second valve member 186 to allow gas from the reserve cylinder 10" to flow into the adaptor 182, and the second worm gear 236 simultaneously lowering the valve stem 228 of the first valve member 184, to close the primary cylinder 10' off from the adaptor 182. It is desirable to close the depleted primary cylinder 10' in order to prevent gas from the reserve cylinder 10" from being wastefully diverted into the depleted primary cylinder 10'.

The device 180 can include at least one worm gear stabilizer, for example worm gear guide 238, to stabilize the worm gear 236 during its rotation. The worm gear guide 238 includes a bracket extending from a valve bonnet 224 to pivotingly engage the worm gear 236.

Preferably, a clutch (not shown) or other means to disengage the motor 234 from the worm gear 236 is additionally included in the power and transmission subassembly 192. Disengagement of the worm gear 236 from the motor 234 permits a user to manually open or close an access valve 190 in order to prepare the device 180 for use. To further facilitate manual operation of an access valve, the valve stem 228 can additionally include a handle (not shown) for manual rotation of a valve stem 228 within the central bore 226 of a bonnet 234.

The materials employed in the reservoir changing device 180 are selected according to the nature of the gas in the pressurized gas system, and to the level of pressure to which it will be exposed. In general, any materials suitable for the reservoir itself, and for its valves and fittings, will also be suitable for use in the device 180.

The motor 234 can include motors of any type, size, speed, power output, and power source appropriate to the size and weight of the access valves 190. It is preferable to include a motor 234 with sufficiently high initial torque to overcome the inertia of the valve stem 228, and with relatively low speed and high torque, as power to firmly seat the valve body 230 is more important than speed of movement. It is also preferable to provide the motor 234 with a shut-off mechanism (not shown) to deactivate the motor 234 when the valve body 230 has reached the end of its travel. Travel limit sensors and torque limit sensors that will cut off power to the motor are well known in the art.

The reservoir changing device 180 can alternatively include any motive force and any valve operation means that will appropriately open and close access valves 190. For example, an individual motor 234 can be operatively connected directly to each valve stem, to supply torque directly to the valve stem (not shown). Valves can alternatively be opened and closed by means of springs (not shown) actuated by the control subassembly 196. Spring powered valves are feasible for low pressure reservoirs such as portable liquid propane tanks.

The power supply 194 is selected according to the characteristics of the motor. Preferably the power supply 194 includes a battery with sufficient power and capacity to meet the demands of the selected motor 234. Battery power insulates the reservoir changing device 180 from interruptions in house current, and permits use of the device 180 in the field. For greater demands, alternative power sources include, but are not limited to, DC and AC house current.

The control subassembly 196 can be situated in any location from which it can actuate the motor 234. The control subassembly includes a master on-off switch (not shown) to permit a user to activate and deactivate the reservoir changing device 180, and a motor switch (not shown) to activate and deactivate the motor 234. The control subassembly 196 additionally includes a receiver (not shown) to receive an alarm indication that the gas pressure in the primary cylinder 10' has diminished to a predetermined level. The receiver can be any device capable of receiving wired or wireless broadcast alarm indications and actuating a motor switch to activate the motor 234. Receivers can include, but are not limited to, a radio receiver; a wired or cellular phone receiver, a pager, a receiving device on a wired or wireless LAN, a Bluetooth® equipped device, and a wired intercom substation. The control subassembly 196 optionally includes a manual operation switch (not shown) to permit a user to manually activate the motor 234 in order to move the valves into desired positions. In the example illustrated in FIG. 15, the control subassembly 196 is operatively connected to the alarm device 20, and to the motor 234, by connection means 36 such as wiring, printed circuits, and the like.

In operation, the initial condition of the reservoir changing device is as illustrated in FIG. 15, with the access valve 190 of the first valve member 184 in raised, open position, and the access valve of the second valve member 186 in closed position. A user engages a regulator 12 to the regulator port 216. The user engages a primary cylinder 10' or other primary reservoir with the primary reservoir port 218, and a reserve cylinder 10" to the reserve reservoir port 220. The user opens the main valve 38' of the primary cylinder 10' and the main valve 38" of the reserve cylinder 10". A stream of pressurized gas flows from the primary cylinder 10', through the first valve channel 212 and the regulator channel 210, and into the regulator 12. The user operates the master power switch (not shown) to activate the reservoir changing device 180. The user activates the alarm device 20 or any other alarm indicator operatively connected to the reservoir changing device 180. When pressure in the primary cylinder 10' reaches a predetermined level, an alarm indication is received by the receiver (not shown) of the control subassembly 196. The receiver actuates the motor switch (not shown) to activate the motor 234 to rotate the worm gears 236, thereby opening the access valve 190 of the second valve member 186 and closing the access valve 190 of the first valve member 184, to achieve the final state illustrated in FIG. 19. In the final state, the stream of pressurized gas flows from the reserve cylinder 10", through the second valve channel 214 and the regulator channel 210 and into the regulator 12. The primary cylinder 10' is closed off from the pressurized gas system.

An advantage of the reservoir changing device 180 is that it can be made in any size, and combined with any fittings, to be applicable to any combination of reservoirs and regulator. Another advantage is that the reservoirs need not be closely adjacent to the regulator 12, as the first and second adaptor arms 198, 200 can be extended to any desired length. This allows flexibility in reservoir arrangement. The reservoir changing device 180 can also be readily adapted to accept and control more than one reserve reservoir by the inclusion of additional valve members.

Another embodiment of the present invention, a gas supply warning and communication system 250, provides capabilities for communicating and storing error alarm signals, gas pressure and gas flow data and system status information. The system 250 also provides a motorized reservoir changeover device 252 optionally including a universal valve coupler 254 for automatically opening the valves of reserve gas reservoirs of any size and shape in the event of a gas system malfunction.

Figure 20:
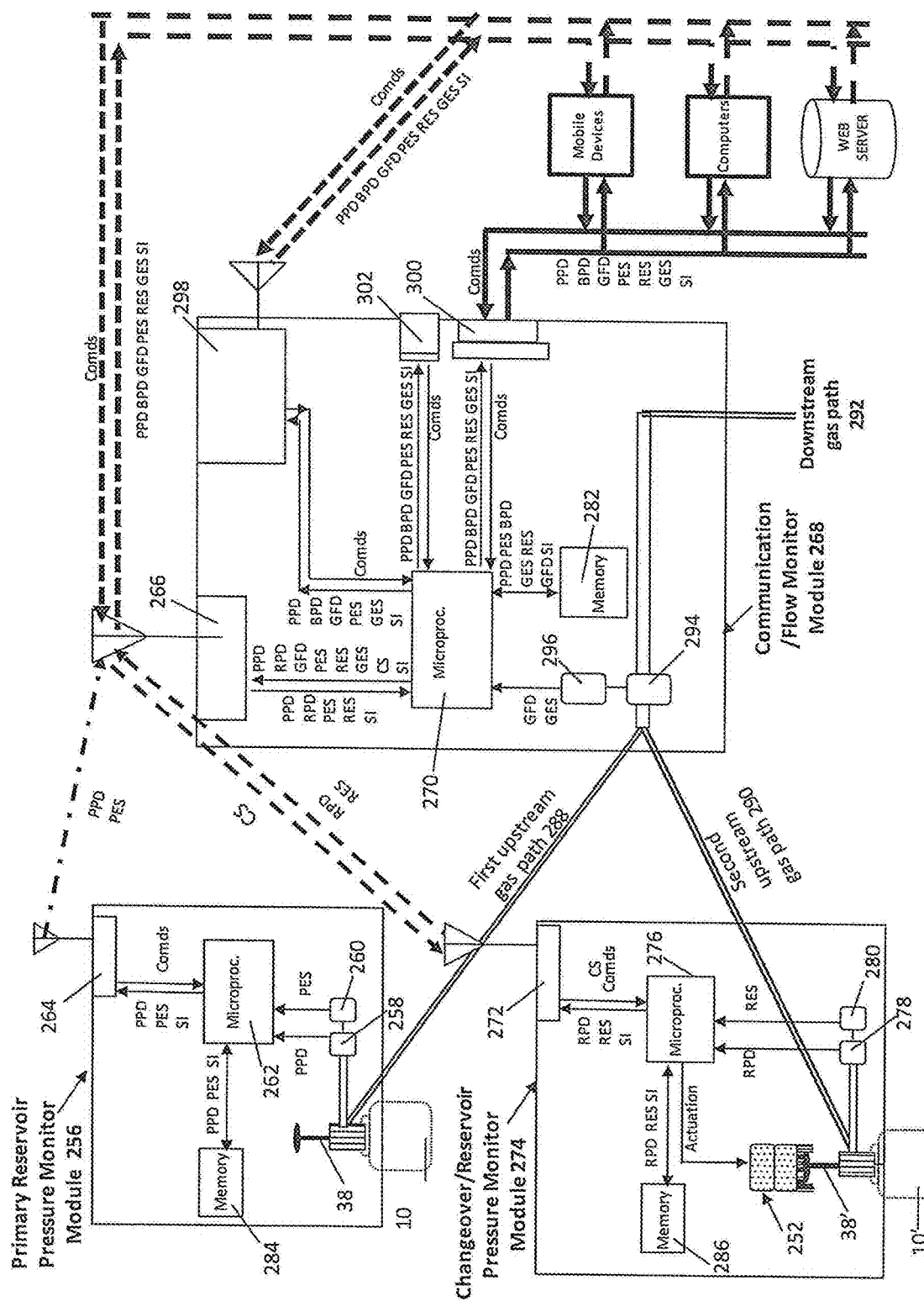
FIG. 20 shows a semi-schematic overview of the structure, operation, and information flow in a gas supply warning, communication, and changeover system according to the present invention.

An overview of the structure, operation, and information flow of the gas supply warning and communication system 250 is shown in FIG. 20. Information flow is indicated by arrows labeled with abbreviated identifications of particular types of information.

The system 250 accommodates at least one primary gas reservoir, such as the primary gas cylinder 10, which directs a flow of gas into a first upstream gas path 288; and at least one secondary gas reservoir, such as reserve gas cylinder 10', which directs a flow of gas into a second upstream gas path 290. Both the first and second upstream gas paths eventually converge into a single downstream gas path 292 towards accessories and end use appliances (not shown in FIG. 20), which were described previously.

The system 250 includes a primary reservoir pressure monitor module 256, which monitors the gas pressure of the primary cylinder 10 by means of a primary reservoir pressure sensor 258, which generates digital primary reservoir gas pressure data (PPD in FIG. 20). The primary reservoir pressure monitor module 256 also includes a primary reservoir pressure error signal generator 260, operatively connected to the primary reservoir pressure sensor 258. The primary reservoir pressure error signal generator 260 generates a primary reservoir pressure error signal (PES in FIG. 20) when the primary reservoir pressure sensor 260 detects a reservoir pressure that violates a predetermined limit. The primary reservoir pressure error signal is received by a pressure monitor microprocessor 262, which routes it to a pressure monitor transceiver 264 for transmission to a central transceiver 266 situated at a communication/flow monitor module 268. There, the primary reservoir pressure error signal is received by a central microprocessor 270, which responds by generating a reservoir changeover signal (CS). The central microprocessor 270 routes the changeover signal to the central transceiver 266 for transmission to a changeover transceiver 272 situated at a changeover/reservoir pressure monitor module 274. The changeover/reservoir pressure monitor module 274 is engaged to a reserve gas reservoir such as a reserve gas cylinder 10'.

The changeover signal, received at the changeover/reservoir pressure monitor module 274, is conveyed to a changeover/pressure monitor microprocessor 276, which responds by actuating the motorized reservoir changeover device 252, which is engaged to the main valve 38' of the reserve gas cylinder 10'. Upon actuation, the motorized reservoir changeover device 252 opens the reserve gas cylinder to the second upstream gas path 290 leading to the communications/flow monitor module 268.

Preferably, the changeover/pressure monitor module 274 also has the capability of monitoring the pressure of the reserve gas cylinder 10' after it has been opened. For this purpose, the changeover/pressure monitor module 274 includes a reserve reservoir pressure sensor 278 to generate reserve reservoir pressure data (RPD). The reserve reservoir pressure sensor 278 is operatively connected to a reserve reservoir pressure error signal generator 280 for generating reserve reservoir pressure error signals (RES). The reserve reservoir pressure sensor 278 and the reserve reservoir pressure error signal generator 280 are operatively connected to the changeover/pressure monitor microprocessor 276. Both the reserve reservoir pressure data and reserve reservoir pressure error signals are routed by the changeover/pressure monitor microprocessor 276 to the changeover transceiver 282, for transmission to the communications/flow monitor module 268.

The reservoir gas pressure data, pressure error signals, and changeover signals are all recorded as event records in a central event memory 282 situated in the communications/flow monitor module 268. An event record is defined as an electronic record including at least the identity of an event, and the date and time of its occurrence. In the present invention, an event can have an identity including but not limited to, a gas pressure value, a gas flow rate value, on oxygen concentration value, the transmission or reception of a pressure error signal or a gas flow rate error, a command (COMD) from a remote user, and a status indication (SI) regarding a function of the system 250, such as the activation or deactivation of electrical power. The identity of a user connected to the system 250 can be associated with each event record relevant to that user.

Preferably, there is at least transient storage of event records at the primary reservoir pressure monitor module 256, and at the changeover/reservoir pressure monitor module 274, in, respectively, a pressure monitor event memory 284 and a changeover/pressure event memory 286. This transient storage is useful if communication between modules is intermittent.

The communications/flow module 268, in addition to its previously described communication and storage functions, also monitors the gas flow from the first upstream path 288 leading to the primary gas cylinder 10, the second upstream path 290 leading from the reserve gas cylinder 10', and as many additional upstream paths to additional gas reservoirs (not shown) as desired. For this purpose, the communications/flow module 268 includes a gas flow sensor 294 and a gas flow error signal generator 296, both of which are operatively connected to the central microprocessor 270. The gas flow sensor 294 generates gas flow data (GFD) and the gas flow error signal generator 296 generates gas flow error signals (GES), which are routed to the central event memory 282 by the central microprocessor 270. The central microprocessor 270 can also be configured to generate a changeover signal in response to the receipt of a gas flow error signal. In this configuration, the system 250 opens the reserve gas cylinder 10' in response to a gas flow malfunction, such as a blockage or disconnection of a gas line.

In the preferred embodiment, status indications (SI) regarding system history and function are received by the central microprocessor 270, which routes them to the central event memory 282 for storage.

The primary reservoir pressure monitor module 256, the changeover/reservoir pressure monitor module 274, and the communications/flow module 268 optionally include digital gas pressure or gas flow rate data displays, and gas pressure and gas flow error alarm indicators, which are not shown in FIG. 20 and will be described in detail below.

It will be understood that an unlimited number of primary reservoir pressure monitor modules 256 and changeover/reservoir pressure monitor modules 274, can be operatively connected to a communications/flow module 268, with each module 256, 274 having a unique identifier and each module 256, 274 being independently controlled through the changeover/reservoir pressure monitor module 274.

Event records stored in the central event memory 270 are accessible by users of remote devices by multiple means of data transfer. The communication/flow monitor module 268 includes a telephonic module 298 for access of records by mobile devices, land line phones, and web and local network servers. Event records are also accessible by wireless radiofrequency (RF) transmission via the central transceiver 266, by any device equipped with a compatible wireless modem. A cable port 300 permits downloading of event records by a cabled connection to one or more remote devices, including but not limited to computers, such as personal computers (PC), tablets, and servers such as local network servers and web servers, via USB, serial or Ethernet cable, Event records are also downloadable from the central event memory 270 into a removable storage device, such as an SD card or a USB flash drive, via a compatible storage device socket 302. Downloading of data can be accomplished automatically, at regular intervals, or by manual command through one of the remote devices.

The central microprocessor 270 can also receive control commands (COMDS in FIG. 20) entered into any of the previously mentioned remote devices. Commands can also be input into user input buttons 303 (FIGS. 27A-27D). The input buttons 303 are located on display panels (not shown) which serve as user interfaces at the primary reservoir pressure monitor module 256, the communication/flow monitor module 268, and the changeover/reservoir pressure monitor module 274. Users can input commands, for example, to silence an alarm indication, to power or depower a module, to specify a setting such as an alarm threshold setting, to energize or de-energize a module, or to open or close a gas reservoir. Commands, including instrument setting commands, are also conveniently delivered to the system 250 on a removable storage device. The central microprocessor 270 interprets these commands and accordingly executes actions such as the opening and closing of a main power switch or an alarm silencing switch. Preferably, the central microprocessor 270 controls the operation of the system 250 by executing a software application to be described below.

The event record storage and transfer features provide a user of the system 250 with a notice of the occurrence of a malfunction in a pressurized gas system, the nature and site of the malfunction, and whether the malfunction has been remedied. The user can also access a historical record of the operation of the system 250 in the form of event records, to determine whether malfunctions or status issues have arisen in the past, and to determine what commands have previously been issued. The event records can also be pushed automatically into a database, such as a computerized medical record of a patient being maintained on a pressurized oxygen system.

Figure 21:
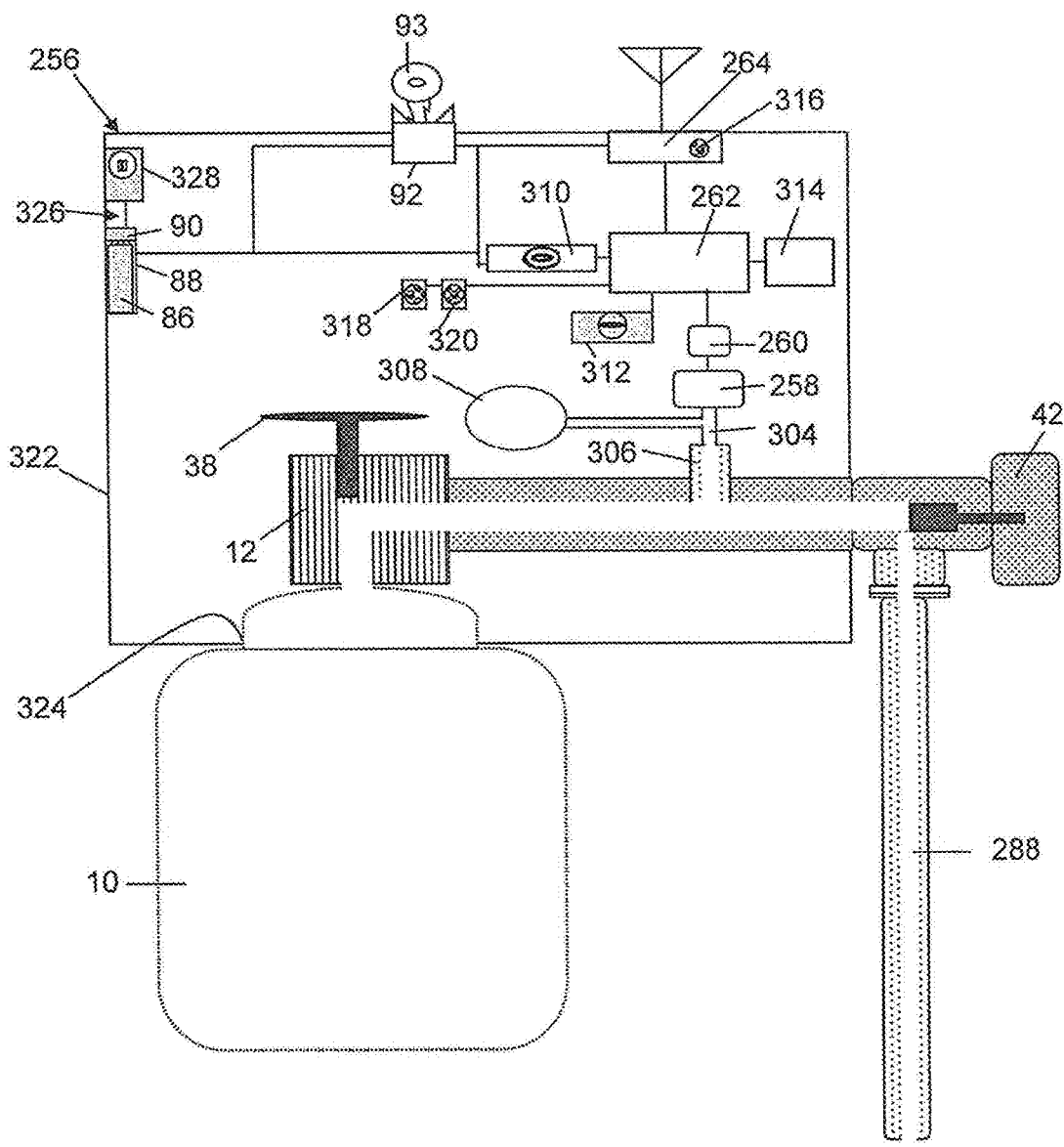
FIG. 21 shows a frontal semi-schematic view of a primary reservoir pressure monitor module according to the present invention.

The primary reservoir pressure monitor module 256 includes a digital primary reservoir pressure sensor 258 to measure the pressure of a primary gas cylinder 10 or other primary reservoir. A variety of suitable digital reservoir pressure sensors 258 are available from Honeywell Sensing and Control, Golden Valley, Minn. The digital reservoir pressure sensor 258 connects to the pressurized gas system via a gas pressure inlet 304. In the example shown in FIG. 21, the reservoir pressure sensor 258 is connected to the pressurized gas system via a tubular adaptor member 306, which is in gas tight engagement with a gas regulator 12. The adapter member 306 is preferably located at any point downstream of the main valve 38 and upstream of a pressure valve 42 or other terminal valve of the regulator 12. This is the location at which reservoir pressure is most reliably sensed. An analog pressure gauge 308 can also be included in the primary reservoir pressure monitor module 256, preferably connected to the gas pressure inlet 304 upstream from the digital reservoir pressure sensor 258. It will be understood that the primary reservoir pressure monitor module 256 can constitute a separate unit from a regulator, and engageable to a regulator, as shown in FIG. 21, or it can be a single unit in which a primary reservoir pressure monitor module 256 is structurally integrated with a regulator, the regulator and primary reservoir pressure monitor module 256 constituting a unitary regulator-primary reservoir pressure monitor module assembly (not shown).

The primary reservoir pressure monitor module 256 also includes a primary reservoir pressure error signal generator 260 operatively connected to the primary reservoir pressure sensor 258 and to the pressure monitor microprocessor 262. Digital pressure data are relayed from the primary reservoir pressure sensor 258 to both the pressure monitor microprocessor 262 and the primary reservoir pressure error signal generator 260. The primary reservoir pressure error signal generator 260 can include an electromechanical switch (not shown) operatively connected to the pressure monitor microprocessor 262, the switch generating a primary reservoir pressure alarm signal upon sensing a reservoir pressure violating at least a lower preset alarm level. Alternatively, the primary reservoir pressure error signal generator 260 can include a microprocessor (not shown) with circuitry for comparing gas pressure values to preset limit values. In another alternative configuration, the primary reservoir pressure error signal generator 260 is a component of the pressure monitor microprocessor 262 (not shown). Reservoir pressure alarm signals are received by the pressure monitor microprocessor 262.

Upon receipt of a primary reservoir pressure error signal, the pressure monitor microprocessor 262 routes the reservoir pressure error signal to the pressure monitor transceiver 264, to which it is operatively connected. The pressure monitor transceiver 264 transmits the primary reservoir pressure error signal to the central transceiver 266, situated in the communication/flow monitor module 274. The pressure monitor transceiver 264 and central transceiver 266, are preferably wireless RF transceivers, and most preferably Digi Xbee RF modules 267 (Digi International Inc., Minnetonka, Minn.) that are routers and can transmit data to a cloud 269. These RF transceivers incorporate error checking as part of their transmission protocol and are very reliable. A Bluetooth® transceiver can alternatively be employed.

Figure 42B:
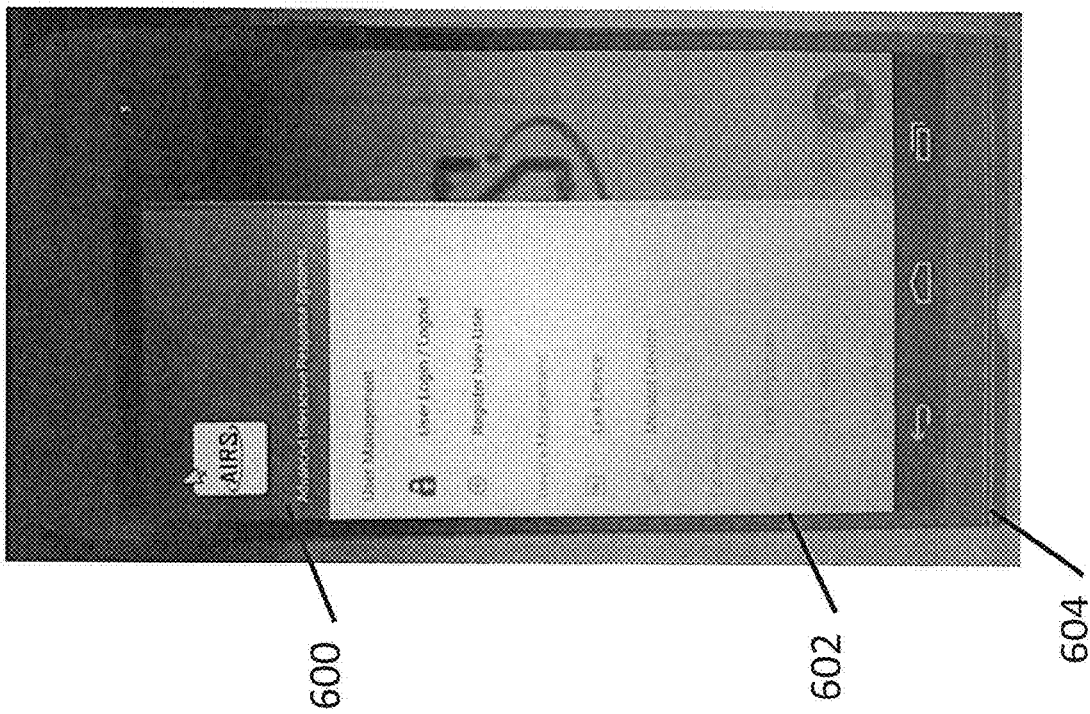
FIG. 42A shows a smartphone application and FIG. 42B shows an example menu of a smartphone application.
Figure 42A:
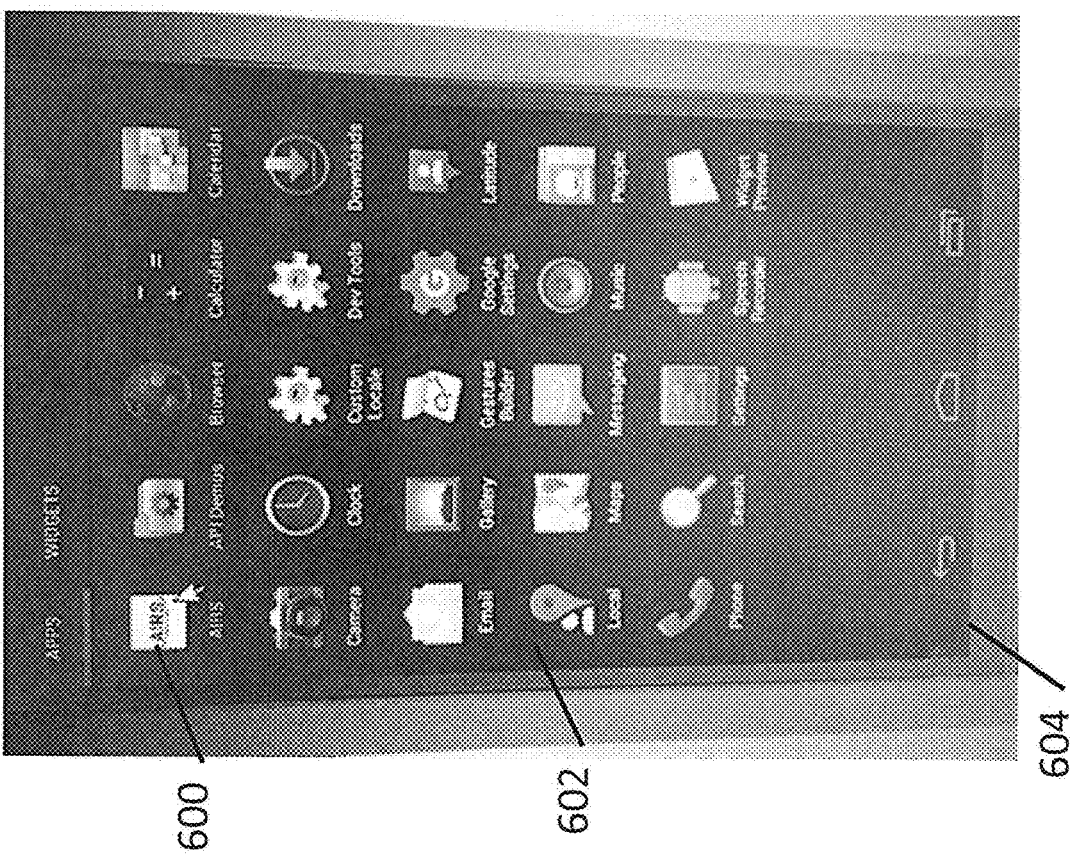
Figure 43:
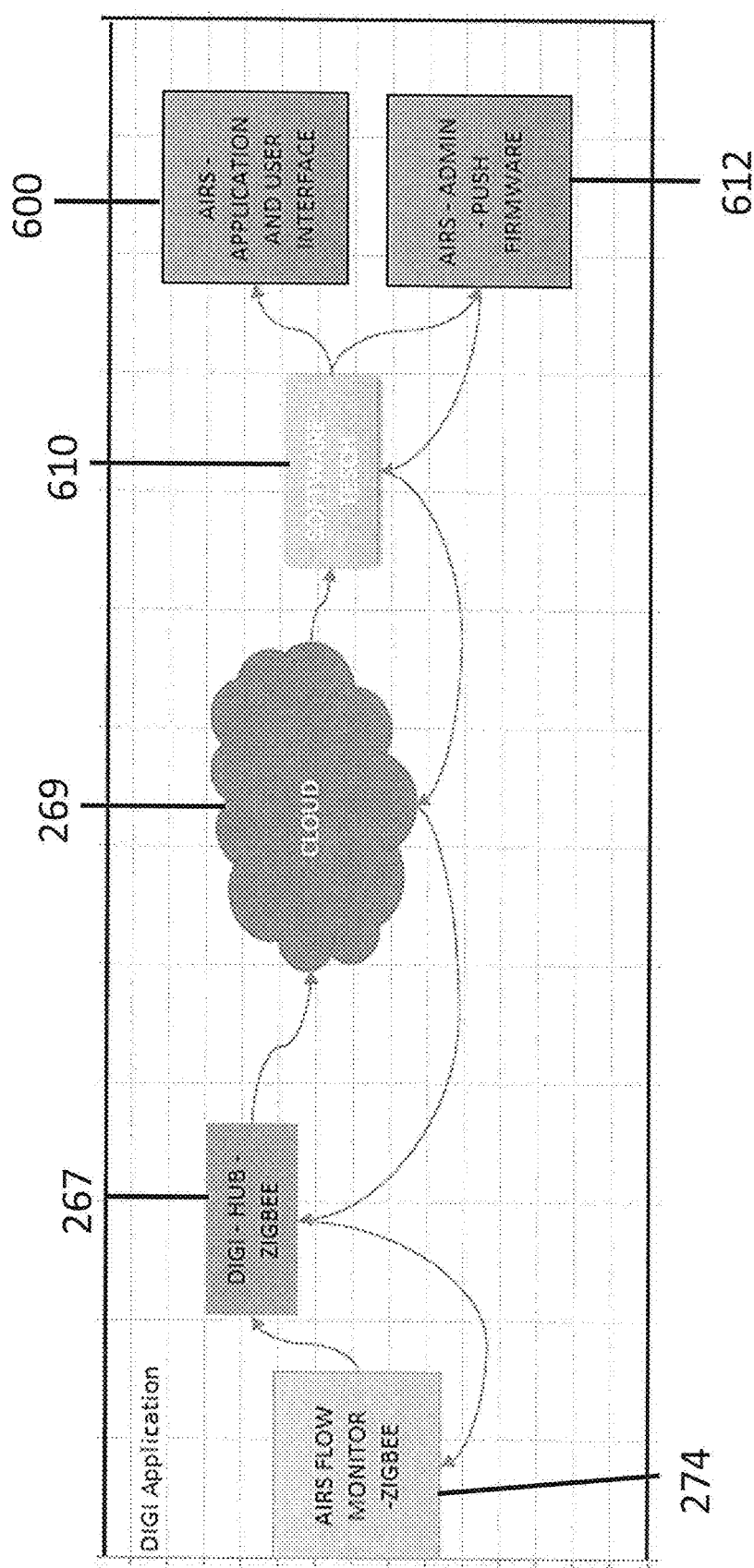
FIG. 43 is a flowchart of the flow of data in the systems and application.

An application ("app") 600 can receive any data from the devices and systems described herein. "App" or "Application" as used herein, refers to a software program designed to run on the operating systems of a handheld or mobile computing device. The handheld computing device can be any suitable smartphone (such as, but not limited to, an (PHONE® (Apple)), tablet (such as, but not limited to, an (PAD® (Apple), or Microsoft SURFACE® tablet), or handheld or mobile device that allows for the use of Apps (such as, but not limited to, portable mp3 players and smart watches) and provides a graphical interface with which to display data from the systems herein. Through the app 600, the data can be transformed into an easy to read format that allows oxygen data and alerts generated by the systems to be tracked and displayed. This allows for remote viewing of the patient's oxygen status. The app 600 is shown in FIG. 42A on a screen 602 of a smartphone 604. An example menu 606 of the app 600 is shown in FIG. 42B. FIG. 43 shows a flowchart of how data flows through the system with the app 600. Any necessary software 610 can be used and administration can also push firmware 612.

Figure 44:
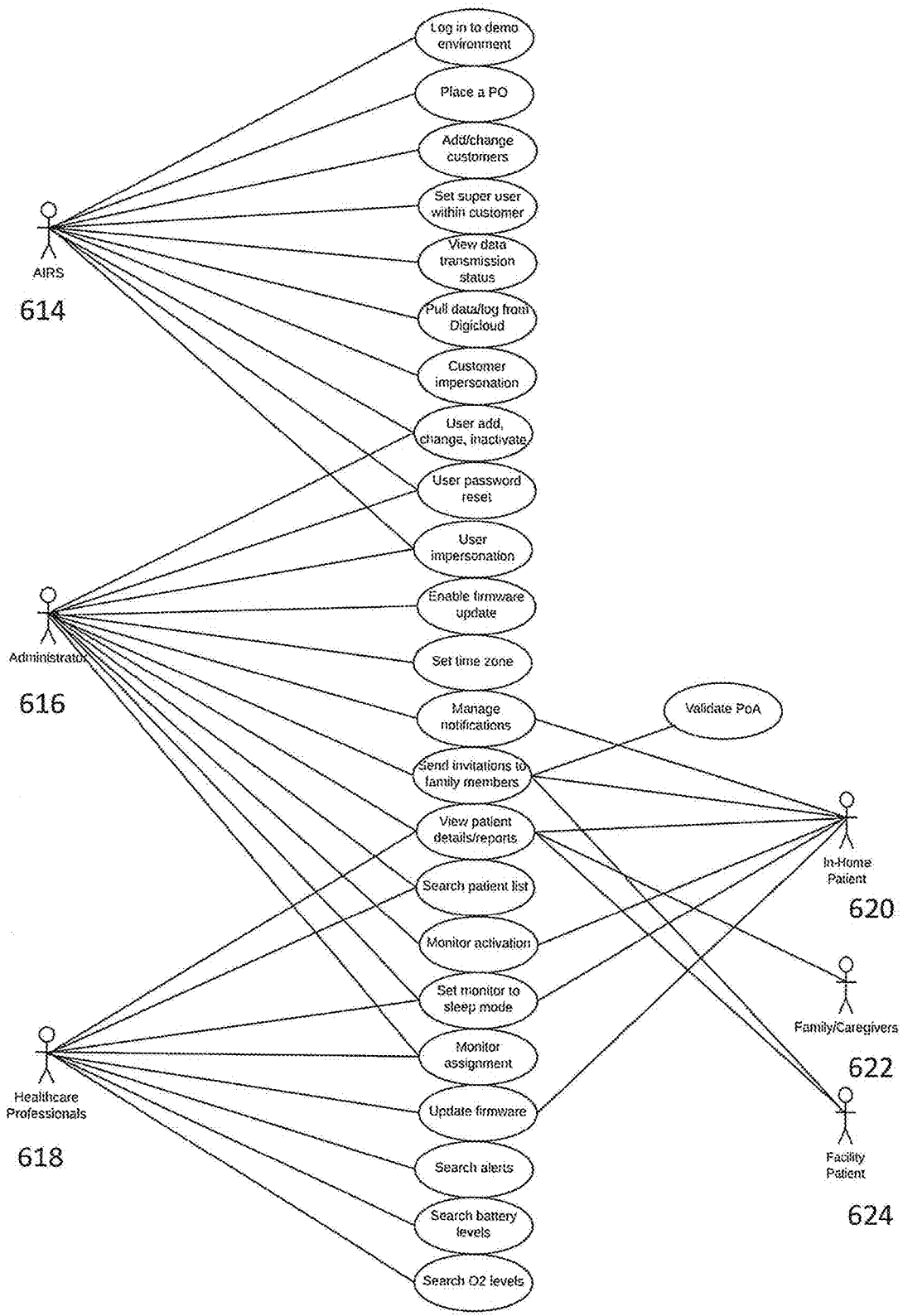
FIG. 44 shows how users can interact with the application.

FIG. 44 shows various users and how they can interact with the app 600. System managers (AIRS) 614, administrators 616, healthcare professionals 618, in-home patients 620, family/caregivers 622, and facility patients 624 can access different functions in the app 600.

FIGS. 45A-45C shows various menus within the app 600 relevant for different individuals. In-home patients (FIG. 45A) can activate register; manage Contacts-emergency contact, send/revoke invites, secondary contacts, caregivers, oxygen suppliers, alert settings; access my Account-email, address, phone number, billing info; access Help-tutorials, FAQ, videos, support, contact us; access Patient View; access Device Management-firmware update, link devices, set time zone, sleep mode; and access Actors-administrators, nurse, doctor, patients, family members, oxygen suppliers. Nursing homes/hospitals (FIG. 45B) can access Device Management; access Patient search; access Patient-patient, families, assigned caregivers (patient specific alerts, graphs and history); access Status Page/Alerts Page-landing page; access Management Console (Administrator)-settings, user management, alert settings, facility settings, adding/changing users, resetting passwords, deactivate users; access Device Updates-firmware updates, link devices, set time zone, sleep mode; and access Actors-administrator, nurse, doctor, patient, family members, oxygen suppliers. The system management (AIRS Team) (FIG. 45C) can access Customer Management-freeze account, payment, history, billing info, access Repurpose Device; access Device Management-firmware updates, link devices, set time zone, sleep mode; and access Actors-AIRS' customer service representative, collections, tech support. FIG. 45D lists the types of data that can be collected by the app 600, such as, but not limited to, flow, pressure, tank status, oxygen percentage, ETCO2, SPO2, patient's pulse, battery status, device status, and alerts.

Optionally, the primary reservoir pressure monitor module 256 includes at least one reservoir pressure alarm indicator 310. The primary reservoir alarm indicator 310 is actuated by the pressure monitor microprocessor 262 upon reception of a primary reservoir pressure error signal from the primary reservoir pressure error signal generator 260. One or multiple primary reservoir alarm indicators 310 can be included, such as, but not limited to, an audio alarm tone producer such as a bell, a mechanical buzzer, and electronic tone synthesizer, and a visual display, such as an incandescent lamp, a fluorescent tube, a light emitting diode or a liquid crystal display. The pressure monitor microprocessor 262 can be programmed with alarm display routines to produce distinctive displays for particular alarm indications, as previously described for the indicator mechanisms 26 of the gas flow and pressure error alarm device 20. The primary reservoir pressure monitor module 256 also includes an alarm silencing switch 312 operatively connected to the pressure monitor microprocessor 262 to permit a user to silence the primary reservoir alarm indicator 310 and abort the primary reservoir pressure error signal to the central transceiver 266. The alarm silencing switch 312 is preferably a key-controlled switch to prevent unauthorized personnel from silencing the alarm indicator 310. An alarm reset button (not shown) is also provided to reset the alarms and associated event data from memories.

Preferably, the primary reservoir pressure monitor module 256 includes a pressure monitor event memory 314 operatively connected to the pressure monitor microprocessor 262 and to the primary reservoir pressure error signal generator 260. The pressure monitor microprocessor 262 records primary reservoir pressure data and primary reservoir pressure error signals as event records in the pressure monitor event memory 314. The reservoir pressure data is recorded at predetermined clock intervals. The pressure monitor event memory 14 can be physically situated in a discrete memory component such as Erasable Programmable Read-Only Memory (EEPROM) chip, or it can be a component of the pressure monitor microprocessor 262 itself (not shown).

The pressure monitor microprocessor 262 also periodically creates status indication event records regarding the status of various components of the primary reservoir pressure monitor module. The status indications include but are not limited to connection status, that is, the connection or disconnection of the pressure monitor transceiver 264 is connected to another compatible transceiver; battery charge; and the activation and deactivation of the master power switch 92. The status indication event records are routed by the pressure monitor microprocessor 262 to the pressure monitor transceiver 264 for transmission to the communication/flow monitor module 268. Optionally, status indication event records are also recorded in the pressure monitor event memory 314. Visible status indications are provided at the primary reservoir pressure monitor module 256, including a master power indicator 320, a transceiver connection indicator 316, and a battery charge indicator 318. An audible battery alarm indicator (not shown) can also be included to alert a user to a battery charge below a predetermined limit.

Optionally, the pressure monitor microprocessor 262 is operatively connected to a digital pressure display (not shown), which displays reservoir pressure values continuously or at predetermined intervals. This option is useful if the previously described analog pressure gauge 308 is not included in the pressure monitor module 256.

The components of the primary reservoir pressure monitor module 256 are contained within a primary pressure module housing 322 of any convenient size and shape. Preferably, the pressure monitor housing 322 includes at least a bottom aperture 324 that permits the fitting of the pressure monitor module 256 over the top of a gas cylinder 10, with the main valve 38 protruding into the interior space of the primary pressure module housing 322. The pressure monitor housing 322 includes at least one display panel (not shown) which includes windows (not shown) to permit viewing of the previously described alarm indicators 310, the status indicators 312, 314, and 316, and a digital pressure display (not shown).

Electrical power to energize the primary reservoir pressure monitor is provided by a power subassembly 326. The power subassembly 326 includes the master power switch 92, and at least one battery 86 enclosed in a battery compartment 88 and mounted in battery clip 90. A Rechargeable Lithium-Ion battery is preferred, with the voltage and capacity of the battery depending on the type of included microprocessors, alarm indicators, and transceiver. The power subassembly 326 preferably also includes a battery charger 328. The battery charger 328 includes components well known in the art, including charge detection circuitry (not shown), a battery recharging circuit (not shown), and a receptacle for recharging), preferably 5 VDC. A battery status chip 450 is preferably included to store battery status indications. Essentially the same power subassembly 326 can be incorporated into the communication/flow monitor module 268 and the changeover/reservoir pressure monitor module 274.

Figure 22:
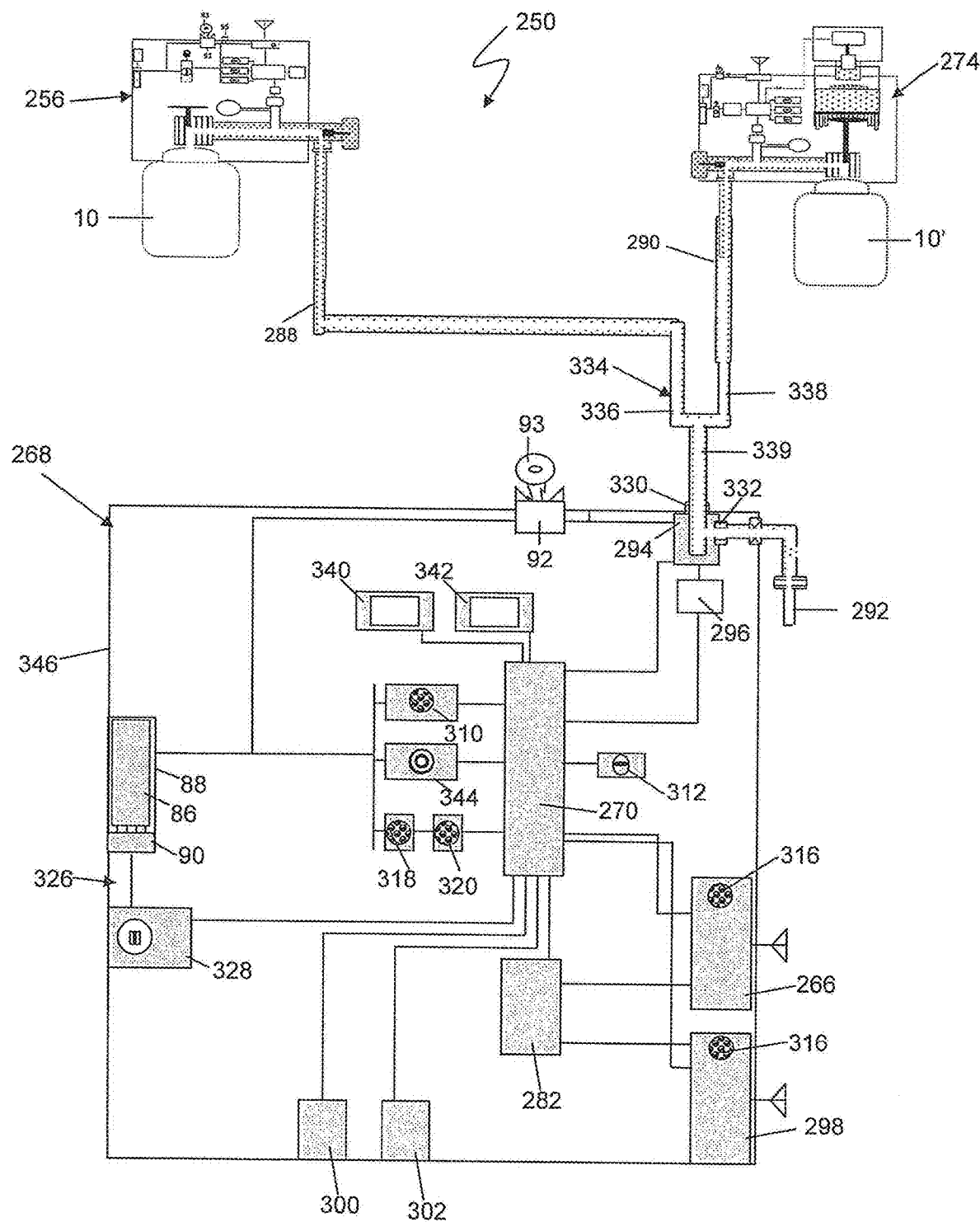
FIG. 22 shows a frontal semi-schematic view of a communication/flow monitor module according to the present invention.

The communication/flow monitor module 268, as shown in FIG. 22, includes a gas flow sensor 294, preferably a digital gas flow sensor, to measure a gas flow from an upstream gas reservoir toward at least one downstream appliance, and to generate digital gas flow data. An exemplary digital gas flow sensor 294 is the Honeywell Zephyr™ Digital Airflow Sensor. The gas flow sensor 294 connects to the pressurized gas system through at least one gas flow inlet 330, which directs a column of pressurized gas from at least the first upstream gas path 288 into the gas flow sensor 294. A gas flow outlet 332 directs the column of pressurized gas into the downstream path gas path 292. Preferably, the gas flow inlet 330 engages both the first upstream gas path 288, from the primary gas cylinder 10 and the second upstream gas path 290, from the reserve gas cylinder 10', by means of an inlet manifold 334. The inlet manifold 334 includes at least a first inlet port 336 for engagement with the first upstream gas path 288, and a second inlet port 338 for engagement with the second upstream gas path 290. The first inlet port 336 and second inlet port 338 merge into a common port 339, which is engaged to the gas flow sensor 294. Additional inlet ports can be included to accommodate additional primary and reserve gas reservoirs (not shown). Less preferably, two or more gas flow sensors 294 are included in the communication/flow monitor module 268, with each gas flow sensor 294 dedicated to measuring gas flow from a specific gas reservoir (not shown). The gas flow sensor 294 conveys gas flow data to the central microprocessor 270, to which it is operatively connected.

The communication/flow monitor module 268 also includes a gas flow error signal generator 296 operatively connected to both the gas flow sensor 294 and the central microprocessor 270. The gas flow error signal generator 296 generates a gas flow error signal upon the detection of a flow rate violating at least one predetermined flow value. The central microprocessor 270 also records the gas flow data and gas flow error signals as event records in the central event memory 282. The central event memory 282 can be physically situated in a discrete memory component such as EEPROM chip, or in the central microprocessor 270 itself.

Preferably, the central microprocessor 270 is operatively connected to a digital pressure display 340, and to a digital gas flow display 342, which display, respectively, the reservoir pressure of the primary gas reservoir and the gas flow rate to a downstream appliance. The digital pressure display 340 and digital gas flow display 342 can be combined into a single display that is switchable to display pressure and gas flow data from any source, including additional gas reservoirs (not shown).

The central microprocessor 270 is also operatively connected to at least one reservoir pressure error alarm indicator 310 and at least one gas flow error alarm indicator 344. The central microprocessor 270 actuates a reservoir pressure alarm indicator 310 upon receipt of a pressure error signal from the primary reservoir pressure monitor module 256 or the changeover/reservoir pressure monitor module 274. The central microprocessor 270 actuates a gas flow error alarm indicator 344 upon receipt of a gas flow error signal from the gas flow error signal generator 296. The structure and function of the alarm indicators is as previously described for the primary reservoir pressure monitor module 256. The audible alarm can preferably be actuated to produce sound at low, medium, and high volume levels, to indicate specific levels of gas flow or reservoir pressure shortfall.

The central microprocessor 262 also periodically creates status indication event records regarding the status of various components of the communication/flow monitor module 268. The status indications, and their routing and recording in event memories, is as previously described for the primary reservoir pressure monitor module 256. Visible status indications include a master power indicator 320, a transceiver connection indicator 316, and a battery charge indicator 318 and, optionally, an audible battery alarm indicator (not shown). The communication/flow monitor module housing 346 includes windows (not shown) includes windows to permit viewing of the previously described alarm indicators, status indicators, and digital displays.

The central microprocessor 270 also receives event records transmitted from the primary reservoir pressure monitor module 256 and records them the central event memory 282. Reception is preferably by means of the central transceiver 266, which is essentially identical to the previously described pressure monitor transceiver 264.

In addition to its gas flow monitoring function, the communication/flow monitor module 268 also receives primary reservoir pressure signals from the primary reservoir pressure monitor module 256, records them as event records, and routes them via the central transceiver 266 to the changeover/reservoir pressure monitor module 274. The changeover signal induces the changeover/reservoir pressure monitor module 272 to open the reserve gas cylinder 10', as will be described in detail below. The central microprocessor 270 is also configurable to generate a changeover signal in response to a gas flow error signal. This capability of opening a reserve gas reservoir in response to a gas flow error is especially useful when the primary gas source is an oxygen concentrator. Reservoir pressure is not a relevant property for oxygen concentrators, which maintain a constant low internal pressure by mechanical means such as a compressor.

Several modes of access are provided to event records stored in the central event memory 282. Event records are accessible by telephonic communication. The communication/flow monitor module 268 includes a telephonic module 298. Event records can be routed from the central event memory 282 to the telephonic module 298, which then makes a connection to a communications network and transmits the data to remote devices such as land-line telephones, cellular phones tablets, and other mobile devices, IP addresses, FAX machines, and the like. Preferably, the telephonic module 298 includes a GSM (Global System for Mobile Communications) Quad-Band cellular communications module transmitting text messages via the Short Messaging System (SMS). The telephonic module 298 connects to a cellular communication network in a preprogrammed connection mode, such as connection at predetermined intervals, and connection upon receipt of a gas pressure of gas flow error alarm signal. Once connected to the cellular communication network, the event records are transmitted via SMS to a phone number or IP address that has been programmed into the microprocessor.

Event records are also accessible by means of wireless transmission via the central transceiver 266, by any device equipped with a compatible wireless modem. Wireless access is useful in situations in which a remote user is in proximity to the communication/flow monitor module 268.

Event records are also accessible by download via cable to one or more remote devices, including but not limited to computers, such as personal computers (PC), tablets, and servers such as local network servers and web servers. Downloading can be performed via a cable, such as a USB, serial or Ethernet cable, or via removable storage devices, via the previously described ports and sockets provided in the communication/flow monitor module 268. Download of event records can be inducible by commands entered manually through a "send" button (one of the user input buttons 303) and associated circuitry (not shown) operatively connected to the central microprocessor 270. Download can be also be inducible by commands from a PC, server, or mobile device, the commands either being entered manually by a user or programmed for transmission at predetermined intervals. Download can also be inducible by the receipt of a particular type of event record, such as an error alarm signal, at the central microprocessor 270.

Preferably, the event records are stored in, or converted to, in a human-readable format, such as HTML-based web pages. In this format, the downloaded event records can be displayed on a user friendly interface, such as web browsers or spreadsheet programs well known in the art. Event records for a particular patient can be routed from a web server directly into the patient's electronic medical record file, stored at such sites as a physician's office, a nursing station, or the internal network of a hospital. Preferably, connected computers run a program to automatically update a patient's web page or other file upon receipt of new event records.

An exemplary microprocessor for use as the central microprocessor 270 is the Atmega 328P (Atmel, San Jose, Calif.). The Atmega 328P can also serve as the pressure monitor microprocessor 262 and the changeover/pressure monitor microprocessor 276, but in view of the simpler data handling demands on these microprocessors 262 and 276, less powerful microprocessors can be substituted. All operative connections amongst the components of the system 250, are preferably made by means of a printed circuit board (PCB). Specific PCB configurations are readily designed from the descriptions by any person skilled in the design of electronic circuits.

The changeover/reservoir pressure monitor module 274 is connectable to a reserve gas reservoir, such as a reserve gas cylinder 10'. It will be understood that the changeover/reservoir pressure monitor module 274 can constitute a separate unit from a regulator and engageable to a regulator, as shown in FIG. 23, or it can be a single unit in which a changeover/reservoir pressure monitor module 274 is structurally integrated with a regulator, constituting a unitary regulator-changeover/reservoir pressure monitor module assembly (not shown).

Figure 23:
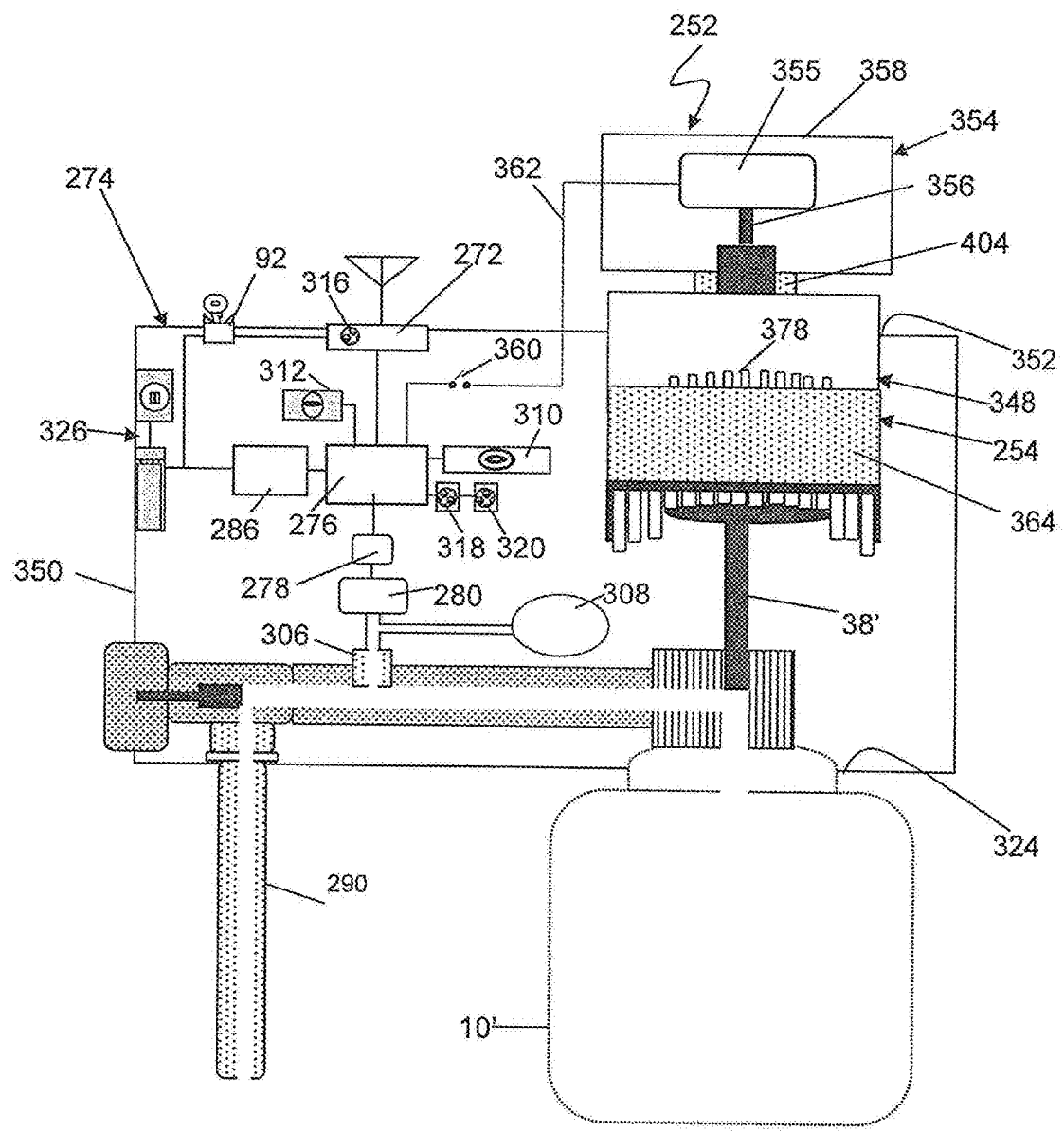
FIG. 23 shows a frontal semi-schematic view of a changeover/reservoir pressure monitor module according to the present invention.

As shown in FIG. 23, the changeover/reservoir pressure monitor module 274 includes the motorized reservoir changeover device 252 for opening the reserve gas cylinder 10' upon reception of a changeover signal. The changeover/reservoir pressure monitor module 274 preferably also includes pressure monitoring components similar or identical to those previously described for the primary reservoir pressure monitor module 256. That is, the changeover/reservoir pressure monitor module 274 includes a digital reserve reservoir pressure sensor 278, preferably a digital sensor, connected to the pressurized gas system via a tubular adaptor member 306, a reserve reservoir pressure error signal generator 280, an optional analog pressure gauge 308; a transceiver preferably an RF transceiver, termed a changeover transceiver 272; an optional reservoir pressure alarm indicator 310, an alarm silencing switch 312, status indicators 316, 318, 320, an optional digital reservoir pressure display (not shown) and a power subassembly. Also included is a microprocessor, termed a changeover/pressure monitor microprocessor 276. The changeover/pressure monitor microprocessor 276 performs all of the functions previously described for the pressure monitor microprocessor 262, and additionally regulates reservoir changeover functions, but it is not necessarily structurally or functionally distinguishable from the pressure monitor microprocessor 262. The changeover/pressure monitor microprocessor 274 receives reserve reservoir pressure data from the reserve reservoir pressure sensor 278 and reserve reservoir pressure error signals from the pressure error signal generator 280. Preferably, the changeover/reservoir pressure monitor module 274 includes a memory, termed the changeover/reservoir pressure event memory 286, for the recording of reserve reservoir pressure data, reserve reservoir pressure error signals, and status indications, as event records. The changeover/pressure monitor microprocessor 276 also routes the event records to the changeover transceiver 272 for transmission to the communication/flow monitor module 268. These pressure monitoring components give the changeover/reservoir pressure monitor module 274 the capability of monitoring the pressure of a reserve gas reservoir after the reservoir has been opened by the motorized reservoir changeover device 252. The changeover/reservoir pressure monitor module 274 is suitable use as a primary reservoir pressure monitor module engaged with a primary gas reservoir 10, with the reservoir changeover device 252 removed, inactivated, or disengaged from the main valve of the primary reservoir (not shown). The changeover/reservoir pressure monitor module 274 can also be mounted on a primary reservoir with the reservoir changeover device 252 engaged to the main valve, to enable a user to open or close the main valve for a purpose other than reservoir changeover. For example the main valve 38 of a primary gas reservoir 10 can be closed in a hazardous situation by an emergency cut-off button to be described below.

The reservoir changeover device 252 includes a motor member 354 for applying torque to a valve coupler 348 which is engageable with the main valve 38'. The valve coupler 348 transfers torque from the motor member 354 to the main valve 38', to operate the main valve 38'. The motor member 354 includes a motor 355, preferably an electric motor, situated in a motor housing 358. An exemplary motor is the Pololu geared DC motor, with 499:1 gear ratio, and 300 oz. install torque at 6V DC (Pololu Robotics, Inc., Las Vegas, Nev.). Alternatively, any suitable servo or stepper motor with similar torque can be used. Preferably, the valve coupling device is a universal valve coupler 254, to be described in detail. Alternatively, the valve coupler 348 can include any coupling device known in the art, including a device having a fixed geometry complementary to the geometry of a particular main valve 38.

As shown in FIG. 23, the changeover/reservoir pressure monitor module 256 is contained in a changeover/reservoir pressure monitor module housing 350, which differs from the previously described primary pressure monitor housing 322 by the addition of a top aperture 352, through which the motorized reservoir changeover device 252 extends, and the provision of sufficient internal space to accommodate the valve coupler 348

The changeover/pressure monitor microprocessor 276 is operatively connected to the changeover transceiver 272 and to the motor 355. The changeover/pressure monitor microprocessor 276 actuates the motor 355 upon receipt of a changeover signal from the communications/flow monitor module 268. Actuation is preferably accomplished by the closing of a normally open motor switch 360 controlling a motor driver circuit 362.

A preferred valve coupler 348 is the universal valve coupler 254, which is capable of engaging main valves 38' regardless of their geometry and size, and regardless of their rotational position. A universal valve coupler 254 according to present invention is shown in FIGS. 24 A-I. The universal valve coupler 254 includes a pin housing 364 having a bottom end 366 facing toward a main valve 38' to be engaged, an opposite top end 368, and at least one lateral side 370 therebetween. A plurality of mutually parallel pin channels 372 traverse the length of the pin housing 364, the pin channels 372 being mutually parallel and axially aligned with an axis extending from the top end 368 to the bottom end 366 of the pin housing 364. Each pin channel 372 has a top opening 374 defined in the top surface 368 of the pin housing 364 and a bottom opening 376 defined at the bottom end 366 of the pin housing 364. A spring pin 378, for transferring torque to the main valve 38' is slidably contained within each pin channel 372.

Each spring pin 378 includes a bottom section 380 to engage the valve 38', the bottom section 380 being protrudable below the bottom opening 376 of the pin channel 372 in which it is contained, and upper section 382 terminating in a pin head 384 protrudable above the top opening 374 of the pin channel 372. The pin head 384 has a larger diameter than that of the top opening 374, to prevent the spring pin 378 from dropping out of the pin channel 372. The bottom section 380 of the spring pin 378 is contactable with the main valve 38'. It is preferably hexagonal in cross section, to provide leverage against the valve 38', but it can alternatively be circular, or of any polygonal shape. In an easily fabricated exemplary spring pin 378 depicted in FIGS. 24A and 24B, a hex standoff serves as the bottom section 380 and a screw serves as the upper section 382.

Each pin channel 272 includes a bottom portion 386 to accommodate the bottom section 380 of the spring pin 378, and a middle portion 388 and an upper portion 390 that together accommodate the upper section 382 of the spring pin 378. The bottom portion 386 of the pin channel 272 closely approximates the bottom section 380 of the spring pin 378, with the diameter of the bottom portion x exceeding that of the bottom section 380 only to the extent that allows the spring pin 378 to slide within the pin channel 372. This close fit provides maximal axial support to the spring pin 378 when the pin housing 364 is rotated against the main valve 38'. Similarly, the upper portion 390 of the pin channel 372 closely approximates the upper section 382 of the spring pin 378.

Figure 24A:
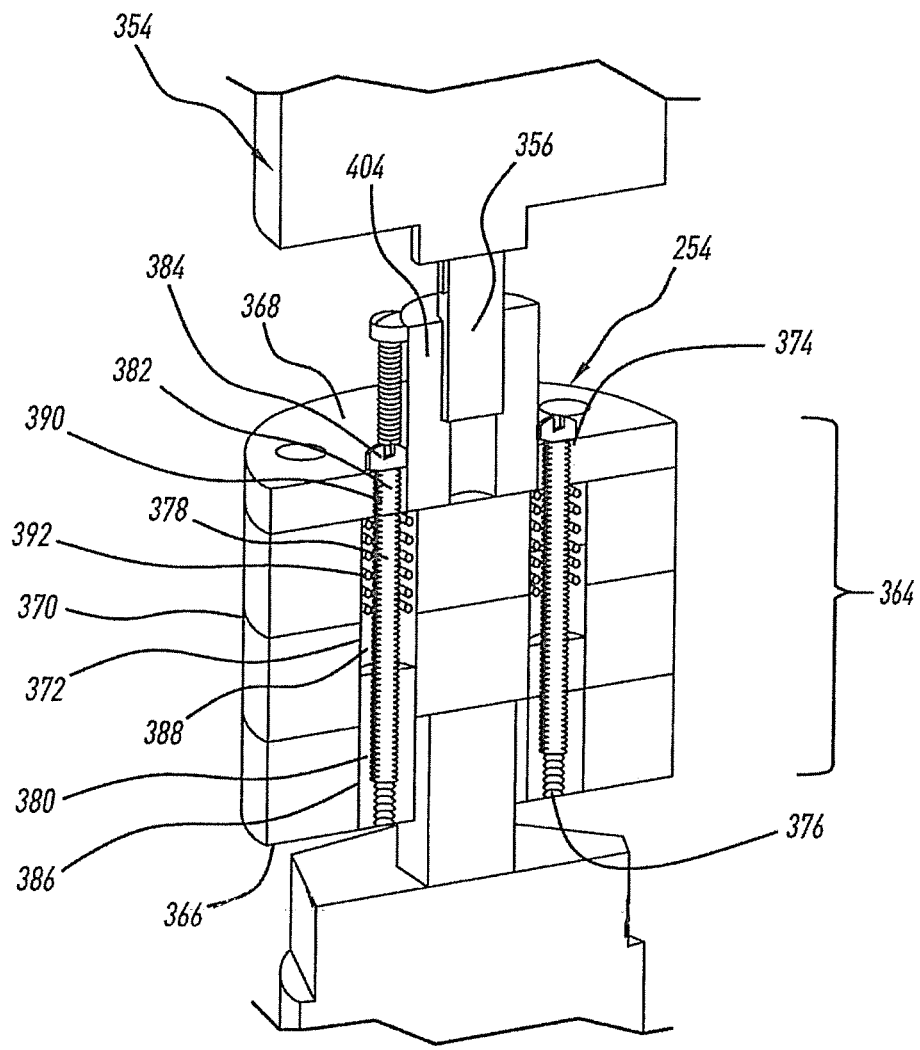
FIG. 24A shows a cutaway perspective view of a universal valve coupler according to the present invention, with the universal valve coupler simplified to show two pin channels, with spring pins in lowered position.
Figure 24B:
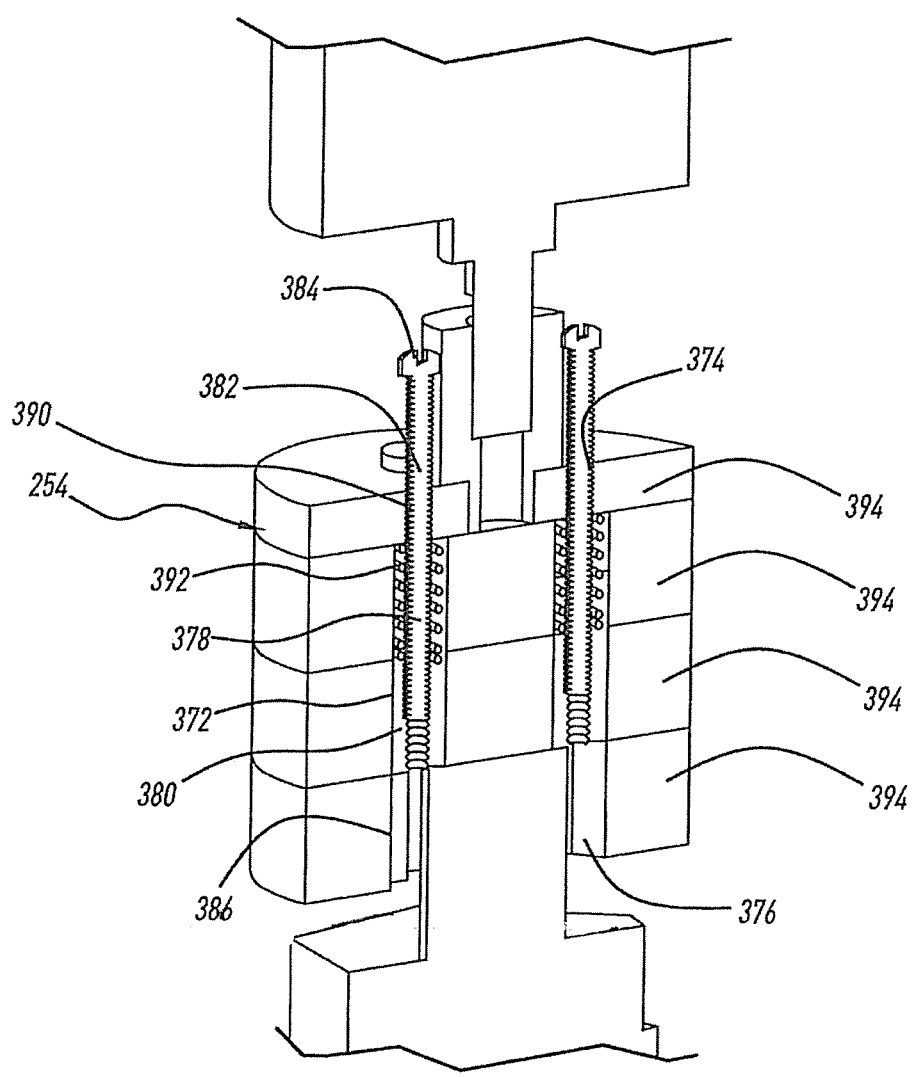
FIG. 24B shows a cutaway perspective view of a universal valve coupler according to the present invention, with the universal valve coupler simplified to show two pin channels, with spring pins in raised position.

The middle portion 388 of the pin channel 372 is of a diameter sufficient to contain a biasing member, preferably a coil spring 392, which is disposed about the upper section 382 of the spring pin 378. The spring 392 is compressible between the bottom section 380 of the spring pin 378, the upper portion 390 of the pin channel 372, such that the spring 392 biases the spring pin 378 downward, toward the main valve 38' to be engaged. The spring 392 is of sufficient strength to force the bottom section 380 of the spring pin 378 to protrude at least partially through the bottom opening 376 of the pin channel 372. The strength of the spring 392 is also sufficiently low to allow the spring pin 378 to slide upward within the pin channel 372 when a main valve 38' is brought into contact with the spring pin 392. Any alternative biasing member known in the art can be substituted for the spring pin 392, for example a resilient collar (not shown) disposed about the upper section 382 of each spring pin 378. When a spring pin 378 is forced upward by contact with the valve 38', pin head 384 and at least part of the upper section 382 emerge from the top opening 374 of the pin channel 372, as shown in FIG. 24B.

The pin housing 364 can be fabricated as a single solid structure, with continuous pin channels 372 bored through or molded into the length of the pin housing 364 (not shown). Alternatively, the pin housing 364 can be fabricated as least two adjacent housing segments 394, as shown in FIG. 24B, which shows a pin housing 364 four housing segments 394. An advantage of assembling the pin housing 364 from multiple segments is ease of fabrication.

Alternatively, the pin housing 364 can include at least two noncontiguous plates. An example including an upper housing plate 396 and a lower housing plate 398 is shown in FIGS. 24C and 24F. The lower housing plate 398 includes the bottom openings 376 of the pin channels 372 and the upper housing plate 396 includes the top openings 374. A space defined between the upper housing plate 396 and the lower housing plate 398 represents the middle portions 388 of the pin channels 372, and accommodates the spring 392 or other biasing member. In the example shown in FIGS. 24C-24F.

In this example, the lower housing plate 398 defines a single common bottom opening 400 of all of the pin channels 372. This configuration is preferable for a tightly packed bundle of spring pins 372. Preferably, the perimeter of the common bottom opening 400 is contoured to fit the contours of the outermost rank spring pins 378, as shown in FIG. 24C. This contouring provides additional axial stability to the spring pins 378 when torque is applied to the pin housing 364. The segments or plates of the pin housing 364 can be fastened together by any suitable fastening hardware, including but not limited to, longitudinal bolts or retaining pins (not shown).

The universal valve coupler 254 optionally includes a cowling 402 extending downward from the pin housing 364, its length being sufficient to surround the bottom sections 380 of spring pins 378 protruding through the bottom openings 376 of the pin channels 372. The cowling 402 provides a recess that allows the main valve 38' to enter the universal valve coupler 254.

The universal valve coupler 254 also includes an acceptor member 404 to connect the universal valve coupler 254 to the motor shaft 356.

Figure 24G:
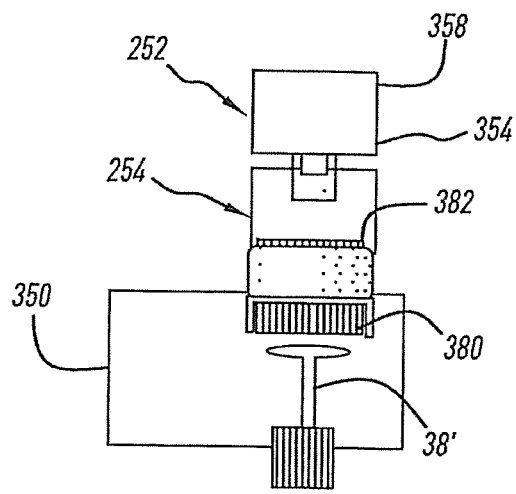
FIG. 24G shows a semi-schematic frontal view of a reservoir changeover device prior to engagement with a reservoir valve.
Figure 24H:
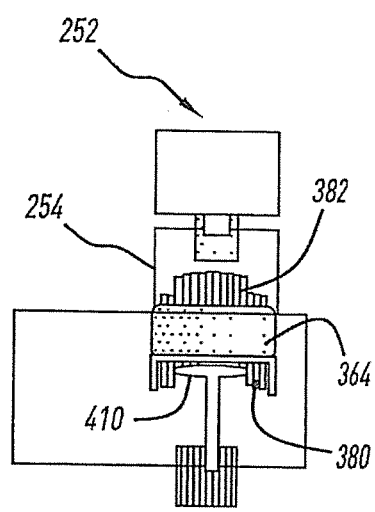
FIG. 24H shows a semi-schematic frontal view of a reservoir changeover device engaged with a reservoir valve.
Figure 24I:
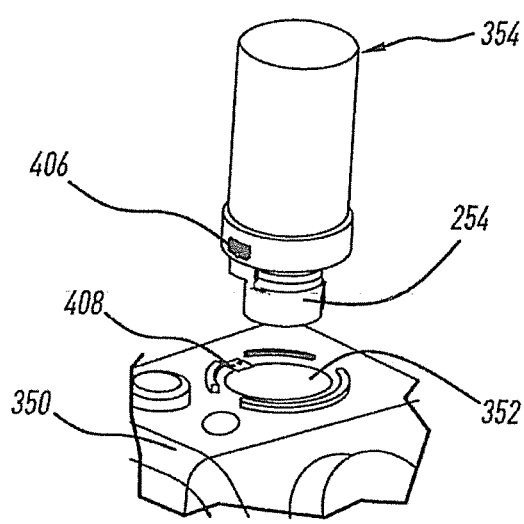
FIG. 24I shows a perspective view of a changeover/reservoir pressure monitor module.

The reservoir changeover device 252 is mounted upon the top aperture 352 of the changeover/reservoir pressure module housing 350, with the universal valve coupler 254 extending downward to engage the main valve 38'. Any engagement hardware known in the art can be used to engage the reservoir changeover device 252 to the housing 350, and the engagement can be either permanent or reversible. Preferably, reversible engagement is mediated by a snap-lock device 406 as shown in FIG. 24I. Any suitable means of reversible engagement known in the art can alternatively be used, such as a bayonet mount or a breech-lock mount (not shown). The electrical connection between the motor 355 and the motor switch 360 (FIG. 23) is preferably made by an electrical plug 408 integrated into the top aperture 352, the plug engaging a socket (not shown) in the motor member 354. It will be understood that any wiring arrangement known in the art can be used to connect the motor 355 to the motor switch 360.

In operation, the universal valve coupler 254 is brought with the main valve 38', either by lowering the coupler 254 onto the main valve 38' or by introducing the main valve 38' upward into the bottom aperture 324 of the changeover/reservoir pressure module housing 350. As shown in FIGS. 24G and 24H, a subset of spring pins 378 that comes into contact with the main valve 38' are slidingly displaced upward against the tension of the spring 392. The subset of spring pins 378 that do not come into contact with the main valve 38' continue to protrude beyond the bottom openings 376 of the pin channels 372, their bottom sections 380 forming a pocket 410 closely conforming to the perimeter of the main valve 38'. When torque is applied to the universal valve coupler 254 by the motor 355, the torque is transmitted by the pocket 410 to the main valve 38. It will be understood that the universal valve coupler 254 can be employed to apply torque not only to valves, but also to any object to be rotated.

The opening of a valve 38' by the reservoir changing device 252 can conceivably can cause damage to the valve 38' by continuing to apply torque after the valve 38' has reached its fully open position. The valve 38' can also be opened too little as a result of backlash, that is, torque application that does not translate into immediate valve rotation. To ensure safe and adequate opening of the main valve 38', the changeover/pressure monitor microprocessor 276 can be configured to execute a valve opening feedback loop.

The valve opening feedback loop is triggered by the reception of a changeover signal by the changeover/pressure monitor microprocessor 276. In an initial state, with the main valve 38' of the reserve cylinder 10' closed, the reserve reservoir pressure sensor 278 registers zero psi over ambient pressure. Upon reception of a changeover signal from the communication/flow monitor module 268 the microprocessor 276 commands the motor switch 360 to close. This energizes the motor 355, which applies valve opening torque to the main valve 38'. As the main valve 38' begins to open, the reserve reservoir pressure sensor 278 begins to sense the internal pressure of the reserve gas cylinder 10'. The motor switch 360 continues to remains open, and the motor continues to exert torque, until the digital pressure sensor senses a predetermined threshold pressure value, which indicates that the main valve 38' has opened sufficiently. Upon reception of the threshold pressure value, the microprocessor 276 commands the motor switch 360 to open, de-energizing the motor 155. The feedback loop closes with the cessation of torque application upon the main valve 38'.

The valve opening feedback loop can be generally applied as a method for safely and optimally opening any type of pressurized gas reservoir valve, including the steps of engaging a motorized coupling device to a main valve of a pressurized gas reservoir, the main valve being in closed position; engaging a pressure sensor to an outlet of the pressurized gas reservoir; operatively connecting the pressure sensor to a microprocessor; receiving a signal to open the main valve of the pressurized gas reservoir at the microprocessor; sending an actuation signal from the microprocessor to the motorized coupling device; actuating the motorized coupling device; applying valve-opening torque to the main valve with the actuated motorized coupling device; sensing a gas pressure at the outlet of the pressurized gas reservoir with the pressure sensor; generating gas pressure data with the pressure sensor; receiving the gas pressure data at the microprocessor; sensing a gas pressure above a predetermined threshold; generating gas pressure data indicating a gas pressure above the predetermined threshold; receiving at the microprocessor the pressure data indicating a gas pressure above the predetermined threshold; ceasing the actuation signal from the microprocessor; ceasing the actuation of the motorized coupling device, and ceasing valve-opening torque on the main valve by the motorized coupling device.

Less preferably, the microprocessor 276 can simply be configured to close the motor switch 155 for a predetermined amount of time upon the reception of a changeover signal, the predetermined time being selected to reduce the risk of valve damage. Alternatively, a mechanical slip clutch (not shown) or equivalent device can be incorporated into the reservoir changeover device 256 to prevent the over or under opening of the main valve 38'.

The motorized reservoir changeover device 252 can rotate a main valve 38 in a direction that either opens or closes the main valve 38. In addition to the previously described actuation of the reservoir changeover device 252, manual actuation of the device by a user is also within the scope of the present invention. Preferably, the user input buttons 303 include a load button (not shown) and an unload button (not shown), which actuate rotation of the reservoir changeover device 252 in, respectively, a valve-opening or valve-closing direction. The unload button (not shown) can also act as an emergency shut-off button (not shown), for cutting off the supply of gas in the event of a hazardous condition, such as a fire. This emergency provision is operative on primary gas reservoirs, reserve gas reservoirs, or any reservoir to which a motorized reservoir changeover device 252 is engaged.

The present invention is readily adapted for use as an alarm device for pressurized systems for gases other than oxygen through simple substitutions of materials, such as gas-tight seals, and of valves and sensors appropriate for the particular gas, as will be well known to this skilled in the art of that gas. Through such substitutions, the present invention is a useful alarm and communication system for pressurized gasses including, but not limited to propane, medical air, carbon dioxide, acetylene, hydrogen, nitrogen, helium, argon, ethylene, xenon, and mixtures thereof. The present invention is readily adapted to any type of gas regulator, including two-stage gas regulators. The present invention is also readily adapted for use in pressurized liquid systems, with suitable substitutions such as the use of liquid tight seals and fluid regulators (not shown). Through such substitutions, the present invention is a useful alarm and communication system for pressurized systems including, but not limited to, water, alcohols, petrochemicals including gasoline, diesel and other fuels, heating and lubricating oils, and the liquefied forms of oxygen, nitrogen, hydrogen, helium, and carbon dioxide.

For example, the system 250 can be used to monitor propane tanks used in home heating or other utility applications. In this type of application (not shown), the primary reservoir pressure monitor module 256 is in gas-tight engagement with a primary propane tank, and the changeover/reservoir pressure monitor module 274 is in gas-tight engagement with a reserve propane tank. The communications/flow monitor module 268 transmits notices of gas pressure or flow alarms to remote users, and allows users to monitor the status of the system and to enter commands to modify its function.

In another example, the system 250 can be used as a safety device for diving with self contained underwater apparatus (SCUBA). In an exemplary configuration, the primary reservoir pressure monitor module is in gas-tight engagement with a primary air tank of a SCUBA apparatus, and said changeover/reservoir pressure monitor module is in gas-tight engagement with a reserve air tank of the SCUBA apparatus. The primary reservoir pressure monitor module, communication/flow monitor module, changeover/reservoir pressure monitor module are enclosed in at least one waterproof housing. The system provides alarms to a diver using the SCUBA apparatus, automatic opening of the reserve air tank, and alarm signals to remote parties, such as the crew of a nearby diving boat.

Figure 26:
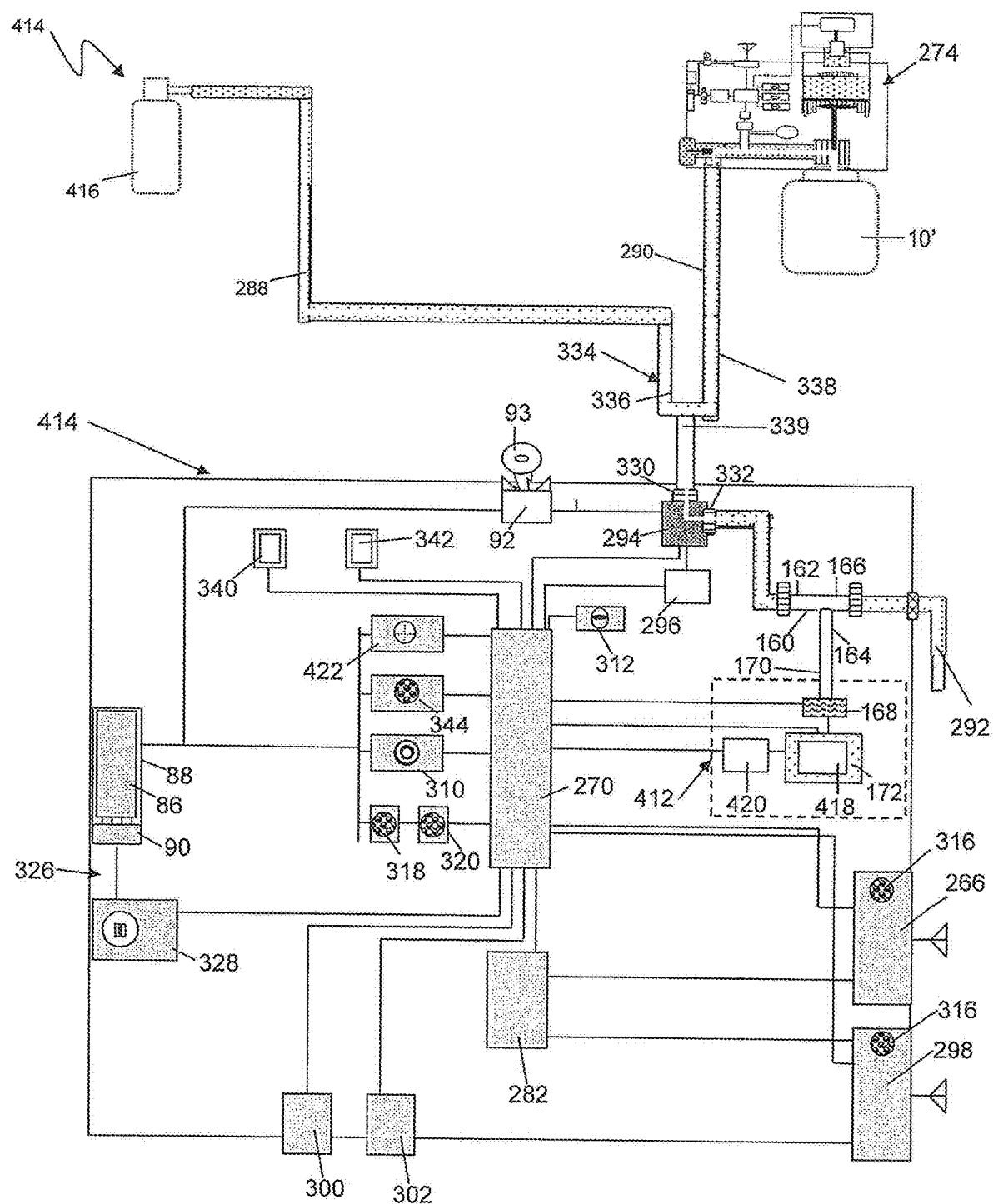
FIG. 26 shows a semi-schematic frontal view of a communication/flow/oxygen monitor module according to the present invention.
Figure 27A:
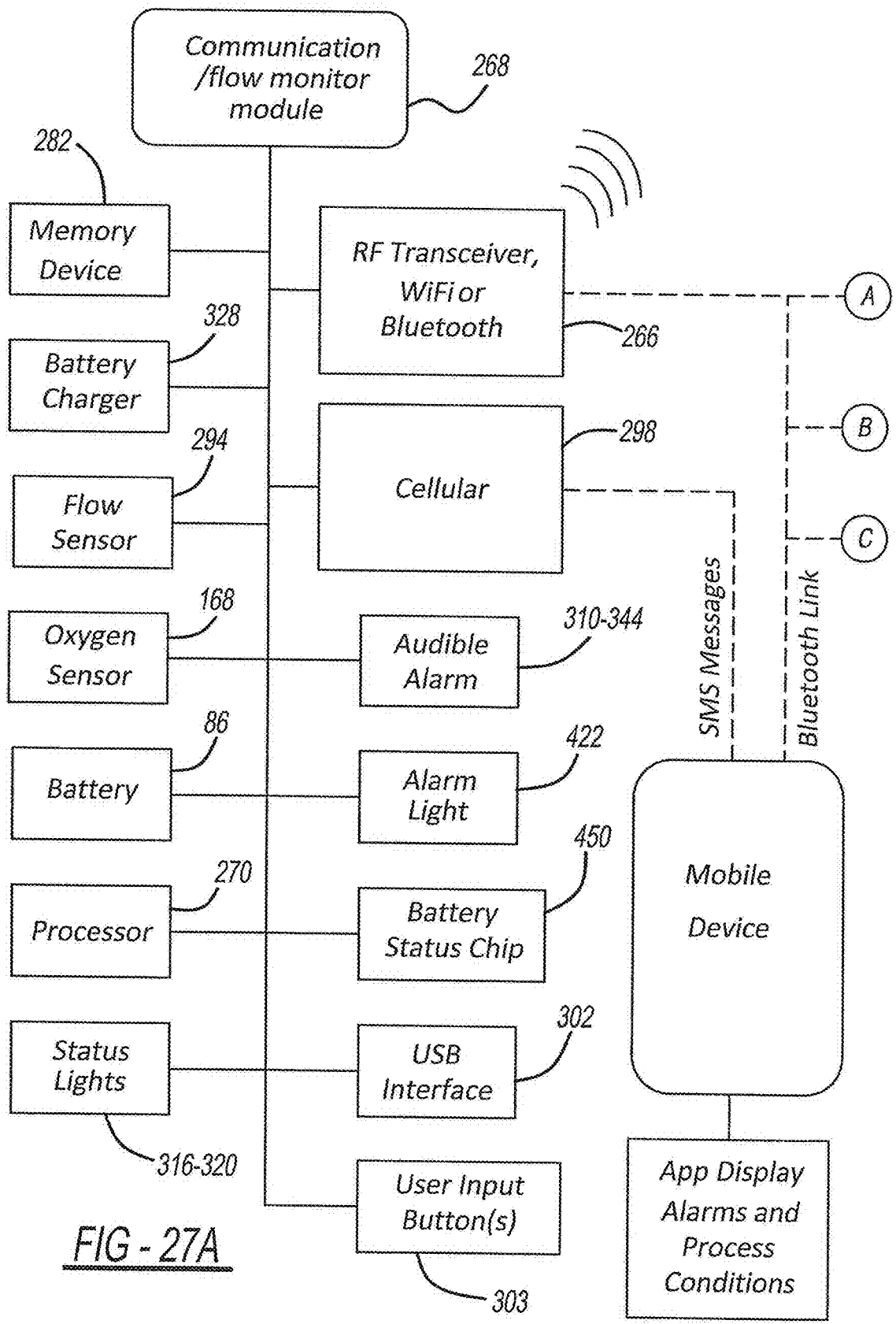
FIG. 27A, FIG. 27B, FIG. 27C, and FIG. 27D show a semi-schematic overview of the structure, operation, and information flow in a gas supply warning, communication, and changeover system including a vibrating bracelet.
Figure 27B:
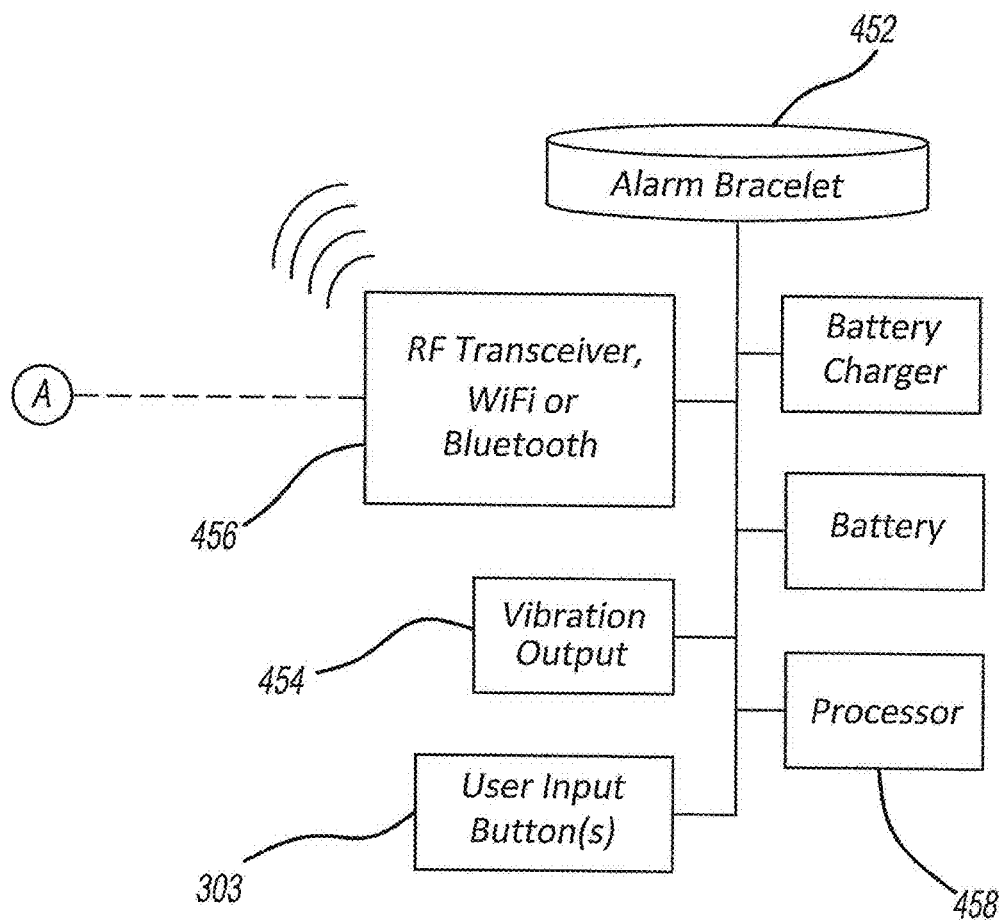
Figure 27C:
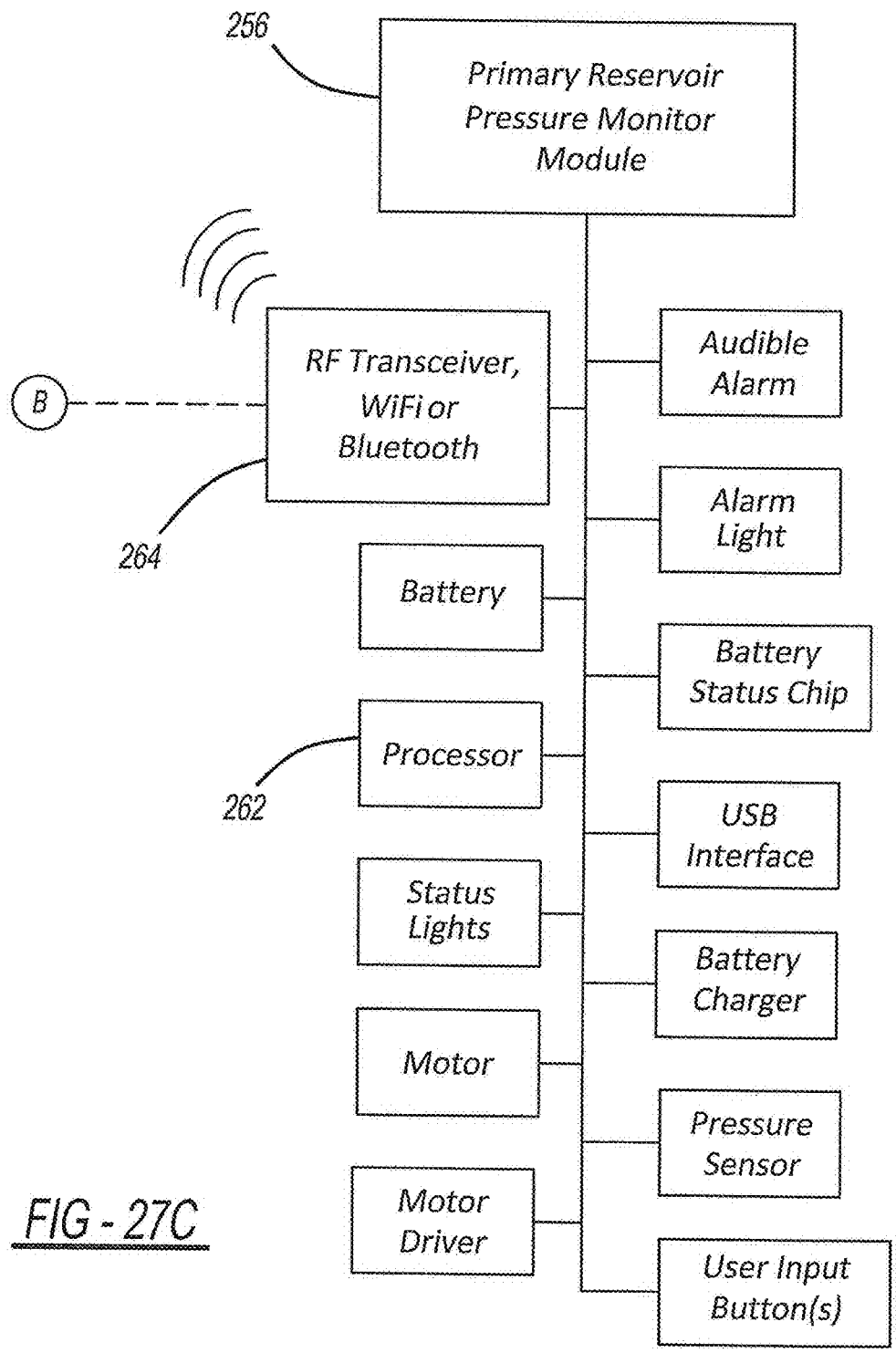
Figure 27D:
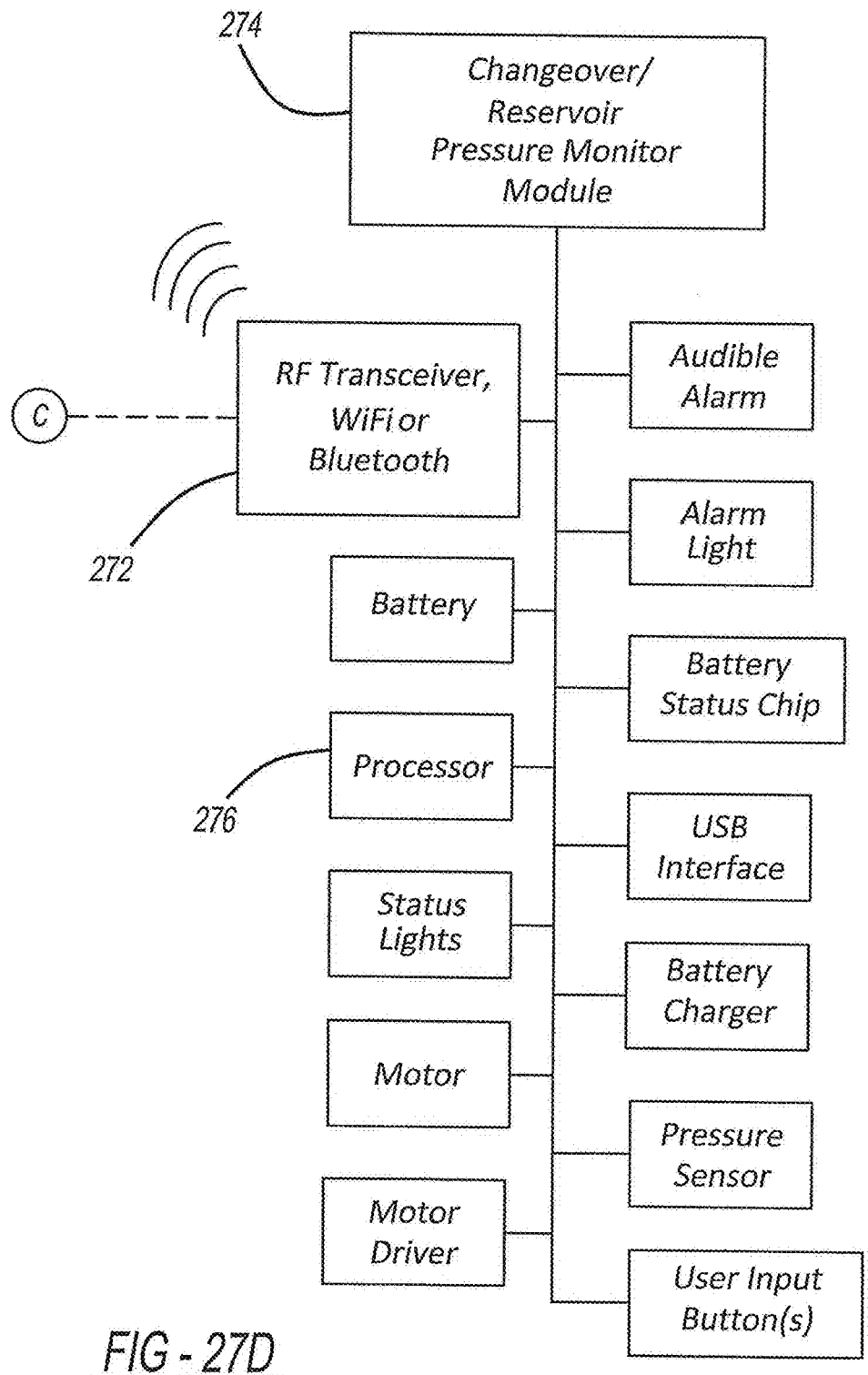
Figure 28A:
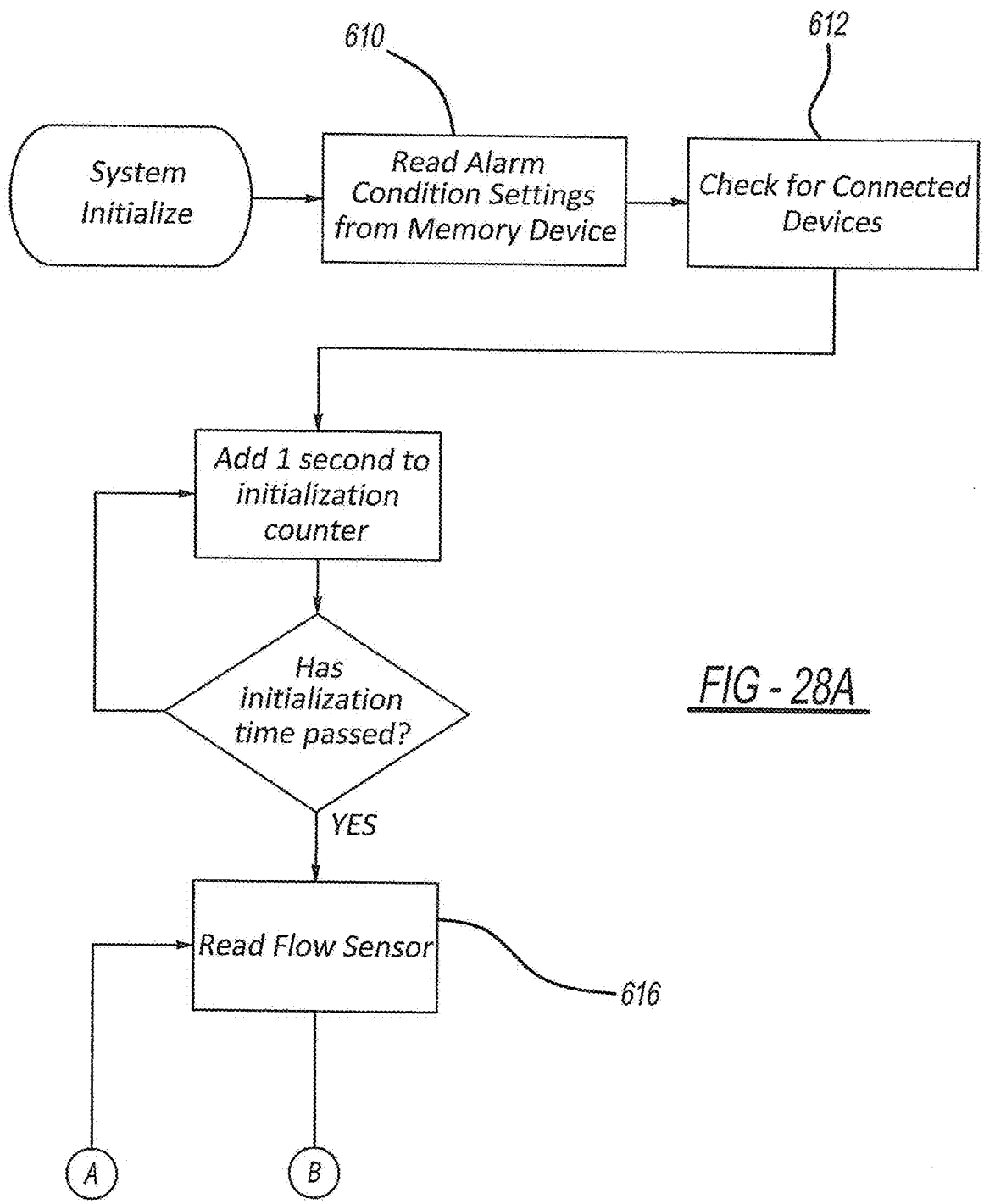
Figure 28B:
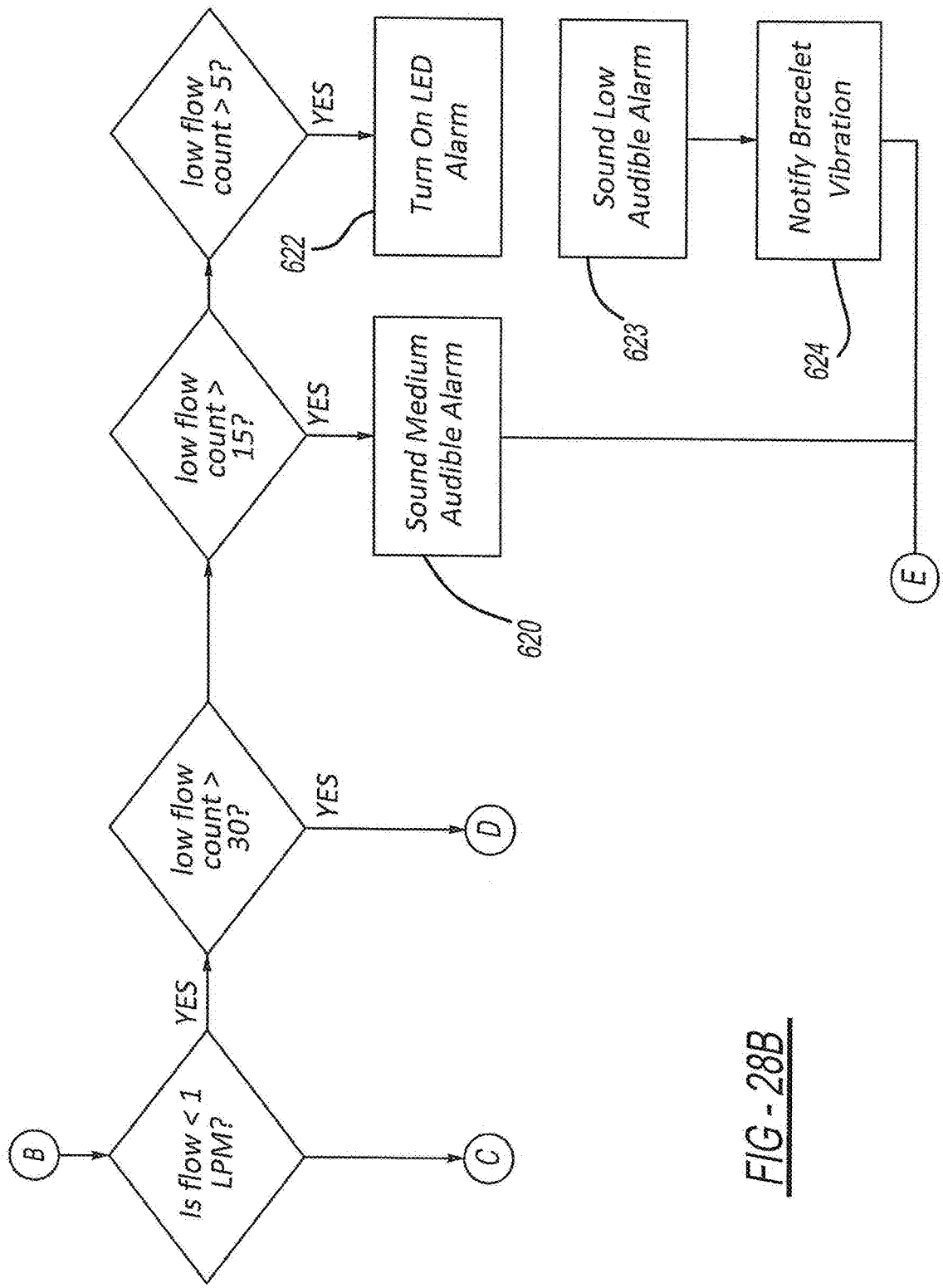
Figure 28D:
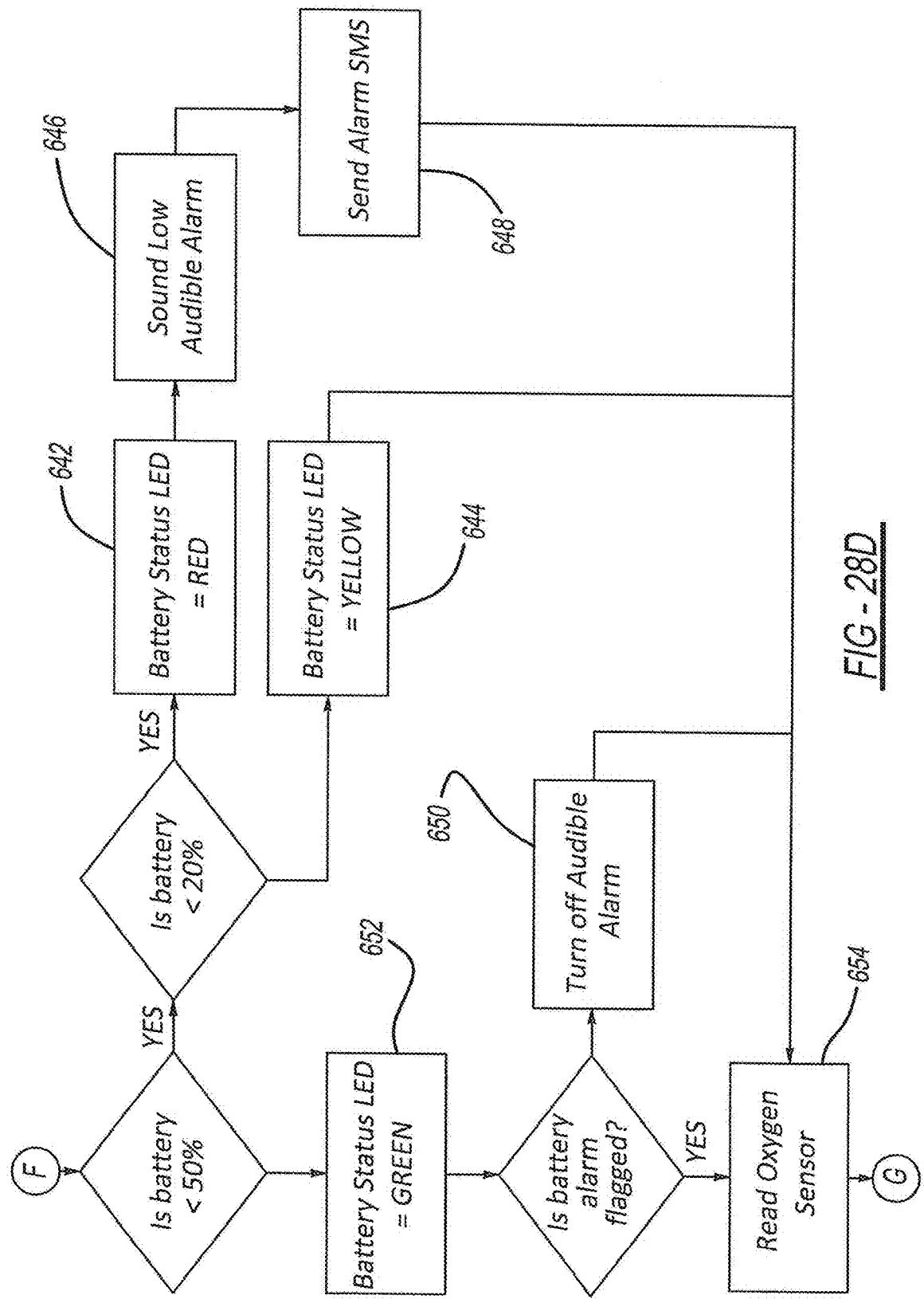
Figure 28E:
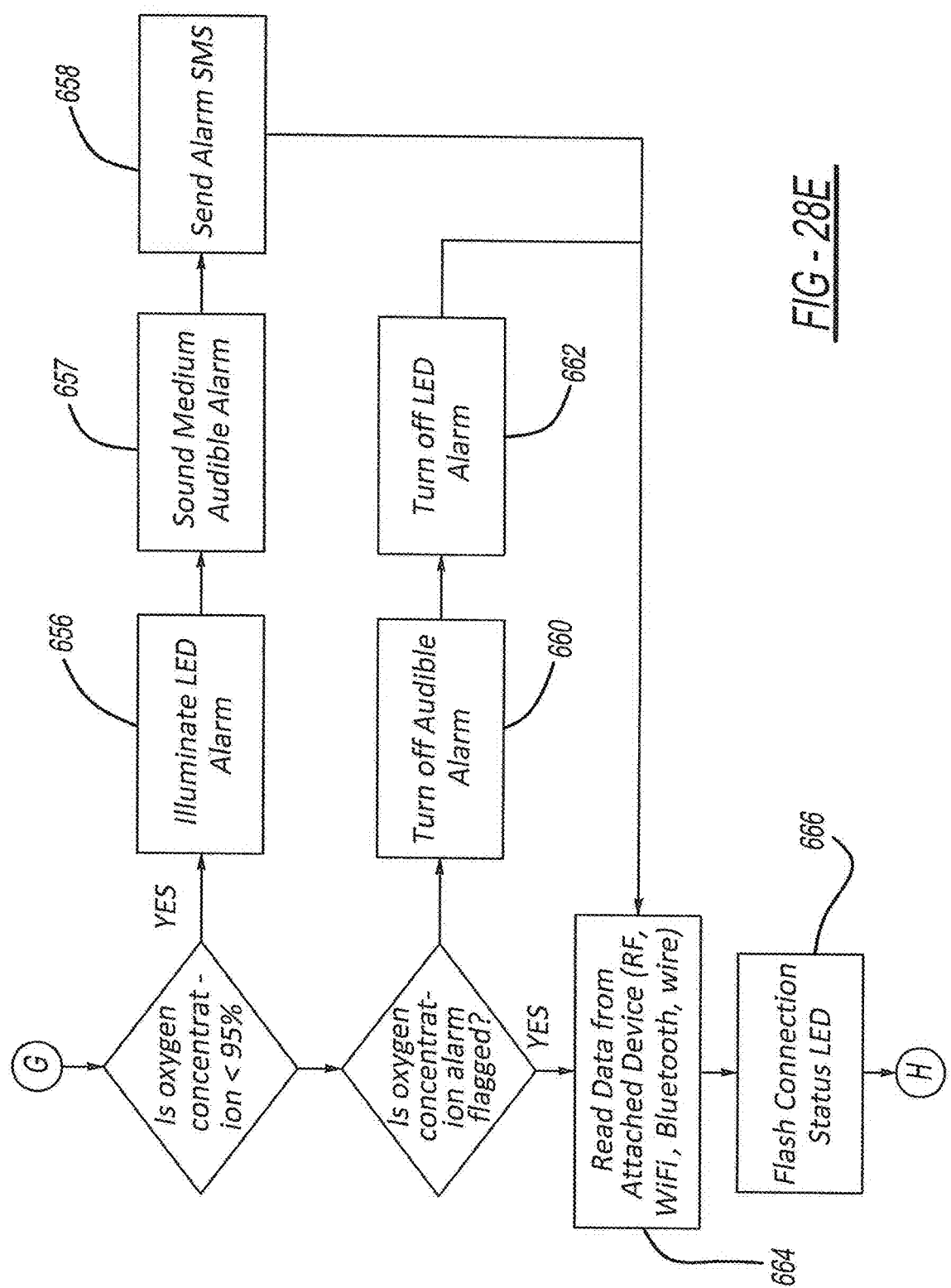

In an alternative embodiment of the gas supply warning and communication system 250, an oxygen analyzer module 412 is incorporated into the communication/flow monitor module 268 The resulting module, as shown in FIG. 26, is termed a communication/flow/oxygen monitor module 414. The communication/flow/oxygen monitor module 414 is especially useful in gas systems wherein the primary oxygen reservoir is an oxygen concentrator 416. The oxygen analyzer module 414 is capable of determining and displaying the oxygen concentration of the pressurized gas column and of generates oxygen concentration error signals when the concentration value violates at least a predetermined limit, usually a lower limit.

In the preferred embodiment, the oxygen analyzer module 14 is employed in conjunction with the previously described gas flow sensor 294, the gas flow error signal generator 296, and their associated circuitry. This combination provides the capability of detecting and reporting both gas flow and oxygen concentration malfunctions, which is especially useful in oxygen concentrator systems.

The oxygen analyzer module 412 includes an oxygen sensor 168 to measure an oxygen concentration in a column of gas by generating an output voltage proportional to an oxygen concentration, and a voltmeter 172 operatively connected to the oxygen sensor 168. The voltmeter 172 calculates an oxygen concentration value from the output voltage as previously described for the gas flow and pressure error alarm device 20. Preferably, the voltmeter 172 also displays the oxygen concentration value in a digital oxygen display 418. The oxygen analyzer module 412 also includes an oxygen concentration error signal generator 420 operatively connected to the voltmeter 172. Both the oxygen sensor 168 and the oxygen concentration error signal generator 420 are operatively connected to the central microprocessor 270, which records oxygen concentration data and oxygen concentration error signals in the central event memory 282. In response to the reception of an oxygen concentration error signal, the central microprocessor 270 actuates an oxygen alarm indicator 422, which can be a visual signal such as an LED, an audible signal, or both. In the preferred embodiment, the central microprocessor 270 also generates a changeover signal which is conveyed to the central transceiver 266 for transmission to the changeover/reservoir pressure monitor module 274. The error alarm signals, changeover signals, oxygen concentration data, and oxygen analyzer status indications all recorded as event records in the central event memory 282, for transmission or downloading to computers, mobile devices, web servers, and the like, as previously described.

Figure 25:
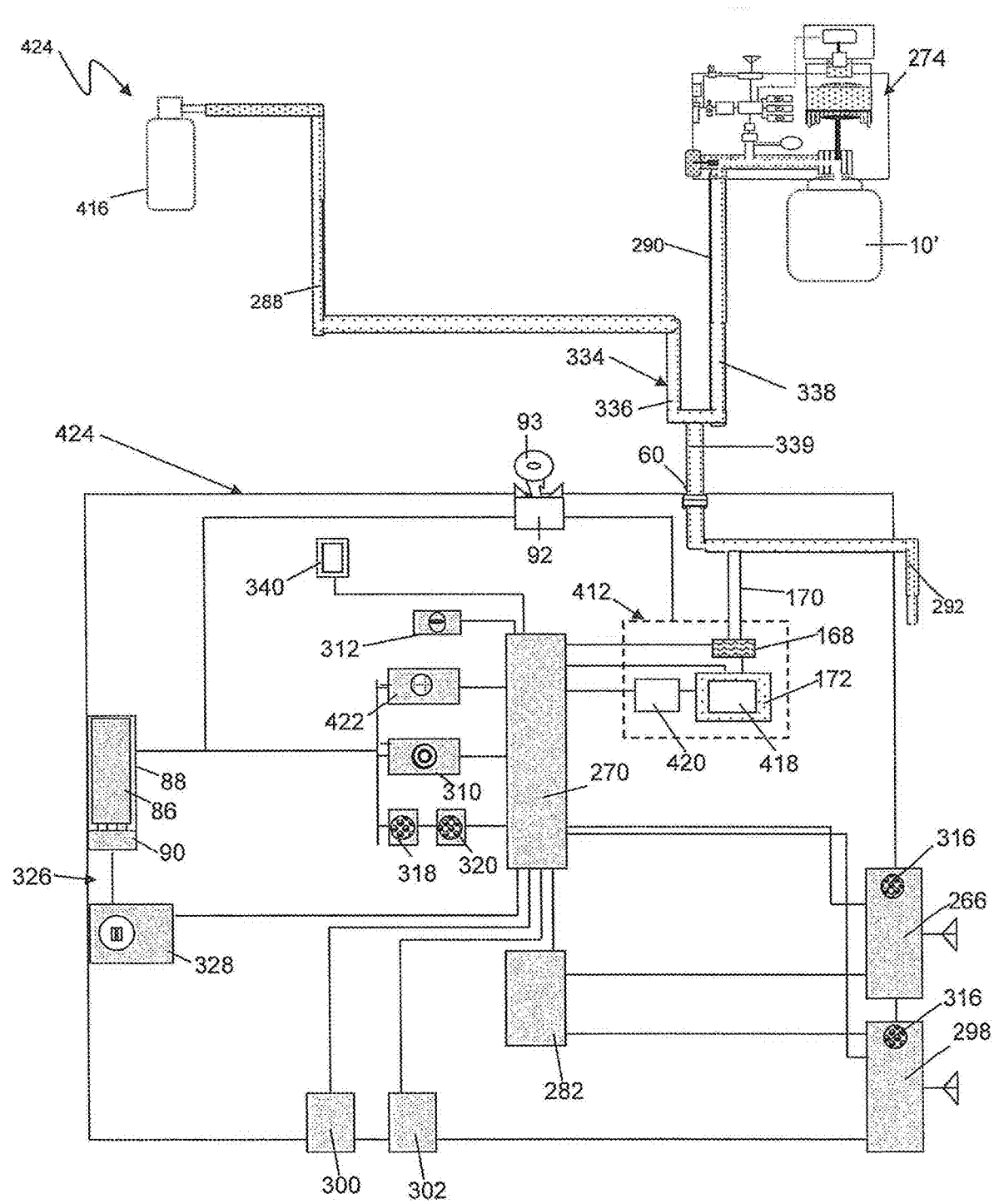
FIG. 25 shows a semi-schematic frontal view of a communication/oxygen monitor module according to the present invention.

The oxygen sensor 168 can be situated either upstream or downstream from the gas flow sensor 294. In the example shown in FIG. 25, the oxygen sensor 168 is downstream of the gas flow sensor, in gas tight engagement with the gas flow outlet 332 of the gas flow sensor 168. The engagement is preferably made through a T shaped connector 160 engaged to the previously described inlet manifold 334. The T shaped connector 160 includes an upstream port 162 engaged to the gas flow outlet 322, a bypass port 164 to admit the gas column to the oxygen sensor 168, and a downstream port 166 engaged to the downstream path 292 leading to an end use appliance.

An alternative embodiment of the communication/flow/ oxygen monitor module 414, termed a communication/ oxygen monitor module 424, does not include gas flow measurement and warning capability. The oxygen sensor 168 is directly engaged to the inlet manifold 334, as shown in FIG. 26. The communication/oxygen monitor module 424 does not include a flow gas flow sensor 168, a voltmeter 172, a gas flow error signal generator 296, a gas flow error alarm indicator 344, and the central microprocessor 270 need not be capable of receiving and recording gas flow data and gas flow error signals, actuating gas flow error indicators, or driving a digital gas pressure display.

The present invention also provides a vibrating bracelet 452, which serves as an alarm indicator. That is, the vibrating bracelet 452 is actuated as a reservoir pressure error alarm indicator 310, a gas flow rate error alarm indicator 244, or an oxygen concentration error alarm indicator 422. The vibrating bracelet 452 applies a vibration generated by a vibration output device 454 to a wrist or other body part of a user of the system 250. The vibrating bracelet 452 is preferably actuated by error signals generated by the central microprocessor 270. Vibrating bracelets 452 are commercially available and are readily adapted for actuation in response to any of the previously described error signals generated by the system 250. A suitable vibrating bracelet is the Vybe™ wristband available from www.wearvybe.com.

As shown in FIGS. 27A-27D, a vibrating bracelet typically includes a vibration output device 454, a battery 86, battery charger 258, user input buttons 303, and a wireless bracelet transceiver 456, preferably a wireless RF, Wi-Fi, or Bluetooth® transceiver. A bracelet microprocessor 458 regulates the routing of error signals to the vibration output device 454 and the transmission of event records to the central event memory 282 at the communications/flow module 268.

The present invention provides methods for controlling the operation of the system 250, preferably in the form of a processor-implemented method, such as a software application. The methods include routines for the automatic and manual control of the settings, valve operation, and data collection and storage for all phases of operation of the system 250. An exemplary software application encodes instructions for performing at least a flow monitor routine for controlling the communication/flow monitor module 268, and a pressure monitor and reservoir changeover control routine, for controlling a changeover/reservoir pressure monitor module 274.

An exemplary flow monitor control routine is shown in FIGS. 28A-28F. The flow monitor control routine begins with an initialization subroutine, in which flow rate alarm settings are read by the central microprocessor 270 from a memory device (step 610), connections between the communication/flow monitor module 268 and other components of the system 250 are confirmed (step 612), and a preset initialization time is completed (step 614). This is followed by a flow sensing and alarm subroutine, in which flow rate data values are read from the gas flow sensor 294 as flow counts (step 616). If the flow count is below at least one predetermined limit, at least one gas flow error alarm is activated. Specific alarm patterns can be activated in response to specific shortfalls relative to the predetermined limit (steps 618, 620, 622, 623, and 624). If the shortfall is sufficiently great, a changeover signal is transmitted to the changeover/reservoir pressure monitor module 274 to cause the opening of the reserve gas reservoir 10 (step 626). In this case, the reserve gas reservoir 10' is flagged as being in an open condition (step 628), and an alarm message is sent to remote users via the telephonic module 298 (step 630). If the reserve gas reservoir is already flagged as open, as would be the case for an exhausted reserve gas reservoir, an alarm is sent via the telephonic module 298 to warn users of the problem (step 632). If the flow count is not below at least one predetermined limit, or if the flow alarms have been flagged, then the flow count is reset (step 634) and the gas flow rate error alarms are deactivated (steps 636, 638).

A battery status check routine in next initiated, in which battery status is read (step 640). If battery charge is below a predetermined limit, then at least one battery status alarm indicator is activated, with specific indicators activated in response to specific battery charge shortfalls (steps 642, 644, 646, and 648). If the battery charge alarm responses have been flagged, the alarm indications are deactivated (step 650). If the battery charge is at or above a predetermined limit, a green battery status is activated (step 652).

If an oxygen sensor 168 is present, then an oxygen concentration and alarm subroutine is next initiated. Oxygen concentration data values are read from the oxygen analyzer module 412 (step 654). If the oxygen concentration is below at least one predetermined limit, at least one oxygen concentration error alarm indication is activated, including audible and visible oxygen concentration error alarm indicators 422 (steps 656 and 657). An oxygen concentration error alarm signal to remote devices and optionally to the changeover/reservoir pressure monitor module (step 658). If the oxygen concentration is not below at least one predetermined limit, or if the oxygen alarms have been flagged, then oxygen concentration alarms are deactivated (steps 660, 662), and a data storage subroutine in initiated. A connection to at least one remote device is established (steps 664 and 666), gas flow and oxygen concentration data and event records are saved in the central event memory 282 (step 668) and transmitted, preferably by a Wi-Fi or Bluetooth® connection, to a remote device (steps 670, 672). If a reset button has been pressed then all flags are reset (steps 673, 674). The subroutine then cycles back to the step of reading flow rate data values from the gas flow sensor 294 (step 616).

Figure 29A:
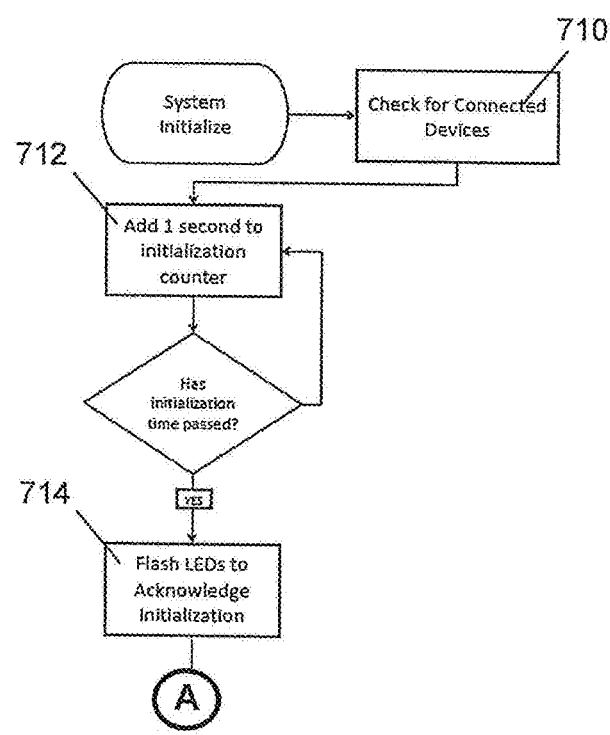
FIG. 29A, FIG. 29B and FIG. 29C show a flow chart of an exemplary pressure monitor and reservoir changeover control routine.
Figure 29B:
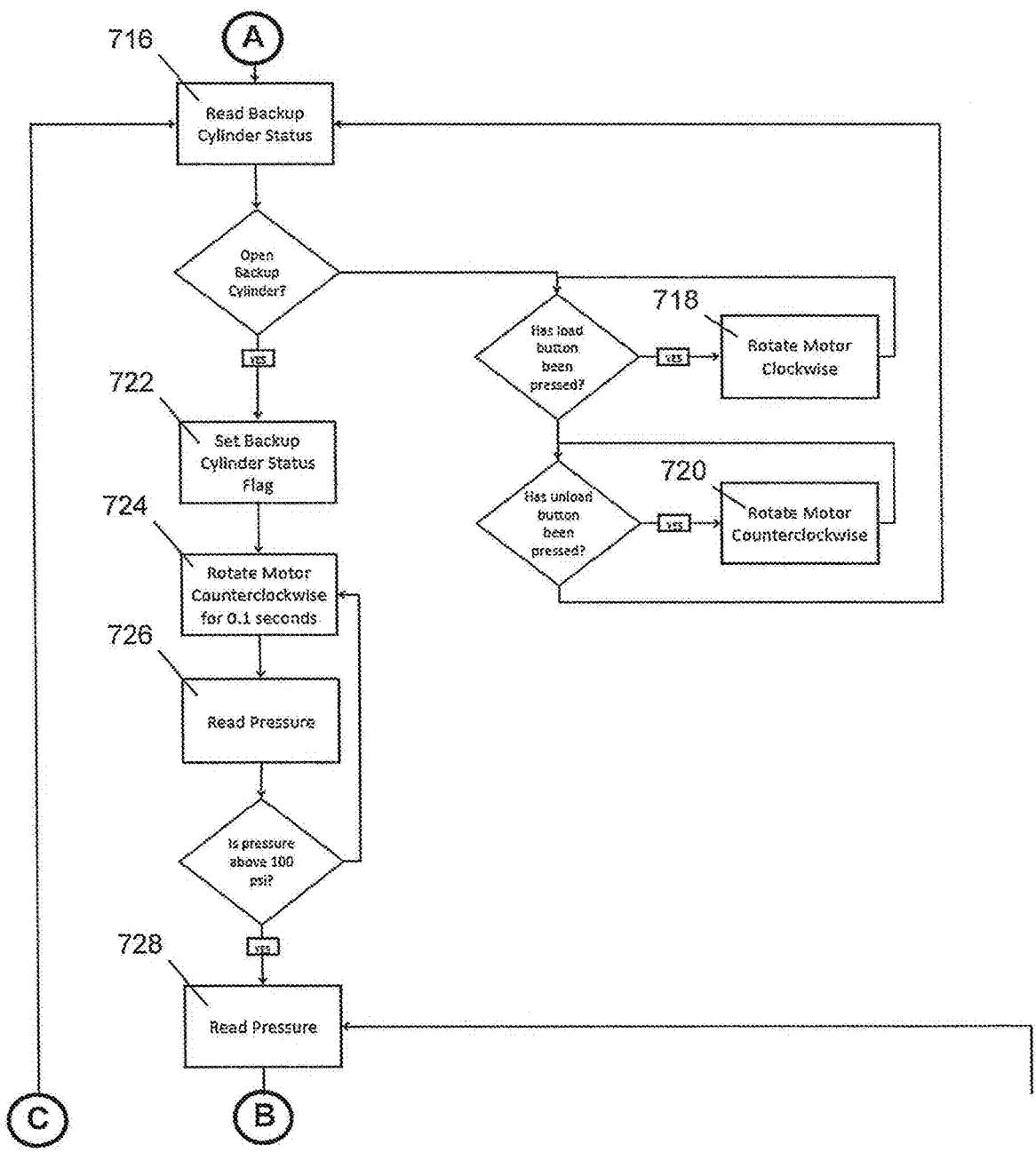
Figure 29C:
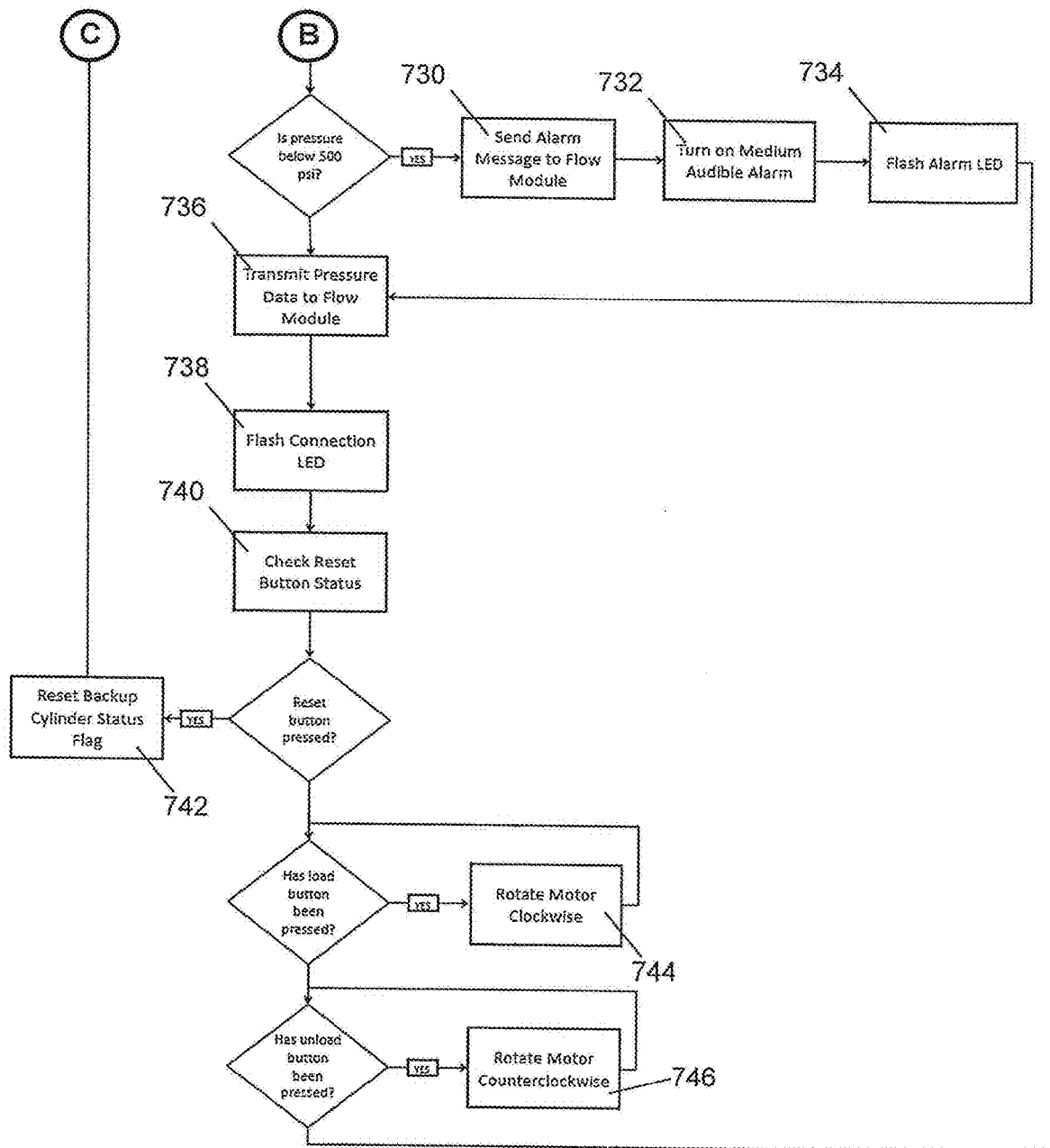

An exemplary pressure monitor and reservoir changeover control routine is shown in FIGS. 29A-29C. This routine is triggered when a reservoir changeover signal is received by changeover/reservoir pressure monitor module 274. An initialization subroutine is executed, in which connection between the changeover/reservoir pressure monitor module 274 and other devices in the system 250 is confirmed (step 710) and a preset initialization time is completed and indicated (steps 712 and 714). A reservoir loading subroutine is next initiated. The loaded or unloaded status of the reserve gas cylinder 10' is determined (step 716), and the reservoir changeover device 252 is actuated to apply appropriate valve opening or valve closing torque to the main valve 38' to bring the reserve gas cylinder 10' into an initial closed condition (steps 718 and 720). A reserve cylinder status flag is set (step 722). The reservoir changeover device 252 is actuated to apply valve opening torque to the main valve 38' of the reserve gas cylinder 10' in 0.1 second increments until a threshold pressure is sensed by the reservoir pressure sensor (steps 724 and 726).

A reservoir pressure sensing and alarm subroutine is then initiated. Pressure data values are read from the reservoir pressure sensor as psi (step 728). If the reservoir pressure is below at least one predetermined limit, a reserve reservoir pressure error signal is transmitted to the communications/flow monitor module 268 (step 730), and at least one reserve reservoir pressure alarm indication is activated (steps 732, 734). Reservoir pressure data values are also transmitted to the communications/flow monitor module (steps 736 and 738). The reservoir pressure sensing and alarm subroutine continues until it is determined that a reset, load, or unload button is pressed by a user (step 740). If a reset button has been pressed, then a reset/load/unload subroutine is initiated, in which the cylinder status flag is reset (step 742), and the subroutine cycles back to the step of determining the loaded or unloaded status of the reserve gas cylinder 10' (step 716). If a load or unload button has been pressed, then the reservoir changeover device 252 is actuated to apply valve opening or valve closing torque to the main valve 38', depending on which button has been pressed (steps 744 and 746).

Additional routines, such as routines for generating a reservoir changeover signal in response to a primary reservoir pressure error signal, are readily designed by one skilled in the art, according to the pattern set by the previously described routines. Specific steps of the subroutines can be locked, so that only authorized users such as hospital staff can modify such parameters as alarm threshold settings and the downloading of data.

Figure 30:
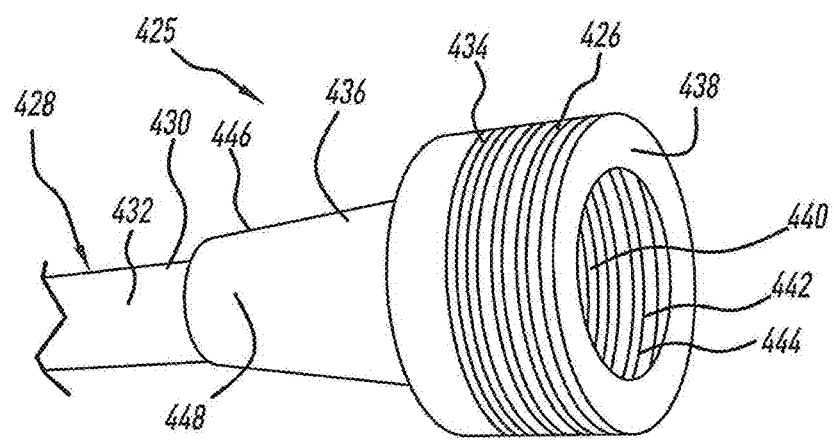
FIG. 30 shows a gripper tube according to the present invention having a V-shaped end.

The present invention also provides a gripper tube 425 having a gripping endpiece 426, for secure attachment to the outlet of a reservoir of gas or other fluid. As shown in FIG. 30, the gripper tube 425 includes a tube member 428 including a tube wall 430 defining a tube lumen 432. The gripping tube 425 has at least a first free end including the gripping endpiece 426. The gripping endpiece 426 includes a distal annular member 434 and a proximal tapering member 436.

The annular member 434 includes an endpiece wall 438 defining an endpiece lumen 440, which has a diameter greater than the diameter of the tube lumen 432. The inside surface of the endpiece wall 438 includes a plurality of grooves 444 which define a plurality of ribs 446 projecting into the endpiece lumen 440. The ribs 446 provide gripping force about an outlet inserted into the endpiece lumen 440. The tapering member 436 includes a tapered wall 446 defining a tapered lumen, 448. The proximal end of the tapered wall 446 is continuous with the tube wall 430, and the distal end of the tapered wall 446 is continuous with the endpiece wall 438. The diameter of the tapered lumen 448 diminishes proximally, approximating the diameter of the endpiece lumen 440 at its distal end, and approximating the diameter of the tube lumen 432 at its proximal end The tube member 428 can have a second free end which can include a second gripping endpiece (not shown) having proportions similar or dissimilar to the previously described endpiece 426. Alternatively, the second free end of the tube member 428 can include another end modification (not shown) or it can be unmodified. The tube member 428 can also have no second free end and terminate in another device, such as a nasal cannula or mask.

The tube member 428 and gripping endpiece 426 can be fabricated as a single unit, or alternatively can be fabricated separately and assembled into a gripping tube 425. Assembly include permanent fixation of a gripping endpiece 426 to a tube member 428, or a gripping endpiece 426 can be reversibly connected to a tube member 428, with the tube wall 430 being inserted into the tapered lumen 448 or the tapered wall 446 inserted into the tube lumen 432. Alternatively, the tube member and gripping endpiece 426 can be interlocked by any gas or fluid-tight engagement means known in the art.

The tube member 428 and gripping endpiece 426 can be constructed of the same materials or can be of dissimilar materials. The gripping endpiece 426 is preferably composed of a flexible elastic material such to provide elastic force upon the ribs 444. Suitable flexible materials include but are not limited to silicone, polyvinyl chloride, or a thermoplastic elastomer.

The tube member 428 can be composed of either a flexible elastic material, or of a rigid material such as nylon, polycarbonate, or a metal.

Figure 31:
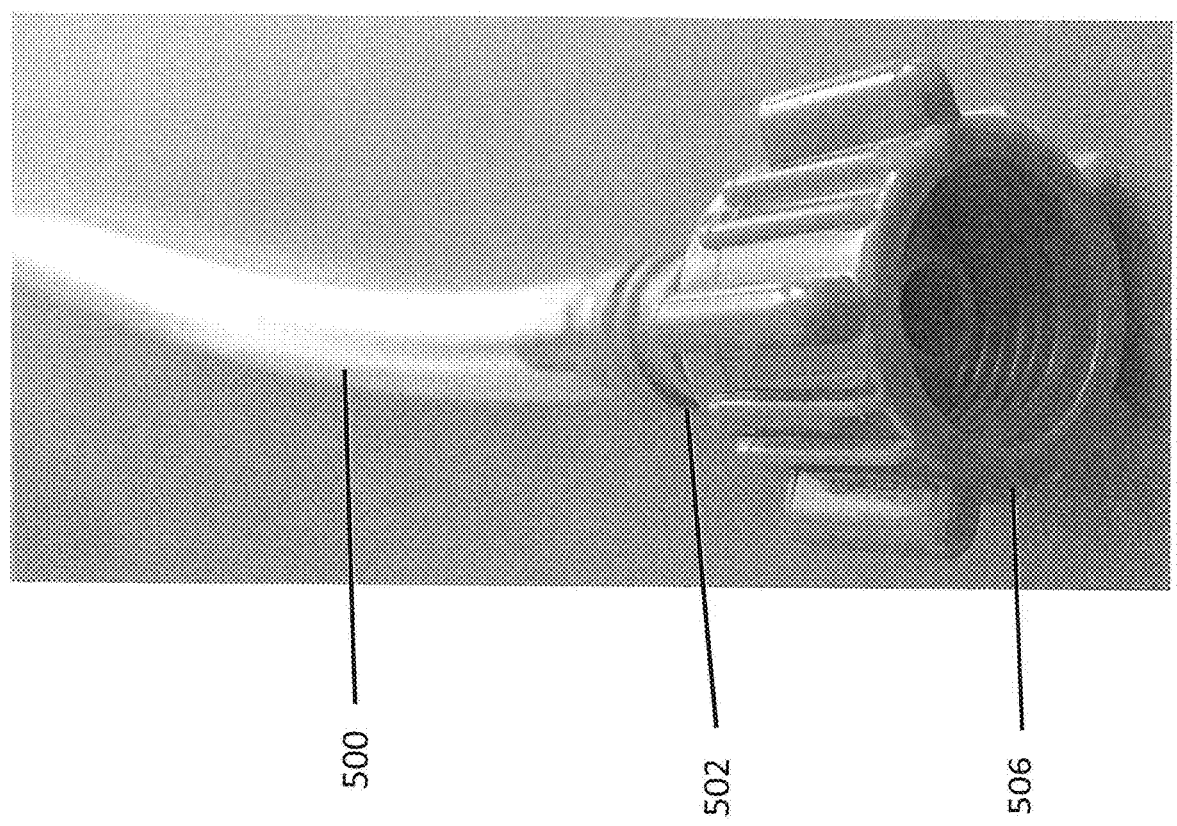
FIG. 31 shows a tube with a twist on nipple end.
Figure 35:
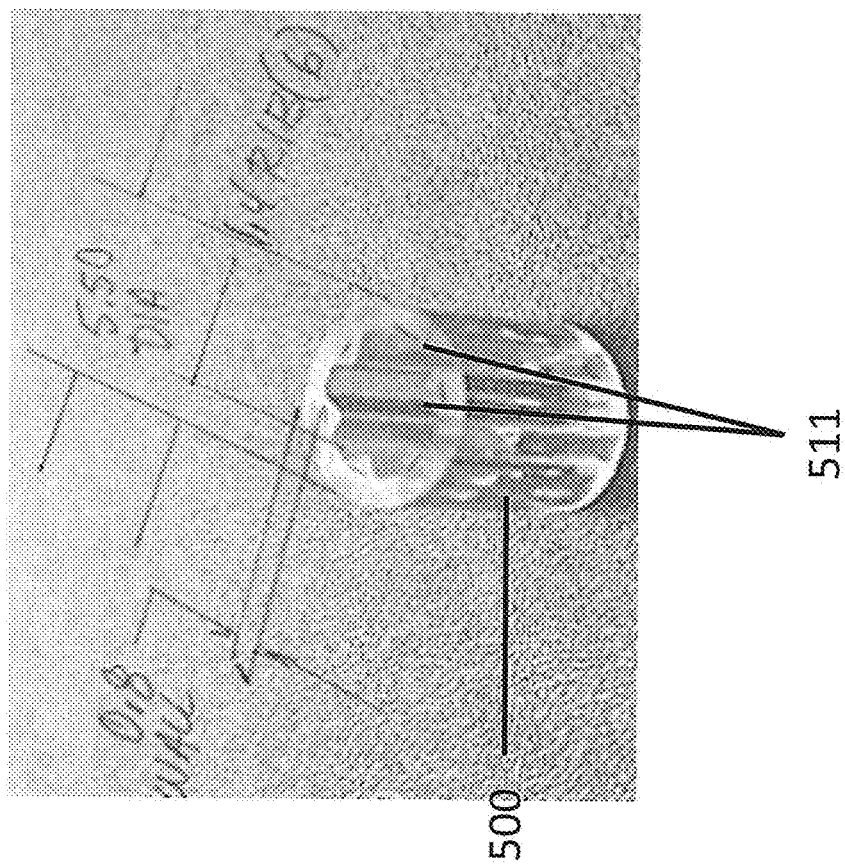
FIG. 35 shows a cross-section of a gas path tube.

Any of the tubing 500 used in the present invention, especially for the first upstream gas path 288, the second upstream gas path 290, and the downstream gas path 292 can have a variety of connector ends 502. A universal connector 504 can be used for oxygen shown in FIG. 32, and can be made of materials such as flexible PVC with a vinyl tip, or polyolefin. The universal connector 504 can be connected to a flowmeter, regulator, or oxygen concentrator and can be used on any oxygen source. A twist-on nipple 506 can be used made of plastic or metal, as shown in FIG. 31, and is useful for preventing accidental disconnection. A V-shaped end (gripper tube 425 with gripper endpiece 426, shown in FIG. 30) can also be used to prevent disconnection. The connector ends 502 can also include flanges on an inside surface to help further prevent disconnection (shown at 440, 442, and 444 in FIG. 30, and also referred to as ribs or grooves above). Many oxygen users continually check to make sure they are receiving oxygen and the connector ends 502 help with patient safety. The connector ends 502 can be located on a single end of the tubing 500 with a device on the opposite end (such as a nasal cannula 510) or on both ends. A cross-sectional view of tubing 500 can be seen in FIG. 35 with representative dimensions. This cross-sectional view is of regular tubing designed with ribs 511 that prevent the tubing from being pinched together and preventing flow therethrough. Any suitable size tubing 500 can be used, and any lengths and diameters can be used depending on the use. The tubing 500 can be made of flexible polyvinyl chloride (PVC), crush resistant and flexible PVC, or any other suitable material. The tubing 500 can also include additional elements such as sliding components (lariats) made of polyolefin, luer lock connectors (male and female, made of rigid thermoplastic), and Y connectors made of flexible PVC.

Figure 38:
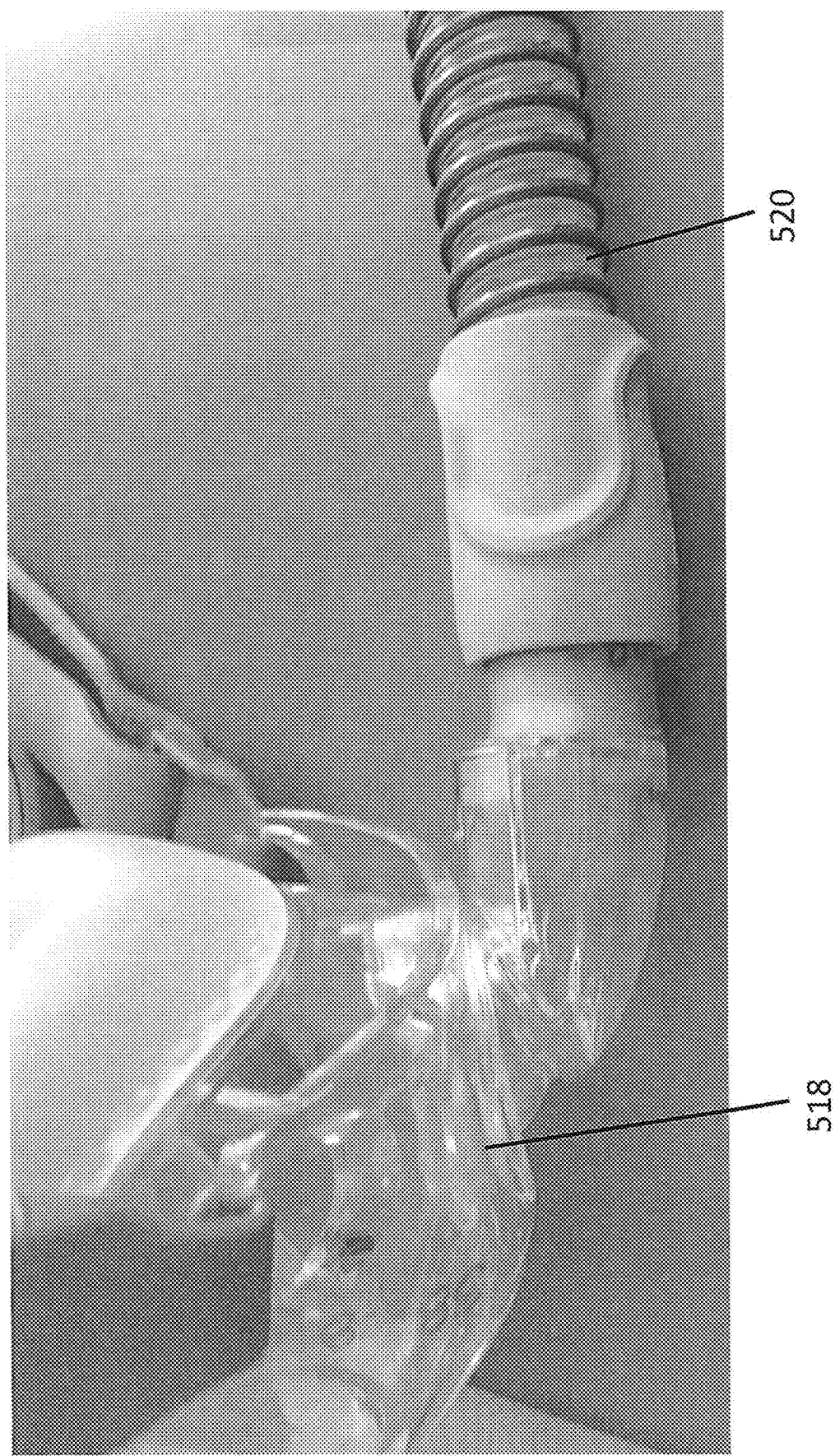
FIG. 38 shows a CPAP mask and tube.
Figure 39:
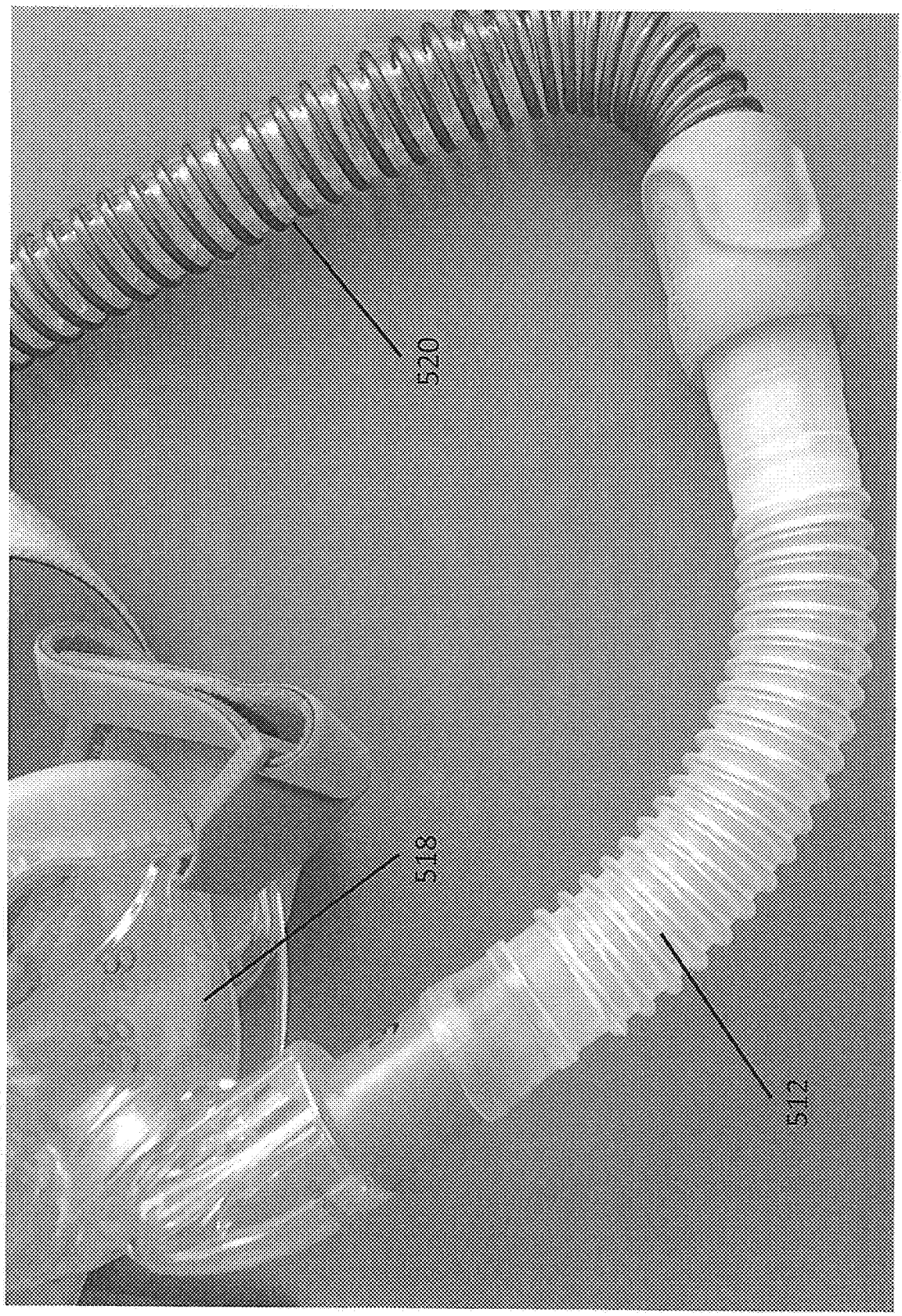
FIG. 39 shows a CPAP mask and tube.

Nafion® (PermaPure) tubing 512 can be integrated and operatively connected into the tubing 500 just below the nasal cannula 510 (shown in FIGS. 32-34, the Nafion® tubing 512 appears woven compared to the regular tubing 500). Nafion® is a copolymer of polytetrafluoroethylene and perfluoro-3,6-dioxa-4-methyl-7-octene-sulfonic acid. It is manufactured as a clear plastic and has unique water absorption properties that allow it humidify air or gas. Using Nafion® tubing 512 allows oxygen in the tubing 500 to be the same humidity as the room air in the environment. Any of the connector ends 502 described above can be used. The Nafion® tubing 512 can be designed at a width to integrate with wider and thicker CPAP tubing 518 in order to humidify air from a CPAP machine/masks 520, shown in FIGS. 38 and 39. Any suitable size Nafion® tubing 512 can be used, and any lengths and diameters can be used depending on the use. The Nafion® tubing 512 can also include ribs 511 as described above. The advantage of using Nafion® tubing 512 is that it eliminates the need for a water source to humidify the oxygen flowing to nasal cannulas and CPAP masks. Currently used humidification systems are bacteria traps. Using the Nafion® tubing 512 in the present invention can therefore reduce sinus infections in users, as well as nosebleeds and provides a portable solution.

Figure 36:
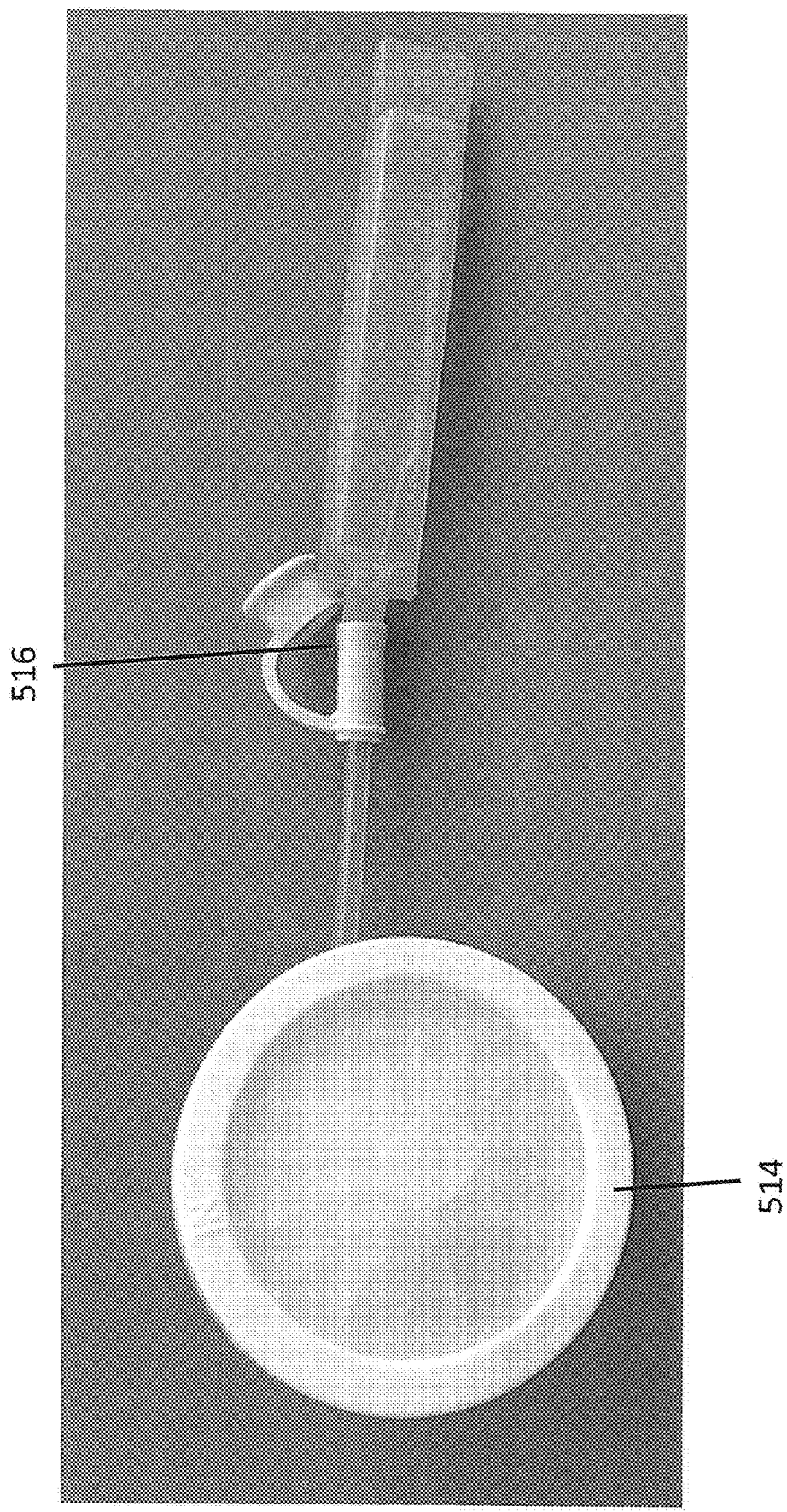
FIG. 36 shows a humidity filter.
Figure 37:
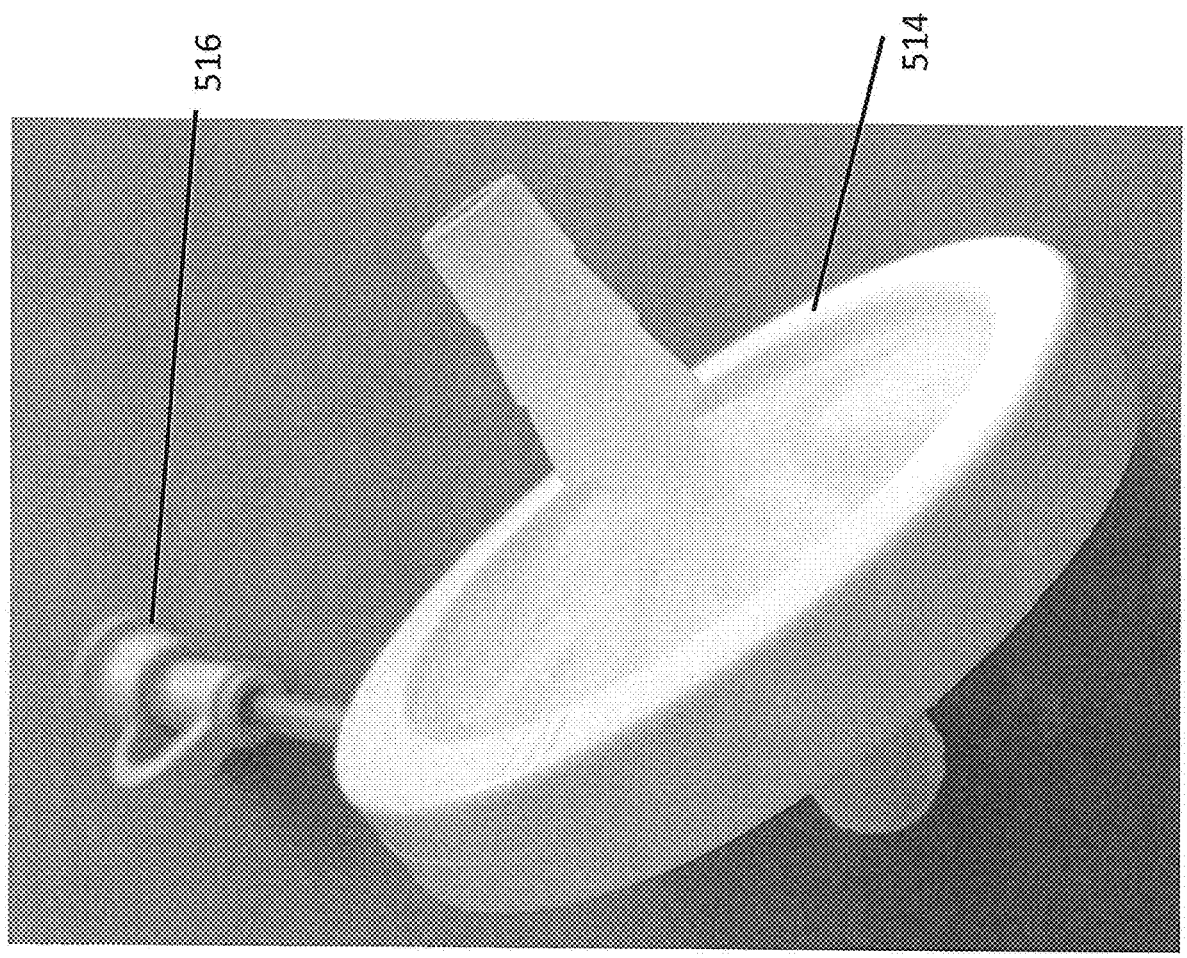
FIG. 37 shows a humidity filter.

Humidification of the oxygen in the tubing 500 can alternatively be accomplished by using a humidification filter 514 operatively connected thereto, as shown in FIGS. 36 and 37. The humidification filter 514 can be made of paper or foam and can be impregnated with hygroscopic salts, such as calcium chloride, to aid in the water-retaining capability. Sterile water can be added to moisten the humidification filter 514 through a port 516. The humidification filter 514 can include any suitable antimicrobial agents to reduce the risk of bacteria or fungus and/or the humidification filter 514 can be electrostatic. The humidification filter 514 also reduces nosebleeds in users and is a portable solution.

The present invention therefore provides for a method of increasing humidity in a gas line (downstream gas path) in a gas supply warning and communication system described above, by flowing gas through a downstream gas path tubing that increases humidity to an end use appliance. The tubing can either be the Nafion® tubing 512 or the tubing 500 with the humidification filter 514 as described above. The end use appliance can be the nasal cannula 510, oxygen mask (not shown) or a CPAP mask 520. The method can further include the steps of reducing side effects normally experienced with end use appliances such as nosebleeds and sinus infections.

Figure 32:
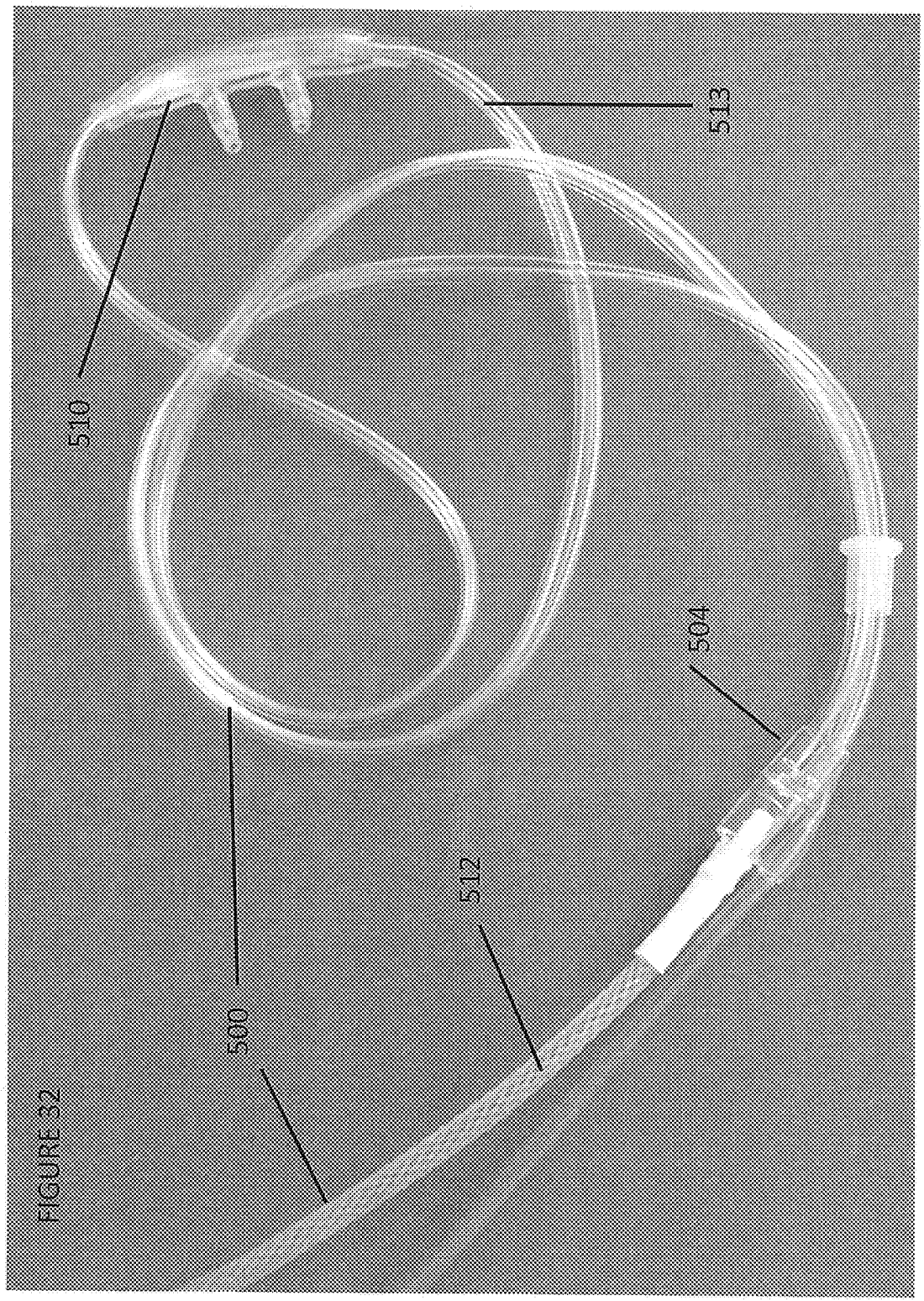
FIG. 32 shows a nasal cannula with Nafion® tubes.
Figure 33:
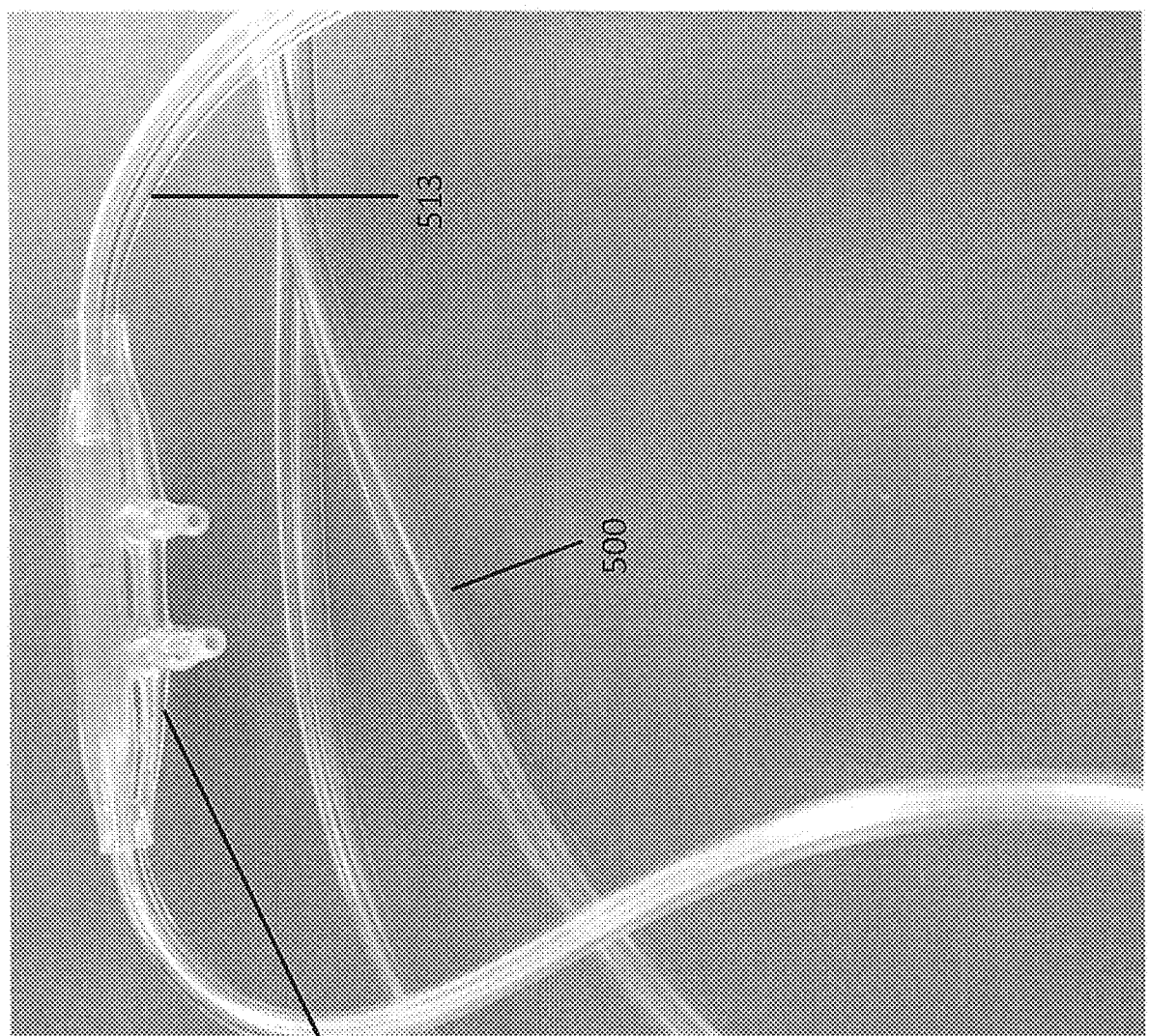
FIG. 33 shows a nasal cannula.
Figure 34:
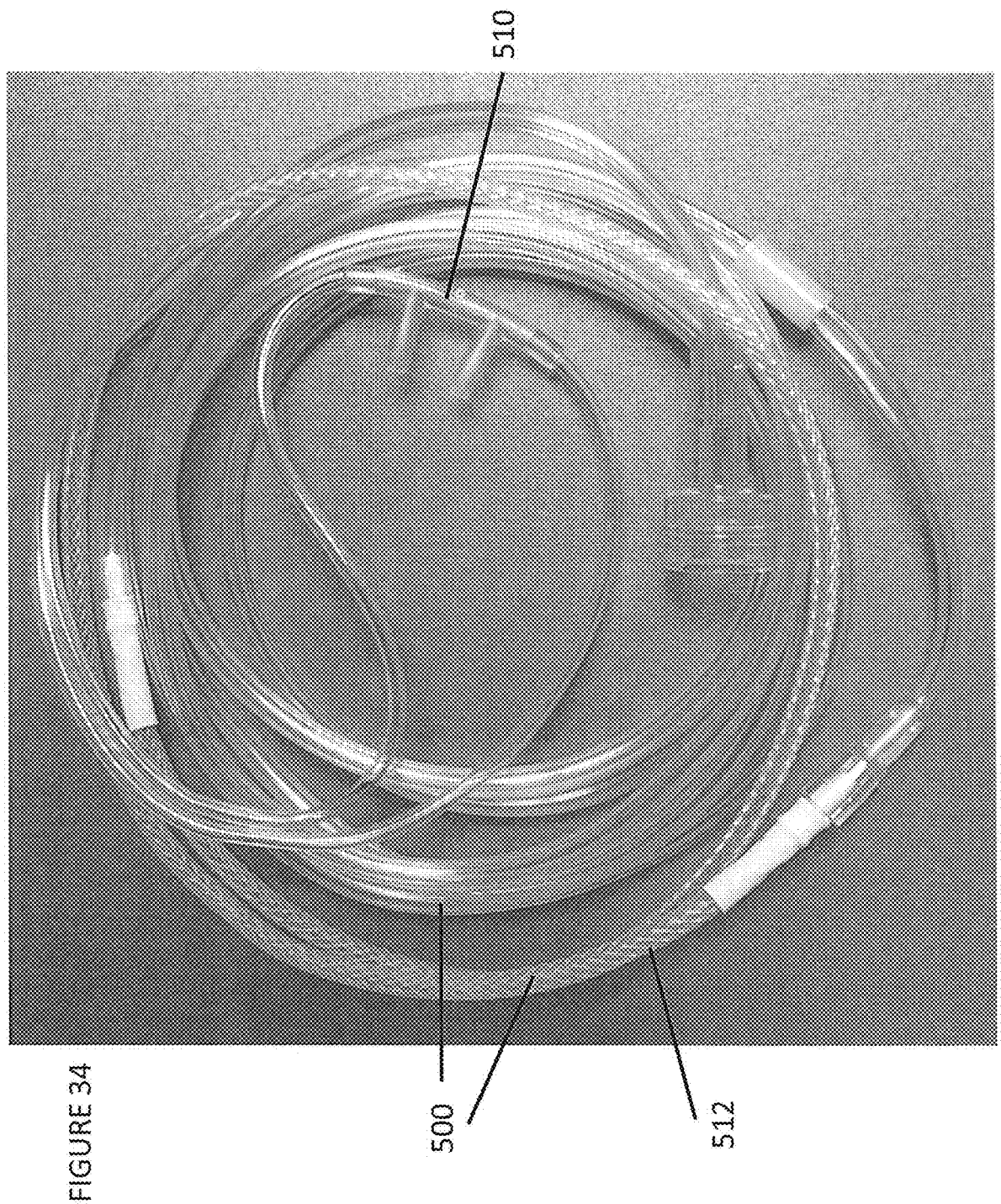
FIG. 34 shows a nasal cannula with Nafion® tubes.

An ETCO2 sampler or sensor 513 can be integrated with the tubing 500 or Nafion® tubing 512, especially with use of the nasal cannula 510 (the nasal cannula 510 can be an ETCO2 nasal cannula having a sampling tubing 513 as shown in FIGS. 32 and 33). The ETCO2 sensor 513 can measure the End Tital CO2 and these values can determine if the nasal cannula 510/oxygen is placed on the user's face correctly. The ETCO2 sensor 513 can read, display (on any suitable display), and transmit any necessary data to the systems of the present invention, and is in electronic communication with any central microprocessor 270, software, and any other necessary sensors in the system.

Figure 40:
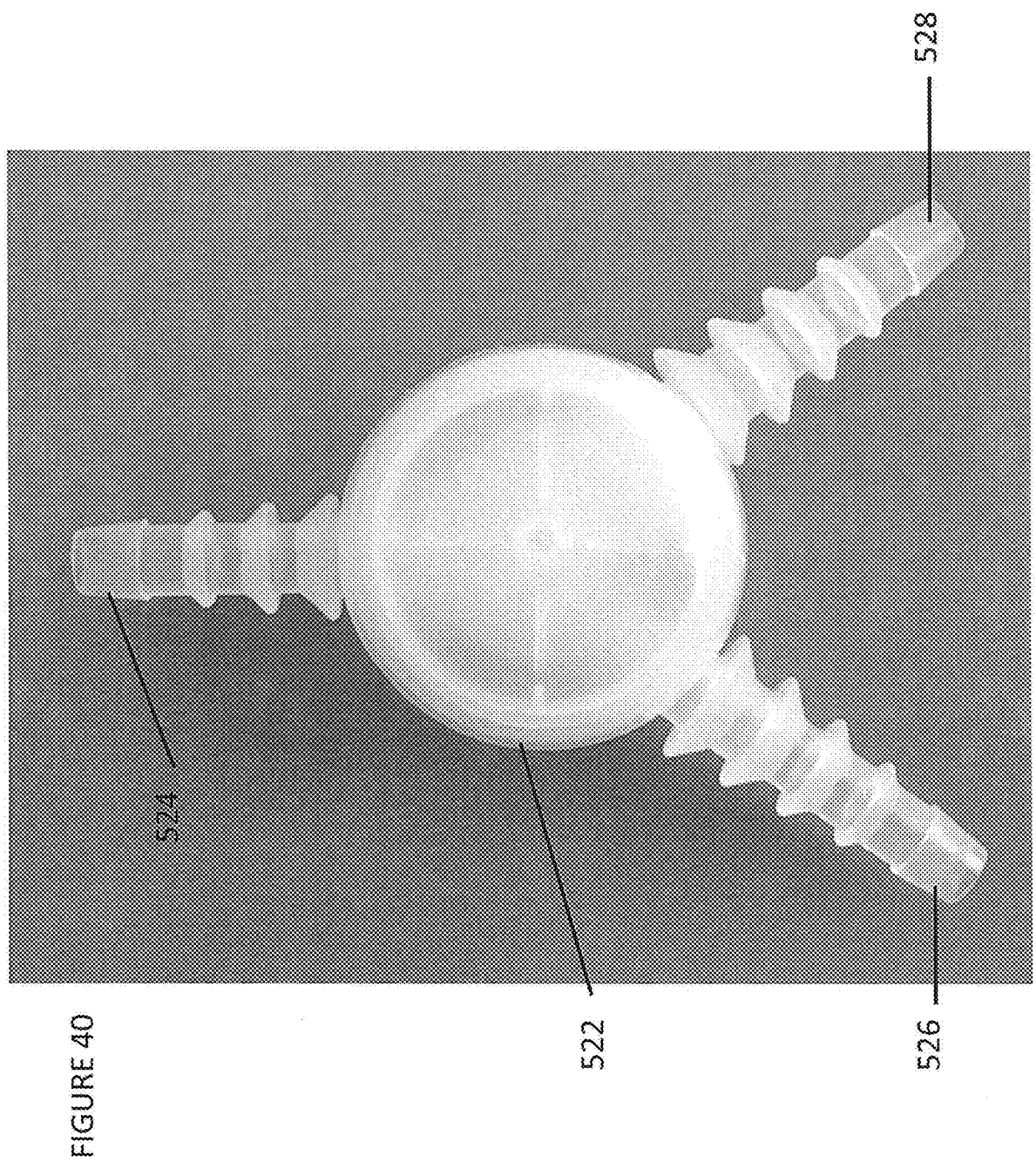
FIG. 40 shows a changeover tubing.

The present invention can also include a changeover flow diverter tubing 522, shown in FIG. 40, which is able to receive commands (by any suitable wireless or wired methods) from the motorized reservoir changeover device 252. The changeover flow diverter tubing 522 includes one outlet 524 and two inlets 526, 528 that are not open at the same time. One inlet 526 is in fluid connection with the primary fluid reservoir (primary cylinder 10') and one inlet 528 is in fluid connection with the reserve fluid reservoir (reserve gas cylinder '10). If there is any issue or problem with the primary fluid reservoir, an alarm is sent to change to the reserve fluid reservoir. The command can trigger a flow diverter that changes the flow coming from the primary fluid reservoir (primary cylinder 10') to the flow from the reserve fluid reservoir (reserve gas cylinder '10), i.e. closing inlet 526 and opening inlet 528. The changeover flow diverter tubing 522 simplifies adding the motorized reservoir changeover device 252 to the system and allows for easier changing to a back up fluid supply if needed.

Figure 41:
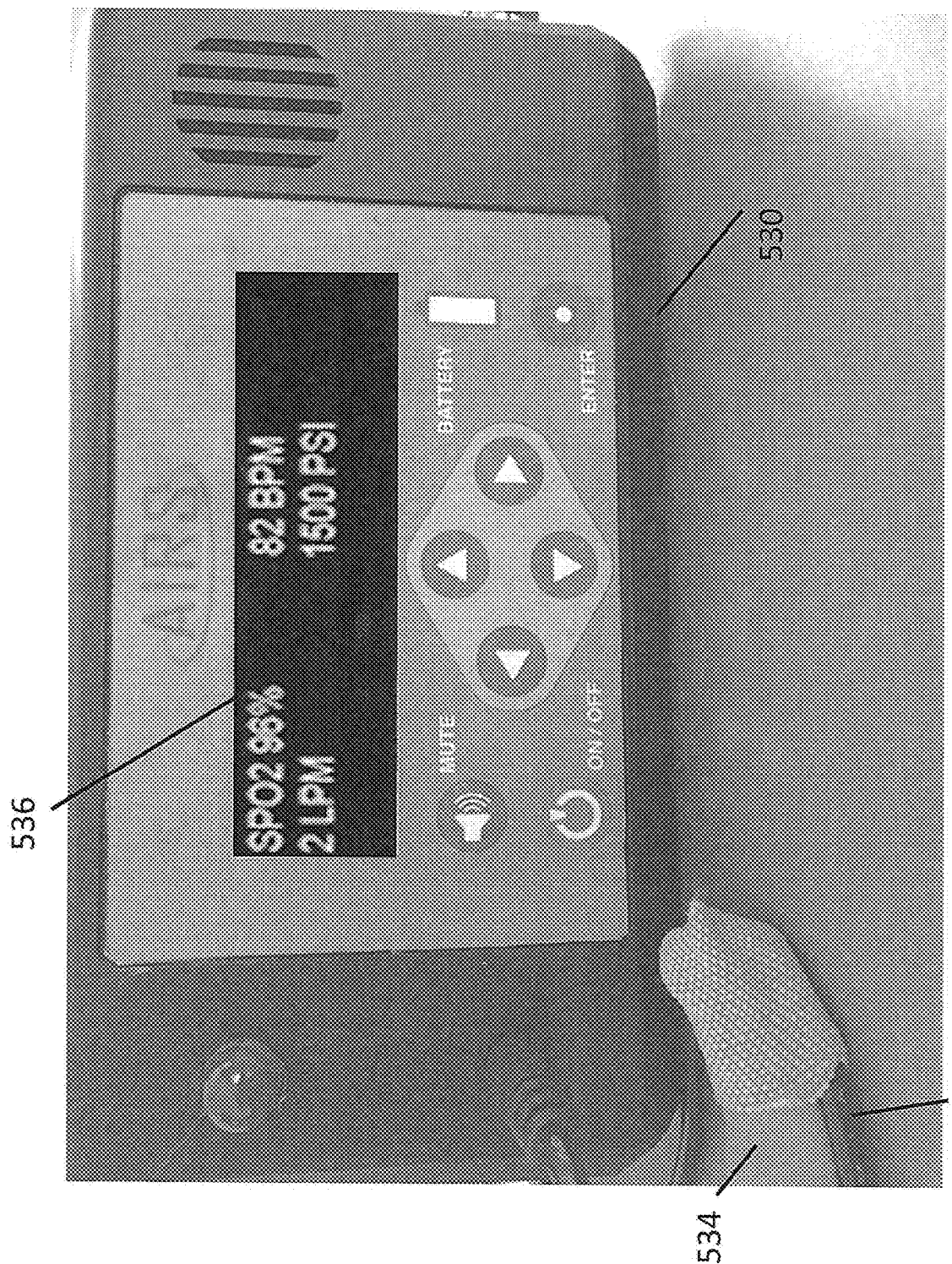
FIG. 41 shows a pulse oximeter.

The present invention can further include a pulse oximeter 530 that can monitor a patient's SPO2 and pulse, as shown in FIG. 41. A pulse oximeter 530 is commonly used in respiratory care. A probe 532 is removably attached to a patient's finger 534. The probe 532 can be a reusable finger probe or a disposable sticker probe. The probe 532 measures the oxygen saturation by comparing how much red light and infrared light is absorbed by the blood. The pulse oximeter is in electronic communication with the central microprocessor 270 to transmit data to any necessary software and display data on a display 536 (either on the pulse oximeter 530 or on any other part of the system).

While illustrative embodiments of the invention have been disclosed herein, it is understood that other embodiments and modifications may be apparent to those of ordinary skill in the art.

The invention claimed is:

1. A fluid supply warning and communication system including:
   a primary reservoir pressure monitor module in fluid tight engagement with an outlet of a primary fluid reservoir, for sensing primary reservoir pressure in a pressurized fluid system, and generating a primary reservoir pressure error signal in response to sensing a reservoir pressure data violative of at least one predetermined pressure limit,
   said primary reservoir pressure monitor module in fluid tight engagement with a first upstream path for directing fluid from said primary fluid reservoir,
   said primary reservoir pressure monitor module not in fluid or mechanical engagement with said changeover/reservoir pressure monitor,
   said primary reservoir pressure monitor module including:
   a primary reservoir pressure sensor for measuring the fluid pressure of said primary fluid reservoir, and generating said primary reservoir pressure data,
   a reservoir pressure error signal generator in operative connection with said primary reservoir pressure sensor, for generating said primary reservoir pressure error signal in response to the receipt of reservoir pressure data violative of at least one predetermined pressure limit,
   a pressure monitor microprocessor in operative connection with said primary reservoir pressure sensor and said reservoir pressure error signal generator, said pressure monitor microprocessor receiving said primary reservoir pressure data from said primary reservoir pressure sensor, and said primary reservoir pressure error signals from said pressure error signal generator,
   a pressure monitor transceiver in operative connection with said pressure monitor microprocessor, for electronic communication with a compatible central transceiver situated at said communications/flow monitor module,
   said pressure monitor microprocessor routing said primary reservoir pressure data and said primary reservoir pressure error signals to said pressure monitor transceiver for transmission to said central receiver,
   a communications/flow monitor module in electronic communication with said primary reservoir pressure monitor module, for receiving said primary reservoir pressure error signal and in response transmitting a reservoir changeover signal to a changeover/reservoir pressure monitor module in fluid tight engagement with a reserve fluid reservoir in the pressurized fluid system,
   said changeover/reservoir pressure monitor module including a reservoir changeover device in mechanical engagement with a main valve of said reserve fluid reservoir,
   said changeover/reservoir pressure monitor module actuating said reservoir changeover device to open said reserve fluid reservoir to the pressurized fluid system upon receipt of said changeover signal,
   said changeover/reservoir pressure monitor module in fluid tight engagement with a second upstream path for directing fluid from said reserve fluid reservoir,
   said first and second upstream paths both in direct fluid tight engagement with said communications/flow monitor module,
   said communications/flow monitor module including a central microprocessor in operative connection with said central transceiver, said central microprocessor receiving said primary reservoir pressure error signal from said central transceiver and in response generating a reservoir changeover signal, said reservoir changeover signal being routed to central transceiver for transmission to a changeover transceiver situated at said changeover/reservoir pressure monitor module,
   a digital display that displays at least one of pressure, fluid flow rates, and percentage fluid in said primary fluid reservoir and said reserve fluid reservoir, and a user interface including input buttons for setting alarms,
   said central microprocessor additionally in operative connection with said digital display, said central microprocessor driving said digital display to show a reservoir pressure value transmitted from a source selected from said primary reservoir pressure monitor module and said changeover/reservoir pressure module,
   said fluid tight engagements being made with tubing having at least one connector end chosen from the group consisting of a universal connector, a twist-on nipple, and a v-shaped end.

2. The fluid supply warning and communication system of claim 1, wherein said connector end further includes flanges for preventing disconnection.

3. The fluid supply warning and communication system of claim 1, further including an ETCO2 sensor integrated with said tubing and in electronic communication with said central microprocessor.

4. The fluid supply warning and communication system of claim 1, further including a changeover flow diverter tubing including means for changing the flow from said primary fluid reservoir to said reserve fluid reservoir in electronic communication with said changeover/reservoir pressure monitor module.

5. The fluid supply warning and communication system of claim 1, further including a pulse oximeter for monitoring a patient's SPO2 and/or pulse in electronic communication with said central microprocessor.

6. A method of increasing humidity in a downstream gas path in the gas supply warning and communication system of claim 5, including the step of:
flowing gas through a downstream gas path tubing that increases humidity to an end use appliance.

7. The method of claim 6, wherein the downstream gas path tubing includes Nafion® tubing.

8. The method of claim 7, wherein the Nafion® tubing is operatively connected to an end use appliance chosen from the group consisting of a nasal cannula, oxygen mask, and a CPAP mask.

9. The method of claim 6, wherein the downstream gas path tubing includes a humidification filter operatively connected thereto.

10. The method of claim 9, wherein the downstream gas path is operatively connected to an end use appliance chosen from the group consisting of a nasal cannula, oxygen mask and a CPAP mask.

11. The method of claim 9, wherein the humidification filter includes a port for sterile water.

12. The method of claim 9, wherein the humidification filter includes antimicrobial agents.

13. The method of claim 6, further including the step of reducing side effects normally experienced with end use appliances chosen from the group consisting of nosebleeds and sinus infections.

14. A gas supply warning and communication system including:
a communication/oxygen monitor module in direct gas tight engagement with a first upstream gas path from a primary gas reservoir, in direct gas tight engagement with a second upstream gas path from a reserve gas reservoir, and in gas tight engagement with a downstream gas path toward at least one end use appliance,
a changeover/reservoir pressure monitor module including a reservoir changeover device in mechanical engagement with a main valve of said reserve gas reservoir, and in electronic communication with said communications/flow monitor module,
wherein said communication/oxygen monitor module includes:
an oxygen sensor in exposed to said upstream path for generating oxygen concentration data, a voltmeter in operative connection with said oxygen sensor for calculating and displaying an oxygen concentration value, and an oxygen concentration error signal generator in operative connection with said voltmeter for generating an oxygen concentration error signal in response to an oxygen concentration value violative of at least one predetermined limit,
a central microprocessor in operative connection with a central transceiver,
said central microprocessor also in operative connection with said oxygen sensor, said voltmeter, and said oxygen concentration error signal generator,
said central microprocessor receiving said oxygen concentration error signal from said oxygen concentration error signal generator and in response generating a reservoir changeover signal,
said central microprocessor routing said reservoir changeover signal to said central transceiver for transmission to a compatible changeover transceiver situated at said changeover/reservoir pressure monitor module,
a digital display that displays at least one of pressure, gas flow rates, and percentage gas in said primary gas reservoir and said reserve gas reservoir, and a user interface including input buttons for setting alarms,
wherein said first upstream gas path, said second upstream gas path, and said downstream gas path are made with tubing having at least one connector end chosen from the group consisting of a universal connector, a twist-on nipple, and a v-shaped end.

15. The gas supply warning and communication system of claim 14, wherein said connector end further includes flanges for preventing disconnection.

16. The gas supply warning and communication system of claim 14, wherein said downstream gas path further includes Nafion® tubing operatively connected to said tubing.

17. The gas supply warning and communication system of claim 16, wherein said Nafion® tubing is operatively connected to a device chosen from the group consisting of a nasal cannula, oxygen mask, and a CPAP mask.

18. The gas supply warning and communication system of claim 14, wherein said downstream gas path further includes a humidification filter operatively connected to said tubing.

19. The gas supply warning and communication system of claim 18, wherein said downstream gas path is operatively connected to a device chosen from the group consisting of a nasal cannula, oxygen mask, and a CPAP mask.

20. The gas supply warning and communication system of claim 18, wherein said humidification filter includes a port for sterile water.

21. The gas supply warning and communication system of claim 18, wherein said humidification filter includes antimicrobial agents.

22. The gas supply warning and communication system of claim 14, further including an ETCO2 sensor integrated with said tubing and in communication with said central microprocessor.

23. The gas supply warning and communication system of claim 14, further including a changeover flow diverter tubing including means for changing the flow from said primary gas reservoir to said reserve gas reservoir in electronic communication with said changeover/reservoir pressure monitor module.

24. The gas supply warning and communication system of claim 14, wherein said v-shaped end is further defined as a gripper tube attachable to a tubular outlet, including:
a tube member including a tube wall defining a tube lumen and having at least a first free end, said first free end including a gripping endpiece, said gripping endpiece including:
a distal annular member having an endpiece wall defining an endpiece lumen, said endpiece lumen having a greater diameter than the diameter of said tube lumen, said endpiece wall including an inside surface, said inside surface including a plurality of grooves defining a plurality of ribs, said plurality of ribs projecting into said endpiece lumen, a proximal tapering member having a tapered wall defining a tapered lumen, said tapered wall having a distal end continuous with said endpiece wall, and a proximal end continuous with said tube wall, the diameter of said tapered lumen at said distal end approximating the diameter of said endpiece lumen, the diameter of said tapered lumen at said proximal end having a diameter approximating the diameter of said tube lumen.

25. The gas supply warning and communication system of claim 24, wherein said tube member includes a second free end.

26. The gas supply warning and communication system of claim 25, said second free end terminating in a second gripping endpiece.

27. The gas supply warning and communication system of claim 24, wherein said tube member and said gripping endpiece are of unitary construction.

28. The gas supply warning and communication system of claim 24, wherein said tube member and said gripping endpiece are of separate construction and are interlockable in a fluid tight fit.

29. The gas supply warning and communication system of claim 14, further including a pulse oximeter for monitoring a patient's SPO2 and/or pulse in electronic communication with said central microprocessor.

\* \* \* \* \*